(12) United States Patent
Larsen et al.

(10) Patent No.: US 7,531,323 B2
(45) Date of Patent: May 12, 2009

(54) DIABETES-MEDIATING PROTEINS AND THERAPEUTIC USES THEREOF

(76) Inventors: Peter Mose Larsen, Valmuemarken 16, DK- 5260 Odense S (DK); Stephen J. Fey, Vestervang 772, DK-8000 Aarhus C (DK); Jorn Nerup, Bjerggaardsvanget 13, DK-2840 Holte (DK); Allan E. Karlsen, Vibevang 9, DK-3450 Allerod (DK); Ulla Bjerre Christensen, Virum Overdrevsvej 27, DK-2830 Virum (DK); Flemming Pociot, Brønshøjholmsalle 48, DK-2700 Brønshej (DK); Henrik U. Andersen, Moellemarken 56A, DK-2880 Bagsvaerd (DK)

( * ) Notice: Subject to any disclaimer, the term of this patent is extended or adjusted under 35 U.S.C. 154(b) by 0 days.

(21) Appl. No.: 11/488,184

(22) Filed: Jul. 18, 2006

(65) Prior Publication Data

US 2007/0162985 A1    Jul. 12, 2007

Related U.S. Application Data

(63) Continuation of application No. 09/297,040, filed as application No. PCT/IB97/01627 on Oct. 24, 1997, now Pat. No. 7,078,375.

(60) Provisional application No. 60/029,324, filed on Oct. 25, 1996, provisional application No. 60/030,186, filed on Nov. 5, 1996, provisional application No. 60/030,088, filed on Nov. 5, 1996.

(51) Int. Cl.
*C12P 21/00*   (2006.01)
*A61K 38/00*   (2006.01)

(52) U.S. Cl. .................... 435/69.1; 435/68.1; 530/350; 530/300; 424/9.1; 424/9.322

(58) Field of Classification Search .................. None
See application file for complete search history.

(56) References Cited

U.S. PATENT DOCUMENTS

| | | | |
|---|---|---|---|
| 5,400,249 A | 3/1995 | Soll et al. | |
| 5,424,286 A | 6/1995 | Eng | |
| 5,434,064 A * | 7/1995 | Schlessinger et al. .......... | 435/6 |
| 5,710,024 A * | 1/1998 | Adamou et al. ............ | 435/69.1 |
| 5,760,001 A | 6/1998 | Girten et al. | |
| 5,770,355 A | 6/1998 | Brocia | |
| 5,876,713 A * | 3/1999 | Nishi et al. ................. | 424/94.5 |
| 6,611,766 B1 | 8/2003 | Larsen et al. | |
| 6,640,000 B1 | 10/2003 | Fey et al. | |
| 6,900,044 B2 * | 5/2005 | Kapeller-Libermann .... | 435/226 |
| 7,078,375 B1 | 7/2006 | Larsen et al. | |

OTHER PUBLICATIONS

Botolin et al. (2007) Bone loss and increased bone adiposity in spontaneous and pharmacologically induced diabetic mice, Endocrinology, vol. 148, No. 1, pp. 198-205.*
DiabetesReport.com (2007, updated) "The diabetes report", http://www.diabetesreport.com/, pp. 1-2.*
Genetics, disease, and Dentistry (2007, updated) "Genetics and complex disease", http://www.nchpeg.org/dental/casestudies/Diabetes/1.html, p. 1.*
Wikipedia (2007, updated) "Prediction" http://en.wikipidia.org/wiki?Prediction, p. 1.*
University of Florida News (2007, updated) "Juvenile Diabetes Research Foundation Awards $10.4 Million Grant To Create New Center For The Study Of Gene Therapy And Diabetes At UF", http://news.ufl.edu/2000/12/13/diabetes-3/, pp. 1-3.*
Ishikawa et al. (1997) Changes in the immunoreactivity of protein gene product (PGP) 9.5 in the cochlea of spontaneously diabetic WBN/Kob rats, Diabetologia, vol. 40, No. 2, pp. 173-178 .*
Kaur et al. (2006) Diabetes-induced extracellular matrix protein expression is mediated by transcription coactivator p300, Diabetes, vol. 55, No. 11, pp. 3104-3111.*
Wikipedia (2008, updated) "ubiquitin carboxy-termianl hydrolase L1" http://en.wikipedia.org/wiki/Ubiquitin_carboxy-terminal_hydrolase_L1, pp. 1-2.*
Li et al.(2004) Role of urokinase plasminogen activator and its receptor in metastasis and invasion of neuroblastoma, J. Pediatr. Surg., vol. 39, No. 10, pp. 1512-1519.*
Puricelli et al. (2006) Proteome analysis of cultured fibroblasts from type 1 diabetic patients and normal subjects, J. Clin. Endocrinol. Metab., vol. 91, No. 9, pp. 3507-3514.*
Andersen, H.U., et al., "Genetically determined differences in newborn rat islet sensitivity to interleukin-1 in vitro: no association with the diabetes prone phenotype in the BB-rat," *Acta Endocrinologica* (Copenh) 120:92-98, Copenhagen, Munksgaard (1989).
Andersen, H.U., et al., "Nicotinamide Prevents Interleukin-1 Effect on Accumulated Insulin Release and Nitric Oxide Production in Rat Islets of Langerhans," *Diabetes* 43:770-777, American Diabetes Association (1994).
Andersen, H.U., et al., "Two Dimensional Gel Electrophoresis of Rat Islet Proteins. Interleukin 1β-Induced Changes in Protein Expression Are Reduced by L-Arginine Depletion and Nicotinamide," *Diabetes* 44:400-407, American Diabetes Association (Apr. 1995).
Appel, R.D., et al., "The MELANIE project: From a Biopsy to Automatic Protein Map Interpretation by Computer," *Electrophoresis* 12:722-735, VCH Verlagsgesellschaft mbH (1991).
Bluher, M., et al., "Plasma levels of tumor necrosis factor-alpha, angiotensin II, growth hormone, and IGF-I are not elevated in insulin-resistant obese individuals with impaired glucose tolerance," *Diabetes Care* 24:328-334, American Diabetes Association (Feb. 2001).
Christensen, U.B., et al., "Islet Protein Expression at Diabetes Onset in BB-Rats Differs from that Seen During Islet Allograft Rejection," *Diabetologia* 38(*Suppl 1*):A85, Abstract #327, Springer-Verlag (Aug. 1995).

(Continued)

*Primary Examiner*—Jon P Weber
*Assistant Examiner*—Samuel W. Liu
(74) *Attorney, Agent, or Firm*—Sterne, Kessler, Goldstein & Fox P.L.L.C.

(57) ABSTRACT

Provided are protective and deleterious diabetes-mediating proteins and polynucleotides encoding same, transgenic animals expressing a diabetes-mediating protein, drug screening methods for identifying a test compound capable of altering the expression of a diabetes-mediating protein, and methods of preventing or ameliorating diabetes by administering a compound capable of altering the expression of a diabetes-mediating protein.

2 Claims, 47 Drawing Sheets

OTHER PUBLICATIONS

Eizirik, D.L., et al., "The harmony of the spheres: inducible nitric oxide synthase and related genes in pancreatic beta cells," *Diabetologia 39*:875-890, Springer-Verlag (Aug. 1996).

Eizirik, D.S., et al., "Role of Receptor Binding and Gene Transcription for Both the Stimulatory and Inhibitory Effect of Interleukin-1 in Pancreatic β-Cells," *Autoimmunity 12*:127, 133, Harwood Academic Publishers GmbH (1992).

Ellas, D., et al., "Induction and therapy of autoimmune diabetes in the non-obese diabetic (NOD/Lt) mouse by a 65-kDa heat shock protein," *Proc. Natl. Acad. Sci. USA 87*:1576-1580, National Academy of Science (1990).

Ferre, T., et al., "Correction of diabetic alternations by glucokinase," *Proc. Natl. Acad. Sci. USA 93*:7225-7230, National Academy of Science (Jul. 1996).

Garrels, J.I., et al., "The QUEST System for Quantitative Analysis of Two-dimensional Gels," *J. Biol. Chem. 264*:5269-5282, American Society for Biochemistry and Molecular Biology, Inc. (1989).

Giometti, C.S., et al., "Mouse liver protein database: A catalog of proteins detected by two-dimensional gel electrophoresis," *Electrophoresis 13*:970-991, VCH Verlagsgesellschaft mbH (1992).

Grunberger, G., et al., "Insulin Receptors in Normal and Disease States," *Clin. Endocrinol. Metab. 12*:191-219, W.B. Saunders Company Ltd. (1983).

Helqvist, S., et al., "Interleukin 1 induces new protein formation in isolated rat islets of Langerhans," *Acta Endocrinologica 121*:136-149, Copenhagen, Munksgaard (1989).

Helqvist, S., et al., "Heat shock protein induction in rat pancreatic islets by recombinant human interleukin 1β," *Diabetologia 34*:150-156, Springer-Verlag (1991).

Hughes, J.H., et al., "Interleukin 1 Inhibits Insulin Secretion from Isolated Rat Pancreatic Islets by a Process That Requires Gene Transcription and mRNA Translation," *J. Clin. Invest. 86*:856-863, The Rockefeller University Press, Inc. (1990).

Jaffa, A.A., et al., "Effects of diabetes and insulin on expression of kallikrein and renin genes in the kidney," *Kidney Int. 41*:789-795, Nature Publishing Group (1992).

Jin, J.S., et al., "Shape Representation and Pattern Matching Under the Multi-Channel Theory," *Proceedings of the 3rd Pacific Rim International Conference on Artificial Intelligence*, International Academic Publishers, Bejing, China, Aug. 15-18, vol. 2, pp. 970-975 (1994).

Jungblut, P., et al., "Protein analysis on a genomic scale," *J. Biotech. 41*:111-120, Elsevier (Jul. 1995).

Jungblut, P., et al., "Quantitative Analysis of Two-Dimensional Electrophoretic Protein Patterns: Comparison of Visual Evaluation with Computer-Assisted Evaluation," in *Electrophoresis '84*, Volker Neuhoff ed., Verlag ChemieGmbH, Göttingen, pp. 301-303 (1994).

Karlsen, A.E., et al., "Cloning and Expression of Cytokine-Inducible Nitric Oxide Synthase cDNA from Rat Islets of Langerhans," *Diabetes 44*:753-758, American Diabetes Association (Jul. 1995).

Karlsen, A.E., et al., "Identification and Characterization of Proteins Involved in Cytokine Mediated β-Cell Destruction and Insulin-Dependent Diabetes Mellitus," *Cytokine 9*:912, Abstract #90, Academic Press (Nov. 1997).

Knecht, M., et al., "Dialated Cardiomyopathy: Computer-Assisted Analysis of Endomyocardial Biopsy Protein Patterns by 2-D Gel Electrophoresis," *Eur. J. Clin. Chem. Clin. Biochem 32*:615-624, Walter de Gruyter & Co. (1994).

Korsgren, O., et al., "Hypergycemia induced B Cell Toxicity. The Fate of Pancreatic Islets Transplanted into Diabetic Mice Is Dependent on Their Genetic Background," *J. Clin. Invest. 86*:2161-2168, American Society for Clinical Investigation, Inc. (1990).

Manabe, T., et al., Studies on the Procedure for the Construction of Cellular Protein Databases Employing micro 2-D Electrophoresis: An HL-60 Protein Database, *Electrophoresis 16*:407-422, VCH Verlagsgesellschaft mbH (Mar. 1995).

Mandrup-Poulsen, T., "The role of interleukin-1 in the pathogenesis of IDDM," *Diabetologia 39*:1005-1029, Springer Verlag (Sep. 1996).

Mandrup-Poulsen, T., "Islet Cytotoxicity of Interleukin 1: Influence of Culture Conditions and Islet Donor Characteristics," *Diabetes 36*:641-647, American Diabetes Association (1987).

Martin, J.-P., "Intelligent imaging automates gel analysis for molecular biology," *Scientific Computing World*, pp. 25-28, Cambridge Publishers Ltd. (Sep. 1995).

McLean, M.P., et al., "Differential expression of hepatic sterol carrier proteins in the streptozotocin-treated diabetic rat," *Endocrinology 136*:3360-3368, Endocrine Society (Aug. 1995).

Microsoft Corporation, "Microsoft Excel User's Guide," Microsoft Corporation, pp. 305-316 (1992-1993).

O'Farrell, P.H., "High Resolution Two-Dimensional Electrophoresis of Proteins," *J. Biol. Chem. 250*:4007-4021, American Society for Biological Chemists, Inc. (1975).

O'Farrell, P.Z., et al., "High Resolution Two-Dimensional Electrophoresis of Basic as Well as Acidic Proteins," *Cell 12*:1133-1141, MIT Press (1977).

Pugliese, G., et al., "The diabetic milieu modulates the advanced glycation and product-receptor complex in the mesangium by inducing or upregulating galectin-3 expression," *Diabetes 49*:1249-1257, American Diabetes Association (Jul. 2000).

Pociot, F., et al., "A Comprehensive Approach to Identifying New Susceptibility Genes to Insulin-Dependent Diabetes Mellitus- Combining Proteome and Genome Analyses," *Cytokine 9*:899, Abstract #39, Academic Press (Nov. 1997).

Richardson, J.M. "Differential regulation of glucose transporter activity and expression in red and white skeletal muscle," *J. Biol. Chem. 266*:12690-12694, American Society for Biochemistry and Molecular Biology (1991).

Shi, C.Z., et al., "Protein Databases for Compacted Eight-Cell and Blastocyst-Stage Mouse Embryos," *Mol. Reprod. Develop. 37*:34-47, Wiley-Liss, Inc. (1994).

Steiner, S., et al., "Protein variability in male and female Wistar rat liver proteins," *Electrophoresis 16*:1969-1976, VCH Verlagsgesellschaft mbH (Oct. 1995).

von Herrath, M., et al., "Oral Insulin Treatment Suppresses Virus-induced Antigen-specific Destruction of β Cells and Prevents Autoimmune Diabetes in Transgenic Mice," *J. Clin. Invest. 98*:1324-1331, The American Society for Clinical Investigation (Sep. 1996).

Wachlin, G., et al., "IL-1β, IFN-γ and TNF-α increase vulnerability of pancreatic beta cells to autoimmune destruction," *J. Autoimmune. 20*:303-312, Academic Press (Jun. 2003).

Wadhwa, R., et al., "Identification of a Novel Member of Mouse hsp70 Family," *J. Biol. Chem. 268*:6615-6621, American Society for Biochemistry and Molecular Biology (1993).

Wadhwa, R., et al., "Induction of Cellular Senescence by Transfection of Cytosolic Mortalin cDNA in NIH 3T3 Cells," *J. Biol. Chem. 268*:22239-22242, American Society for Biochemistry and Molecular Biology (1993).

Welsh, N., et al., "Interleukin-1β Increases the Biosynthesis of the Heat Shock Protein hsp 70 and Selectivity Decreases the Biosynthesis of Five Proteins in Rat Pancreatic Islets," *Autoimmunity 9*:33-40, Hardwood Academic Publishers GmbH (1991).

Wilkins, M.R., et al., "From Proteins to Proteomes: Large Scale Protein Identification by Two-Dimensional Electrophoresis and Amino Acid Analysis," *Bio/technology 14*:61-65, Nature Publishing Co. (Jan. 1996).

Wilm, M., et al., "Femtomole sequencing of proteins from polycrylamide gels by nano-electrospray mass spectrometry," *Nature 379*:466-469, Macmillan Publishers Ltd. (Feb. 1996).

Young, D.S., and Tracy, R.P., "Clinical applications of two-dimensional electrophoresis," *J. Chromatography A 698*:163-179, Elsevier (Apr. 1995).

* cited by examiner

MISASRAAAARLVGTAASRSPAAARPQDGWNGLSHEAFRFVSR
DYASEAIKGAVVGIDLGTTNSCVAVMEGKQAKVLENAEGARTTPSVVAFTADGERLV
MPAKRQAVTNPNNTFYATKRLIGRRYDDPEVQKDTKNVPFKIVRASNGDAWVEAHGK
YSPSQIGAFVLMKMKETAENYLGHTAKNAVITVPAYFNDSQRQATKDAGQISGLNVL
VINEPTAAALAYGLDKSEDKVIAVYDLGGGTFDISILEIQKGVFEVKSTNGDTFLGG
DFDQALLRHIVKEFKRETGVDLTKDNMALQRVREAAEKAKCELSSSVQTDINLPYLT
DASGPKHLNMKLTRAQFEGIVTDLIKRTIAPCQKAMQDAEVSKSDIGEVILVGGMTR
PKVQQTVQDLFGRAPSKAVNPDEAVAIGAAIQGGVLAGDVTDVLLLDVTPLSLGIET
GGVFTKLINRNTTIPTKKSQVFSTAADGQTQVEIKVCQGEREMAGDNKLLGQFTLIG
PPAPRGVPQIEVTFDIDANGIVHVSAKDKGTGREQQIVIQSSGGLSKDDIENMVKNA
KYAEEDRRKKERVEAVNMAEGIIHDTETKMEEFKDQLPADECNKLKEEISKVRALLA
KDSETGENIRQAASSLQQASLKLFEMAYKKMASEREGSGSSGTGEQKEDQKEEKQ

FIG.2

MISASRAAAARLVGAAASRGPTAARHQDSWNGLSHEAFRLVSR
DYASEAIKGAVVGIDLGTTNSCVAVMEGKQAKVLENAEGARTTPSVVAFTADGERLV
MPAKRQAVTNPNNTFYATKRLIGRRYDDPEVQKDIKNVPFKIVRASNGDAWVEAHGK
YSPSQIGAFVLMKMKETAENYLGHTAKNAVITVPAYFNDSQRQATKDAGQISGLNVL
VINEPTAAALAYGLDKSEDKVIAVYDLGGGTFDISILEIQKGVFEVKSTNGDTFLGG
DFDQALLRHIVKEFKRETGVDLTKDNMALQRVREAAEKAKCELSSSVQTDINLPYLT
DSSGPKHLNMKLTRAQFEGIVTDLIRRTIAPCQKAMQDAEVSKSDIGEVILVGGMTR
PKVQQTVQDLFGRAPSKAVNPDEAVAIGAAIQGGVLAGDVTDVLLLDVTPLSLGIET
GGVFTKLINRNTTIPTKKSQVFSTAADGQTQVEIKVCQGEREQQIVIQSSGGLSKDDIENMVKNA
PPAPRGVPQIEVTFDIDANGIVHVSAKDKGTRREQQIVIQSSGGLSKDDIENMVKNA
KYAEEDRRKKERVEAVNMAEGIIHDTETKMEEFKDQLPADECNKLKEEISKMRELLA
KDSETGENIRQAASSLQQASLKLFEMAYKKMASEREGSGSSGTGEQKEDQKEEKQ

FIG.3

MADGFSLNDALAGSGNPNPRGWPGAWGNQPGAGGYPGASYPGA
PGQAPPGGYPGQAPPSAYPGTGPSAYPGTAPGAYPGPTAPGAFPGQPGGPGAYPS
PGAYPSAPGAYPATGPFGAPTGPLTVPYDMPLPGGVMPRMLITIIGTVKPNANSITL
FKKGNDIAFHFNPRFNENNRRVIVCNTKQDNNWGREERQSAFPFESGKPFKIQVLVE
DHFKVAVNDVHLLQYNHRMKNLREISQLGIGDITLTSASHAMI

FIG.4

MADNFSLHDALSGSGNPNPQGWPGAWGNQPAGAGGYPGASYPG
YPGQAPPGAYHGAPPGAYPGAPAPGVYPGPPSGPGAYPSSGQPSAPGAY
ATGPYGAPAGPLIVPYNLPLPGGVVPRMLITILGTVKPNANRIALDFQRGNDVAFHF
PRFNENNRRVIVCNTKLDNNWGREERQSVFPFESGKPFKIQVLVEPDHFKVAVNDAH
LQYNHRVKKLNEISKLGISGDIDLTSASYTMI

FIG.5

DIABETES-MEDIATING PROTEINS AND THERAPEUTIC USES THEREOF

CROSS-REFERENCE TO RELATED APPLICATIONS

This application is a continuation of prior U.S. application Ser. No. 09/297,040, filed Jul. 21, 1999 (U.S. Pat. No. 7,078, 375), which was the National Stage of International Appl. No. PCT/IB97/01627, filed Oct. 24, 1997 (now abandoned), which claims the benefit of U.S. Provisional Appl. No. 60/029,324, filed Oct. 25, 1996, and U.S. Provisional Appl. No. 60/030,186, filed Nov. 5, 1996, and U.S. Provisional Appl. No. 60/030,088, filed Nov. 5, 1996, and U.S. application Ser. No. 08/897,098, filed Jul. 18, 1997.

BACKGROUND OF THE INVENTION

1. Field of the Invention

This invention relates generally to diabetes-mediating proteins, methods of identifying diabetes-mediating proteins, transgenic animals useful in the assays of the invention, methods for screening for drugs which affect the expression of diabetes-mediating proteins, and therapeutic compounds for the treatment and prevention of diabetes.

2. Related Art

The development of insulin-dependent diabetes mellitus (IDDM) in man, and in animal models of human disease, is characterized by mononuclear cell infiltration and, β-cell destruction in the pancreatic islets (insulitis). The mechanisms behind β-cell destruction is not known. Accumulating evidence indicates that the cytokine interleukin-1,6 (IL-1β), primarily produced by macrophages and monocytes, may be a mediator of islet, β-cell destruction.

Animal models of human diabetes include diabetes-prone BB (BB-DP) rats and non-obese diabetic (NOD) mice. 2-Dimensional (2D) gel maps of rat islet proteins have been constructed and used to determine qualitative and quantitative changes in protein synthesis resulting with in vitro exposure of rat islet cells to IL-1β (Andersen et al. *Diabetes* 44:400-407 (1995)).

Transgenic animal models of human diseases are known. For example, one model for human diabetes is a transgenic mouse expressing a viral protein in the pancreatic β cells under control of the rat insulin promoter (van Herrath et al. *J. Clin. Invest.* 98:1324-1331 (1996)). Less than 2% of the transgenic mice develop diabetes spontaneously; however, after a 2 month challenge with the virus, IDDM occurs in more than 95% of the mice.

SUMMARY OF THE INVENTION

The invention is based, in part, on the discovery and identification of diabetes-mediating (DM) proteins. DM proteins are proteins which are involved in the development of diabetes or in the prevention of diabetes development in a subject at risk for the development of diabetes, and are identified by differential expression during the presence or absence of disease development. The development of diabetes includes all stages which precede the clinically detectable stage.

Accordingly, in one aspect the invention features substantially purified diabetes-mediating proteins exhibiting an altered expression during development of diabetes relative to expression in the absence of diabetes development. The purified diabetes-mediating proteins of the invention are selected from the proteins listed in Tables 1 and 2. Novel diabetes-mediating proteins are provided characterized by molecular weight, pI, and the mass spectroscopic characteristics as shown in FIGS. 6-40. These proteins, referred to by their position on 10% IEF (isoelectric focusing) or NEPHGE (non-equilibrium pH-gradient electrophoresis) 2-dimensional gels (FIGS. 1A 1B), are selected from the group consisting of NEPHGE 7, 9, 102, 123, 129, 130, 174, 181, 182, 211, 231, 236, 253, 298, and IEF 665, 939, 941, 950, 1196.

DM proteins are further characterized as protective or deleterious DM proteins. A protective diabetes-mediating protein ("protective protein") is characterized as a protein capable of protecting against the development of diabetes and/or delaying the onset of diabetes in a subject at risk for development of diabetes, or ameliorating the symptoms of diabetes in a subject suffering from diabetes. A protective protein may also be a protein which does not alter expression during development of diabetes, but exhibits an altered expression in a subject at risk for diabetes who escapes the development of diabetes. A deleterious diabetes-mediating protein ("deleterious protein") is characterized as a protein capable of enhancing the development of diabetes, increasing the risk of a subject developing diabetes, or reducing the time required for development of diabetes in a subject at risk for development of diabetes. A deleterious protein may also be a protein which does not alter expression during development of diabetes, but exhibits an altered expression in a subject at risk for diabetes who escapes the development of diabetes. The diabetes-mediating protein of the invention may be identified by any means known to the art, including gel electrophoresis, immunoblotting, mass spectrometry, or chromatography, and is characterized by an altered protein expression during development of diabetes as compared to the same protein expressed in the absence of diabetes development. U.S. provisional patent application Ser. No. 60/029,324 identifies proteins expressed in pancreatic islet cells identified by molecular weight and pI (FIGS. 1A and 1B). The instant application provides a selection of these proteins which have been identified as diabetes-mediating proteins, as listed in Tables 1 and 2, and FIGS. 6-40.

The diabetes-mediating proteins of the invention are useful in drug screening assays for identifying compounds capable of modulating the development of diabetes, useful as therapeutic agents for the treatment or prevention of diabetes, and useful as targets of therapeutic agents capable of preventing or ameliorating diabetes by modulating the expression of the diabetes-mediating protein.

Changes in the expression of specific DM proteins is diagnostically useful as indicative of the development of diabetes. Accordingly, in one aspect the invention features a method for diagnosing the development of diabetes by measuring an increase in protein expression in one or more proteins selected from the group consisting of the diabetes-mediating proteins listed in Table 1, and a decrease in the protein expression of one or more proteins selected from the list consisting of the diabetes-mediating proteins listed in Table 2. Changes in protein expression are measured in a test subject suspected of developing diabetes or at risk for the development of diabetes and are expressed relative to protein expression in a normal non-diabetes control. In a preferred embodiment, changes of combinations of one or more of the proteins of Tables 1 and 2 is indicative of the development of diabetes. In a more preferred embodiment, changes of a combination of 5 or more of the proteins of Tables 1 and/or 2 is indicative of the development of diabetes. In an even more preferred embodiment, changes of a combination of 10 or more of the proteins of Tables 1 and/or 2 is indicative of the development of diabetes.

In one aspect, the invention features an in vivo assay method for identifying proteins which are involved in the development of disease, e.g., diabetes. In a specific embodiment of the in vivo assay method of the invention, cells which secret insulin or are capable of developing into insulin producing cells are transplanted to an immunologically compatible host animal which is an animal at risk for the development of diabetes. Protein expression is analyzed in transplanted cells rescued at time points between the time of transplantation and disease onset, and proteins exhibiting an altered expression during disease development relative to their expression in the absence of the development of diabetes are identified. In specific embodiments, the transplanted cells are neonatal islet cells which are transplanted into a animal model at risk for development of diabetes. In one specific embodiment, the neonatal islet cells are taken from neonatal BB-DP rats and the host animal is BB-DP rat. In another embodiment, the source of transplanted cells and host animals are NOD mice.

The invention provides identified diabetes-mediating proteins which may be further characterized as protective or deleterious proteins. In one embodiment of the invention, a candidate protective or deleterious protein is identified in vitro by transfecting cultured cells with a polynucleotide encoding the candidate protective or deleterious protein, and the effect of expression of the diabetes-mediating protein on in vitro cell functionality upon challenge with IL-1β determined. The polynucleotide may be operably connected to an inducible promoter such that expression of the candidate protective or deleterious protein is under exogenous control. Exogenous control may be exerted by agents, e.g., interferon, such agents being determined by the promoter selected. In specific embodiments, cell functionality is determined by measurement of nitric oxide (NO) production, insulin secretion, cell survival, and/or cytotoxicity upon exposure to IL-1β.

In an in vivo method for identifying protective or deleterious diabetes-mediating proteins, a transgenic mammal is generated expressing the candidate protein, wherein the transgenic mammal is at risk for developing diabetes, and the effect of transgene expression on the development and timing of diabetes onset is determined. A protective protein is one which prevents, inhibits, or slows the development of diabetes in a subject at risk for diabetes, and a deleterious protein is one that causes the development of diabetes, increases the risk of development of diabetes, or decreases the time required for the development of diabetes in a subject at risk for developing diabetes. A deleterious protein is also a protein that prevents or interferes with the expression of a protective protein.

The invention includes a substantially purified protective or deleterious diabetes-mediating protein, and polynucleotide sequence which encodes the diabetes-mediating protein of the invention. In one non-limiting embodiment, the protective protein is galectin-3 (FIGS. 4 and 5) (SEQ ID NOs:1-2). In another non-limiting embodiment, the deleterious protein is mortalin (FIGS. 2-3) (SEQ ID NOs:3-4).

In one aspect, the invention features a transgenic mammal having an exogenous diabetes-mediating protein gene or genes inserted into its genome. The transgenic mammal of the invention is useful in assay methods for determining the effect of the expression of a diabetes-mediating protein in the development of diabetes, and for identifying protective or deleterious proteins. The transgene may be a natural, or partially or wholly artificial diabetes-mediating gene, and may be different from or the same as an endogenous diabetes-mediating protein gene. In one embodiment, the transgene is under control of an inducible promoter.

In a related aspect, the invention features a transgenic mammal having an exogenous deleterious gene, and exhibiting an increased incidence of the spontaneous development of diabetes within a predictable period of time. In preferred embodiments, the transgenic mammal exhibits a greater than 50% chance, more preferably a greater than 60% chance, even more preferably a greater than 70% chance, even more preferably a greater than 80% chance, and most preferably a greater than 90% chance of developing diabetes. In an embodiment of the invention, the transgenic mammal of the invention is transgenic for one or more genes encoding a deleterious diabetes-mediating protein. In another embodiment, the transgenic mammal additionally has one or more endogenous diabetes-mediating protein genes ablated. Generally, the transgenic mammal will have the transgenic gene under control of an insulin, cytomegalovirus (CMV), interferon, or myosin heavy chain (MHC) promoter. In further specific embodiments, a transgenic mammal expresses elevated levels of an endogenous diabetes-mediating gene obtained by an enhanced promoter or a high copy number of an endogenous diabetes-mediating gene. In further specific embodiments, the transgenic mammal has a disrupted diabetes-mediating protein gene.

The invention further includes mammals in which an endogenous diabetes-mediating protein gene is exogenously altered by methods known in the art, for example, by application of gene activation technologies such as that described in U.S. Pat. No. 5,641,670, entirely incorporated herein by reference.

In one aspect, the invention features an assay for screening compounds which effect the expression of one or more diabetes-mediating proteins. In one embodiment, animals at risk for spontaneous development of diabetes are used in an assay for determining the ability of a test compound to effect the expression of one or more diabetes-mediating protein(s). In a preferred embodiment, the assay animal is the transgenic mammal of the invention having a high risk of the development of diabetes. By the term "effect the expression of a diabetes-mediating protein" is meant a compound which induces, enhances, inhibits, or decreases the expression of an endogenous diabetes-mediating protein.

In specific embodiments, the invention provides an assay for identifying a compound capable of inducing or enhancing the expression of an endogenous protective protein, and thus to delay or inhibit the development of diabetes. In another specific embodiment, the assay method of the invention is useful for identifying a compound capable of suppressing or inhibiting the expression of a deleterious diabetes-mediating protein, thus delaying or inhibiting the development of diabetes.

In a related aspect, the invention provides an assay for identifying a compound which modulates the activity of a diabetes-mediating protein, e.g., an agonist, an antagonist, or by blocking a post-translational step required for activation of a diabetes-mediating protein. Changes in the expression of specific DM proteins are useful in a screening method for identifying compounds capable of modulating the expression of DM proteins. A compound which modulates the expression of one or more diabetes mediating proteins is useful as a potential therapeutic in the treatment or prevention of diabetes. Accordingly, in one aspect the invention features an assay method for identifying compounds capable of modulating the expression of diabetes-mediating proteins having the steps of contacting a test compound with a cell or tissue expressing one or more diabetes-mediating proteins, and determining the effect of the test compound on the expression of one or more diabetes-mediating proteins. Determination of the effect of a compound may be conducted by a variety of methods known to the art, including hybridization to probes or other oligonucleotides, antibody recognition, e.g., immuno-diffusion, immuno-fluorescence, ELISA (Enzyme-Linked Immunosorbent Assay), RIA (radioimmunoassay), blotting, immuno-precipitation, immuno-electrophoresis, or chromatography, and electrophoresis. A compound capable of increasing the expression of one or more proteins selected from the group consisting of the diabetes-mediating proteins listed in Tables 1 and 2 and decreasing the expression of one or more proteins selected from the list consisting of the diabetes-mediating proteins listed in Tables 1 and 2 is a candidate therapeutic agent for the prevention or treatment of diabetes. Changes in protein expression are determined relative to expression in the absence of the test compound.

In another aspect, the invention provides a therapeutic method for preventing diabetes in a subject at risk for diabetes or of ameliorating the symptoms of diabetes in a diabetic subject by administering a therapeutically effective amount of a protective diabetes-mediating protein. Preferably the subject is a human. Also included in the invention is gene therapy by providing a polynucleotide encoding a protective diabetes-mediating protein. The invention further includes a therapeutic method for preventing and/or treating diabetes by administering an effective amount of a polynucleotide which inhibits the in vivo expression of a deleterious diabetes-mediating protein. Candidate therapeutic compounds are selected from the proteins of Tables 1 and 2.

In a related aspect, the invention provides a therapeutic method of preventing and/or treating diabetes in a subject at risk for diabetes by administering a therapeutically effective amount of a compound capable of suppressing or reducing the expression of an endogenous deleterious diabetes-mediating protein. In another embodiment, the invention provides a therapeutic method of preventing and/or treating diabetes by administering a therapeutically effective amount of a compound capable of inducing or enhancing the expression of an endogenous protective diabetes-mediating protein. In a related aspect, the invention provides a therapeutic method of preventing and/or treating diabetes in a subject at risk for diabetes by administering a therapeutically effective amount of a compound capable of modulating the activity of a diabetes-mediating protein, e.g., as an agonist, an antagonist, or by preventing the activation of a diabetes-mediating protein. The therapeutic method of the invention includes ex vivo methods known to the art for providing the therapeutic agent to a subject in need thereof.

An object of the invention is to identify proteins which mediate diabetes onset.

An object of the invention is to provide an in vivo assay for identification of diabetes-mediating proteins.

Another object of the invention is to provide diabetes-mediating proteins which are useful in assays for identifying test compounds capable of preventing, delaying, or ameliorating diabetes in a subject.

Another object of the invention is to provide transgenic animals useful in assays to identify protective or deleterious diabetes-mediating proteins.

Another object of the invention is to provide transgenic animals useful in assay to identify test compounds capable of affecting the expression of a diabetes-mediated protein.

Another object of the invention is to provide a transgenic host mammal (which is small, e.g., less than 1 kg when full grown, and inexpensive to maintain) such as a mouse, rat or hamster which includes a natural, or partially or wholly artificial diabetes-mediating gene.

An advantage of the present invention is that the transgenic mammal can be used to identify a protective protein which can prevent or inhibit disease development in a manner which is substantially faster, more efficient and cheaper than presently available assay methods.

Another advantage is that transgenic mammal can be used as test animals for testing drugs for efficacy in the treatment of humans suffering from diabetes or at risk for the development of diabetes.

Another object of the invention is to provide an assay for identification of test compounds which effect the expression of a diabetes-mediating protein and which are capable of preventing the onset of diabetes in a subject at risk for development of the disease, or for ameliorating the symptoms of diabetes in a diabetic subject.

These and other objects, advantages, and features of the invention will become apparent to those persons skilled in the art upon reading the details of the diabetes-mediating gene(s) and protein(s), assay method, and transgenic mouse as more fully described below, and from the claims.

BRIEF DESCRIPTION OF THE FIGURES

FIG. 1A is the isoelectric focusing gel (IEF; pH 3.5-7). FIG. 1B is the non-equilibrium pH-gradient electrophoresis gel (NEPHGE; pH 6.5-10.5). Arrows mark 105 diabetes-mediating proteins.

FIG. 2 (SEQ ID NO: 1) is the amino acid sequence of murine mortalin.

FIG. 3 (SEQ ID NO: 2) is the amino acid sequence of human mortalin.

FIG. 4 (SEQ ID NO: 3) is the amino acid sequence of rat galectin.

FIG. 5 (SEQ ID NO: 4) is the amino acid sequence of human galectin.

DETAILED DESCRIPTION OF THE PREFERRED EMBODIMENTS

Figure 1A:
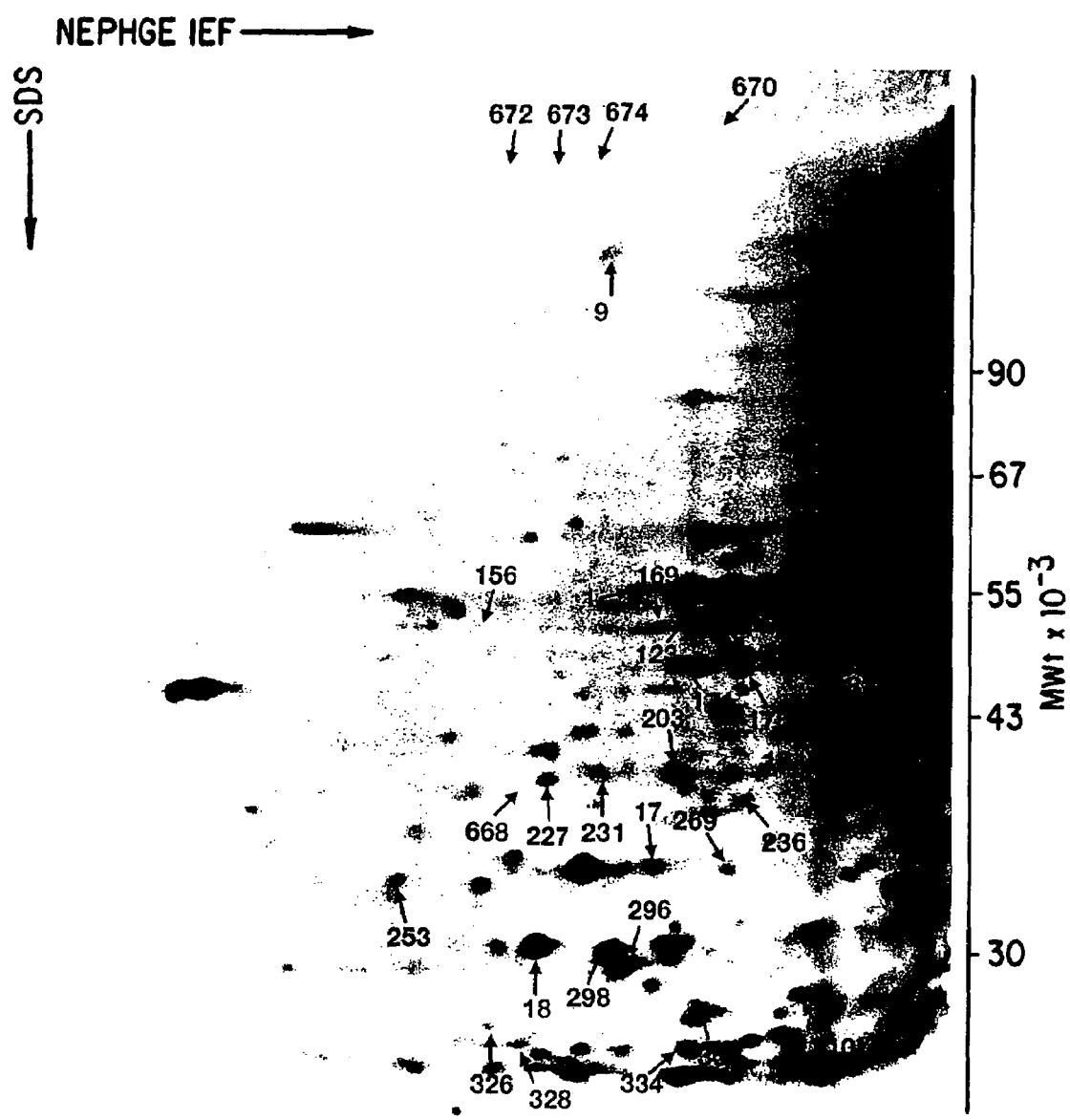
FIGS. 1A and 1B show a fluorograph of a 2-dimensional gel of proteins expressed in neonatal rat islet cells incubated for 24 h in RPMI 1640+0.5% normal human serum, followed by a 4 h labeling with [$^{35}$S]-methionine.

Before the present diabetes-mediating proteins and genes, assay methodology, and transgenic used in the assay are described, it is to be understood that this invention is not limited to particular assay methods, diabetes-mediating proteins and genes, test compounds, or transgenic mammals described, as such methods, genes, preparations, and animals may, of course, vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus, for example, references to "diabetes-mediating protein" or "a diabetes-mediating protein" include mixtures of such diabetes-mediating proteins, reference to "the formulation" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Definitions

The term "protein" includes proteins, polypeptides, and peptides which are chains of amino acids, including all post-translational modifications (e.g., processing and truncations, glycosylations or phosphorylations) which often play decisive roles in modulating protein function. The term also encompasses natural proteins as well as synthetic or recombinant proteins, polypeptides, and peptides.

The term "diabetes" includes insulin-dependent diabetes melitis (IDDM) and type I diabetes. The term "diabetes-related diseases" includes such conditions as obesity, circulatory deficiencies, insulin-resistance, syndrome X, diabetic retinopathy, diabetic neuropathy, and the involvement of advanced glycation end products (AGE) in neuropathy and atherosclerosis.

The term "diabetes-mediating protein" means a protein which is involved in the development of diabetes. A diabetes-mediating protein is a protein which exhibits an altered expression during the development of diabetes, that is, a protein which is up- or down-regulated, or whose expression is modulated up or down, during the development of diabetes, as compared to the expression of the same protein in the absence of the development of diabetes. A diabetes-mediating protein also means a protein that is modified as associated with the development of diabetes or diabetes-related diseases. Further, interleukin 1α (IL-1α) is expected to have a detrimental effect on the insulin secreting islets of Langerhans, both in vivo and in vitro and is considered to play a major role in the development of diabetes. The treatment of islets causes the modulation of 106 proteins, up or down regulating their expression. For the purposes of this invention, the term "diabetes mediating protein" is defined to also include all the proteins (and all of their modification products) which have been demonstrated to be modulated by IL-α in rat islets in vitro, as further described in U.S. provisional application Nos. 60/029,324 (filed Oct. 25, 1996), 60/030,186 (filed Nov. 5, 1996) and 60/030,088 (filed Nov. 5, 1996), the entire contents of which are incorporated herein by reference.

The term "protein modification" includes any change in structure (i.e., a qualitative change) of a protein. Such modifications can include, but are not limited to, changes in the amino acid sequence, transcriptional or translational splice variation, pre- or post-translational modifications to the DNA or RNA sequence, addition of macromolecules or small molecules to the DNA, RNA or protein, such as peptides, ions, vitamins, atoms, sugar-containing molecules, lipid-containing molecules, small molecules and the like, as well-known in the art.

One type of protein modification according to the present invention is by one or more changes in the amino acid sequence (substitution, deletion or insertion). Such changes could include, at one or more amino acids, a change from a charged amino acid to a different charged amino acid, a non-charged to a charged amino acid, a charged amino acid to a non-charged amino acid (e.g., giving rise to difference in pI or possibly molecular weight). Any other change in amino acid sequence is also included in the invention. The overall positional change in a gel of a modified protein with a changed amino acid sequence also depends on how many overall charges there are in the protein, as known in the art. Changes in the resolution of the gel (e.g., changing the pH or other gradient component) of the gel can allow detection of minor or major amino acid sequence changes. The type of analysis can also affect how changes are detected, e.g., using sequencing, mass spectrometry, labeled antibody binding.

Another type of modification is by change in length, conformation or orientation in the protein-encoding DNA or RNA that affects the way the open reading frame is read in the cell, which can give large changes in position of the spot on the gel and which could affect the analysis of the protein type and position in the gel.

Another type of protein modification is by changes in processing of the protein in the cell. A non-limiting example is where some proteins have an "address label" specifying where in (or outside of) the cell they should be used. Such a label or tag can be in the form of a peptide, a sugar or a lipid, which when added or removed from the protein, determines where the protein is located in the cell.

A further type of protein modification is due to the attachment of other macromolecules to a protein. This group can include, but is not limited to, any addition/removal of such a macromolecule. These molecules can be of many types and can be either permanent or temporary. Examples include: (i) polyribosylation, (ii) DNA/RNA (single or double stranded); (iii) lipids and phospholipids (e.g., for membrane attachment); (iv) saccharides/polysaccharides; and (v) glycosylation (addition of a multitude of different types of sugar and sialic acids in a variety of single and branched structures so that the number of variations possible is large).

Another type of protein modification is due to the attachment of other small molecules to proteins. Examples can include, but are not limited to: (i) phosphorylation; (ii) acetylation; (iii) uridylation; (iv) adenylation; (v) methylation, and (vi) capping (diverse complex modification of the N-terminus of the protein for assorted reasons). Most of these changes are often used to regulate a protein's activity. (v) and (vi) are also used to change the half-life of the protein itself. These protein changes can be detected by 2D using several methods, such as labeling, changes in pI, antibodies or other specific techniques directed to the molecules themselves, as known in the art. Molecular weight changes can be, but may not usually be detectable by 2DGE (2-dimensional gel electrophoresis). MALDI (matrix assisted laser desorption ionisation mass spectrometry) is preferred to detect and characterize these modifications.

The term "expression" is meant to include not only the physical expression of a protein, but also as a measure of the activity of an expressed protein. For example, a protein can be expressed as an inactive form, which is activated by phosphorylation. While the actual expression of the protein has not changed, its effective expression (activity) has been modified. On a gel, the change in activity may be measured as the change in expression of a modified form of the protein.

The term "affected protein" means a protein that is modified in expression or modified structurally. An affected protein can thus be a protein in which expression is modified due to treatment with one or more compounds, a diseased or pathological state and/or an immunological change in or outside the cell from which the protein is derived. An affected protein can alternatively or additionally also be a protein which exhibits an altered expression as up- or down-regulated, or whose expression is modified in structure in any way that can be detected by a method of the present invention, as compared to the the expression of the same protein (i.e., an "unaffected protein") in the absence of such treatment, disease or immunological change.

The term "diabetes-mediating gene or polynucleotide" means genetic material encoding a protein, peptide, or protein fragment which encodes an intact or fragment of a diabetes-mediating protein. The term includes any gene from any species which encodes a diabetes-mediating protein. A diabetes-mediating gene or polynucleotide may be naturally occurring or partially or wholly synthetic.

The term "substantially pure," when referring to a polypeptide, means a polypeptide that is at least 60%, by weight, free from the proteins and naturally-occurring organic molecules with which it is naturally associated. A substantially pure diabetes-mediating protein is at least 75%, more preferably at least 90%, and most preferably at least 99%, by weight, diabetes-mediating protein. A substantially pure diabetes-mediating protein can be obtained, by extraction from a natural source; by expression of a recombinant nucleic acid encoding a diabetes-mediating protein, or by chemically synthesizing the protein. Purity can be measured by any appropriate method, e.g., column chromatography, polyacrylamide gel electrophoresis, or HPLC analysis.

As used herein, "polynucleotide" refers to a nucleic acid sequence of deoxyribonucleotides or ribonucleotides in the form of a separate fragment or a component of a larger construct DNA encoding portions or all of the polypeptides of the invention can be assembled from cDNA fragments or from oligonucleotides that provide a synthetic gene which can be expressed in a recombinant transcriptional unit. Polynucleotide sequences of the invention include DNA, RNA, and cDNA sequences, and can be derived from natural sources or synthetic sequences synthesized by methods known to the art.

As used herein, an "isolated" polynucleotide is a polynucleotide that is not immediately contiguous (i.e., covalently linked) with either of the coding sequences with which it is immediately contiguous (i.e., one at the 5' end and one at the 3' end) in the naturally-occurring genome of the organism from which the polynucleotide is derived. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

The isolated and purified polynucleotide sequences of the invention also include polynucleotide sequences that hybridize under stringent conditions to the polynucleotide sequences specified herein. The term "stringent conditions" means hybridization conditions that guarantee specificity between hybridizing polynucleotide sequences. One skilled in the art can select post-hybridization washing conditions, including temperature and salt concentrations, which reduce the number of non-specific hybridizations such that only highly complementary sequences are identified (Sambrook et al. in *Molecular Cloning*, 2d ea.; Cold Spring Harbor Laboratory Press, Cold Spring Harbor, N.Y. (1989), hereby specifically incorporated by reference). For instance, such conditions are hybridization under specified conditions, e.g. involving pre-soaking in 5×SSC and pre-hybridizing for 1 h at about 40° C. in a solution of 20% formamide, 5× Denhardt's solution, 50 mM sodium phosphate, pH 6.8, and 50 µg of denatured sonicated calf thymus DNA, followed by hybridization in the same solution supplemented with 100 µM ATP for 18 h at about 40° C. (Sambrook et al. supra (1989)). The isolated and purified polynucleotide sequences of the invention also include sequences complementary to the polynucleotide encoding a diabetes-mediating protein (antisense sequences) and ribozymes.

The terms "host animal" and "host mammal" are used to describe animals into which donor cells are transplanted. Convenient host animals include mice, hamsters and rats.

The terms "ablated diabetes-mediating protein gene", "disrupted diabetes-mediating gene", and the like are used interchangeably herein to mean an endogenous diabetes-mediating protein gene which has been altered (e.g., add and/or remove nucleotides) in a manner so as to render tie gene inoperative. It is also used to include ablation or modification of controlling sequences or regulatory genes which also render the gene inoperative (partially or completely).

The term "increased risk of developing diabetes" and the like mean animals which are genetically predisposed to develop diabetes, preferably having a greater than 50% chance, more preferably a greater than 60% chance, even more preferably a greater than 70% chance, even more preferably a greater than 80% chance, and most preferably a greater than 90% chance to develop diabetes.

By "altered protein" or "altered protein expression" is meant proteins whose expression is increased ("up regulated"), decreased ("down regulated"), inhibited (i.e., turned off), or induced (i.e., turned on) during the development of diabetes.

By the term "modulating the activity" or the like is meant altering the activity of a protein to prevent or enhance its normal activity, e.g., as an agonist, antagonist, or by blocking a post-translational modification step required for protein activity.

By the term "effective amount" or "therapeutically effective amount" is meant an amount of a compound sufficient to obtain the desired physiological effect, e.g., suppression of or delay of the development of diabetes.

The terms "treatment", "treating" and the like are used herein to generally mean obtaining a desired pharmacologic and/or physiologic effect. The effect may by prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease from occurring in a subject which may be predisposed to the disease but has not yet been diagnosed as having it;

(b) inhibiting the disease, i.e., arresting its development; or (c) relieving the disease, i.e., causing regression of the disease. The invention is directed to treating patients with or at risk for development of diabetes and related conditions mediated diabetes, insulin insufficiency, or insulin resistance. More specifically, "treatment" is intended to mean providing a therapeutically detectable and beneficial effect on a patient at risk for or suffering from diabetes.

"Treatment" refers to both therapeutic treatment and prophylactic or preventative measures, wherein the object is to prevent or slow down the development of a disease. Those in need of treatment include those already with the disorder as well as those prone to have the disorder or those in which the disorder is to be prevented.

The terms "synergistic", "synergistic effect" and like are used herein to describe improved treatment effects obtained by combining one or more therapeutic agents. Although a synergistic effect in some field is meant an effect which is more than additive (e.g., 1+1=3), in the field of medical therapy an additive (1+1=2) or less than additive (e.g., 1+1=1.6) effect may be synergistic. For example, if each of two drugs were to inhibit the development of diabetes by 50% if given individually, it would not be expected that the two drugs would be combined to completely stop the development of diabetes. In many instances, due to unacceptable side effects, the two drugs cannot be administered together. In other instances, the drugs counteract each other and slow the development of diabetes by less than 50% when administered together. Thus, a synergistic effect is said to be obtained if the two drugs slow the development of diabetes by more than 50% while not causing an unacceptable increase in adverse side effects.

Abbreviations used herein include: IDDM=insulin dependent diabetes mellitus; BB-DP=diabetes prone Bio-Breeding rats; NOD=non-obese diabetic-mice.

GENERAL ASPECTS OF THE INVENTION

The present invention encompasses several aspects including: (1) diabetes-mediating proteins identified by differential expression in the presence and absence of the development of diabetes; (2) patterns and combinations of DM proteins useful for predicting the development of diabetes and for identifying a compound able to effect a combination of DM proteins in a desired manner; (3) protective diabetes-mediating proteins; (4) deleterious diabetes-mediating proteins; (5) a method to diagnose for the onset or development of diabetes based on the detection of one or more of the DM proteins, their post-translational modification or degradation products in a body fluid; (6) an in vivo method for identifying a diabetes-mediating protein; (7) a transgenic mammal containing an exogenous gene encoding a diabetes-mediating protein; (8) a transgenic mammal useful in an in vivo assay for identifying protective or deleterious diabetes-mediating proteins; (9) an in vitro assay using transduced cultured cells expressing a diabetes-mediating protein useful for identifying protective or deleterious diabetes-mediating proteins; (10) an in vivo assay using transduced islet cells expressing a diabetes-mediating protein useful for identifying protective or deleterious diabetes-mediating proteins; (11) an improved animal model for human diabetes, which animal exhibits a high incidence of diabetes within a predictable period of time; (12) in vivo assay methods for identifying test compounds capable of inducing or enhancing the expression of one or more protective proteins; (13) in vivo assay methods for identifying test compounds capable of inhibiting or reducing the expression of deleterious proteins, (14) methods for treating diabetes and/or preventing or slowing the development of diabetes in a mammal by providing a therapeutically effective amount of a protective diabetes-mediating protein; (15) methods for treating diabetes and/or preventing or slowing the development of diabetes in a mammal by providing a therapeutically effective amount of a compound capable of inducing or enhancing the expression of a protective diabetes-mediating protein or of modulating the activity of a diabetes-mediating protein; and (16) methods for treating diabetes and/or preventing or slowing the development of diabetes in a mammal by providing a therapeutically effective amount of a compound capable of inhibiting or reducing the expression of a deleterious diabetes-mediating protein, or of modulating the activity of a diabetes-mediating protein.

I. Diabetes-Mediating Proteins, Polypeptides, Polynucleotides, and Antibodies.

The invention provides diabetes-mediating proteins, that is, proteins identified as involved in or effected during the development of diabetes. Diabetes-mediating proteins are characterized as proteins whose expression is altered during the development of diabetes relative to their expression in the absence of the development of diabetes. The present disclosure identifies diabetes-mediating proteins from a 2-dimensional gel database of pancreatic islet cell proteins. Diabetes-mediating proteins include protective diabetes-mediating proteins and deleterious diabetes-mediating proteins.

The invention provides in vitro methods for identifying diabetes-mediating proteins, including by functionally assessment by expression of cloned cDNA as sense or antisense constructs in transfected cells to establish their deleterious or protective role in cytokine-mediated cytotoxicity. B cells of the islets of Langerhans are specifically sensitive to the toxic effect of cytokines. It has previously been demonstrated that lipofection of rat β cells with heat shock protein 70 (HSP70) and induction of hemeoxygenase (HO) by exposure to hemin improved in vitro survival of cells exposed to IL-1 (Karlsen et al. in: *Insulin Secretion and Pancreatic B Cell Research*, ed: P. R. Flatt and S. Lenzen; Smith-Gordon, USA, pp. 499-507 (1994)). Cells may be transfected in a number of ways known to the art, for example, the adenoviral vector method. See, for example, Korbutt et al. *Transplantation Proceedings* 27:3414 (1995); Csete et al. 26:756-757 (1994); Becker et al. *J. Biol. Chem.* 269:21234-21238 (1994).

Following establishment of stable transfected β cell clones, the effect of the expression of a diabetes-mediating protein may be determined by functional analysis of the clones cultured in the absence and presence of cytokines. The functional analyses include nitrous oxide production (NO) measured as nitrite (Green et al. *Anal. Biochem.* 126:131-138 (1982)), insulin secretion (Id.), cytotoxicity, and 2D-gel electrophoresis. Cytotoxicity may be measured by a variety of methods known to the art, including (1) a calorimetric assay based on lactate dehydrogenase (LDH) release (CytoTox, Promega), (2) a life-death assay based on calcein uptake and fluorescence of living cells and ethidium bromide staining of the nuclei of dead cells (Molecular Probes), (3) non-radioactive cell proliferation assay (MTT, Promega), apoptosis (Nerup et al. in: *IDDM*, S. Baba & T. Kaneko, eds., Elsevier Science, pp. 15-21 (1994)), and/or semiquantitative multiplex PCR analysis of gene expression. 2-dimensional gels can be used to compare control and cytokine stimulated islets to identify which proteins respond, identifying the proteins which play a role in the cell response. Interlink analysis can be used to define functional groups of proteins and their regulation (e.g., by kinase phosphorylation or other post-translational modifications).

Preferred cells for use in the in such an assay are insulin-secreting cells, for example, MSL or RIN cells. The MSL cell line is a pluripotent or stem-cell like metastatic rat insulinoma cell line. Dependent upon culture and/or passage conditions in vitro and in vivo, the MSL cell can acquire all four hormone secretory phenotypes characteristic of the islets of Langerhans (Mandrup-Poulsen et al. *Eur. J. Endocrinology* 133:660-671 (1995); Id. *Eur. J. Endocrinology* 134:21-30 (1996)). RIN cells are a cultured line of insulinoma cells (Nielsen *Exp. Clin. Endocrinol.* 93:277-285 (1989)).

Protective diabetes-mediating proteins. The invention provides substantially purified protective diabetes-mediating proteins ("protective proteins") characterized as capable of protecting against development of diabetes in a subject at risk for the development of the disease or ameliorating or reducing the symptoms of diabetes in a subject suffering from diabetes. The protective protein of the invention may act directly to protect against diabetes, or may act indirectly by inducing or increasing the synthesis of a second protective protein or by reducing or inhibiting the synthesis of a deleterious protein.

In a specific embodiment, the invention provides the substantially pure protective protein galectin-3. The sequence of rat galectin (SEQ ID NO:3) is shown in FIG. 4, and for human galectin (SEQ ID NO:4) in FIG. 5. As shown below, gal-3 expressed in transfected cells increased cell survival upon challenge with IL-1β. Galectins are lectins with specificity for β-galactoside sugars or glycoconjugates which are present in fetal and adult pancreatic islet cells. The term "substantially pure" as used herein refers to gal-3 which is substantially free of other proteins, lipids, carbohydrates or other materials with which it is naturally associated. One skilled in the art can purify gal-3 using standard techniques for protein purification. The purity of the gal-3 polypeptide can also be determined by amino-terminal amino acid sequence analysis. The gal-3 protein includes functional fragments of the polypeptide, as long as the protective activity remains. Smaller peptides containing the biological activity of gal-3 are included in the invention. The invention further includes amino acid sequences having at least 80%, preferably 90%, more preferably 95% identity to the fully length amino acid sequence of SEQ ID NO:4. Percent homology or identity can be determined, for example, by comparing sequence information using the GAP computer program, version 6.0, available from the University of Wisconsin Genetics Computer Group (UWGCG). The GAP program utilizes the alignment method of Needleman and Wunsch *J. Mol. Biol.* 48:443 (1970), as revised by Smith and Waterman *Adv. Appl. Math.* 2:482 (1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess *Nucl. Acids Res.* 14:6745 (1986), as described by Schwartz and Dayhoff, eds. *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps.

The invention also provides purified proteins identified or characterized by a computer system or method of the present invention, where the protein can be selected from the group consisting of
  (a) unaffected proteins having the corresponding molecular weights and pIs as presented in Table 8;
  (b) affected proteins having the corresponding molecular weights and pIs as presented in Table 9; and
  (c) marker proteins having the corresponding molecular weights and pIs as presented in Table 10,
and wherein said at least one of said proteins is optionally further selected from the group consisting of
  (i) unaffected proteins having the corresponding molecular weights and pIs as presented in Table 11;
  (ii) affected proteins having the corresponding molecular weights and pIs as presented in Table 12; and
  (iii) marker proteins having the corresponding molecular weights and pIs as presented in Table 13.

According to the invention, an affected or unaffected peptide includes an association of two or more polypeptide domains, such as transmembrane, cytoplasmic, hydrophobic, hydrophilic, ligand binding, or pore lining domains, or fragments thereof, corresponding to an affected or unaffected peptide, such as 1-40 domains or any range or value therein. Such domains of an affected or unaffected peptide of the invention can have at least 74% homology, such as 74-100% overall homology or identity, or any range or value therein to one or more corresponding affected or unaffected protein or peptide domains as described herein. As would be understood by one of ordinary skill in the art, the above configuration of domains are provided as part of an affected or unaffected peptide of the invention, such that a functional affected or unaffected protein or peptide, when expressed in a suitable cell, is capable of the associated biological activity found in that affected islet cell type. Such activity, as measured by suitable affected or unaffected protein or peptide activity assays, establishes affected or unaffected protein or peptide activity of one or more affected or unaffected proteins or peptides of the invention.

Accordingly, an affected or unaffected peptide of the invention alternatively includes peptides having a portion of an affected or unaffected protein or peptide amino acid sequence which substantially corresponds to at least one 20 to 10,000 amino acid fragment and/or consensus sequence of an affected or unaffected peptide, or group of affected or unaffected peptides, wherein the affected or unaffected protein or peptide has homology or identity of at least 74-99%, such as 88-99% (or any range or value therein, e.g., 87-99, 88-99, 89-99, 90-99, 91-99, 92-99, 93-99, 94-99, 95-99, 96-99, 97-99, or 98-99%) homology or identity to at least one sequence or consensus sequence of at least one protein characterized as presented in one or more of tables 8-13, or as presented in FIGS. 2-7, having the mass spec characteristics of one or more of proteins according to the present invention.

In one aspect, such an affected or unaffected peptide can maintain affected or unaffected protein or peptide biological activity. It is preferred that an affected or unaffected peptide of the invention is not naturally occurring or is naturally occurring but is in a purified or isolated form which does not occur in nature. Preferably, an affected or unaffected peptide of the invention substantially corresponds to any set of domains of an affected or unaffected protein or peptide of the invention, having at least 10 contiguous amino acids of proteins characterized in one or more of tables 8-13, comprising SEQ ID NOS:, having the mass spec characteristics of one or more of proteins according to the present invention.

Alternatively or additionally, an affected or unaffected peptide of the invention can comprise at least one domain corresponding to known protein domains, such as cytoplasmic, intracellular, transmembrane, extracellular, or other known domains, having 74-100% overall homology or any range or value therein. Alternative domains are also encoded by DNA which hybridizes under stringent conditions to at least 30 contiguous nucleotides encoding at least 10 contiguous amino acids of proteins characterized in one or more of tables 8-13, FIGS. 2-7, comprising SEQ ID NOS:, having the mass spec characteristics of one or more of proteins according to the present invention, or at least 74% homology thereto, or having codons substituted therefor which encode the same amino acid as a particular codon. Additionally, phosphorylation (e.g., PKA and PKC) domains, as would be recognized by the those skilled in the art are also considered when providing an affected or unaffected peptide or encoding nucleic acid according to the invention. A non-limiting example of this is presented in proteins 672-674 of table 12, wherein the same protein it differentially phosphorylated.

The invention further includes polynucleotide sequences encoding the diabetes-mediating proteins of the invention, including DNA, cDNA, and RNA sequences. It is also understood that all polynucleotides encoding all or a portion of a diabetes-mediating protein are also included herein, as long as they encode a polypeptide with the diabetes-mediating activity. Such polynucleotides include naturally occurring, synthetic, and intentionally manipulated polynucleotides. For example, such a polynucleotide may be subjected to site-directed mutagenesis. The polynucleotide sequences of the invention also include antisense sequences. Antisense sequences include sequences synthesized with modified oligonucleotides. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of the diabetes-mediating polypeptide is encoded by the nucleotide sequence is functionally unchanged.

The DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the DNA sequences of the invention is derived from a mammalian organism, and most preferably from a human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequences must be known. The DNA sequence encoding the protein can be deduced from the genetic code, however, the degeneracy of the code must be taken into account. The codon bias of the organism can be taken into account to select the most probable nucleotide triplets. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Sambrook et al. *Molecular Cloning: A Laboratory Manual*, 2nd Ed.; Cold Spring Harbor Laboratory Press, Plainview, N.Y. (1989)).

The development of specific DNA sequences encoding the diabetes-mediating proteins of the invention can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double stranded DNA complement of mRNA is eventually formed which is generally referred to as cDNA. Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression for the protein of interest. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al. *Nucl. Acid Res.*, 11 :2325 (1983)).

A cDNA expression library, such as lambda gt11, can be screened indirectly for diabetes-mediating peptides having at least one epitope, using antibodies specific for a diabetes-mediating protein. Such antibodies can be either polyclonally or monoclonally derived and used to detect expression product indicative of the presence of the desired cDNA.

DNA sequences encoding a diabetes-mediating can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the polynucleotide sequences encoding diabetes-mediating proteins may be inserted into a recombinant expression vector. The term "recombinant expression vector" refers to a plasmid, virus or other vehicle known in the art that has been manipulated by insertion or incorporation of the X130 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al. *Gene* 56:125 (1987)), the pMSXND expression vector for expression in mammalian cells (Lee and Nathans *J. Biol. Chem.* 263:3521 (1988)) and baculovirus-derived vectors for expression in insect cells. The DNA segment can be present in the vector operably linked to regulatory elements, for example, a promoter (e.g., T7, metallothionein I, or polyhedron promoters).

Polynucleotide sequences encoding a diabetes-mediating protein can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the diabetes-mediating protein of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to infect, transform, or transduce eukaryotic cells and express the protein (see, for example, *Eukaryotic Viral Vectors*, Cold Spring Harbor Laboratory, Gluzman ea., 1982).

Isolation and purification of microbial expressed polypeptide, or fragments thereof, provided by the invention, may be carried out by conventional means including preparative chromatography and immunological separations involving monoclonal or polyclonal antibodies. 2DGE is a preferred method for purification of modifications variants of the proteins from each other.

Deleterious diabetes-mediating proteins. Deleterious diabetes-mediating proteins ("deleterious proteins") are characterized as enhancing the development of or increasing the risk of a subject developing diabetes. The invention includes substantially purified protective diabetes-mediating proteins, and polynucleotide sequences encoding such proteins. In a preferred embodiment, a deleterious protein is mortalin. The amino acid sequence of murine mortalin (SEQ ID NO:1) is shown in FIG. 2, and of human mortalin (SEQ ID NO:2) in FIG. 3.

Antibodies specific to diabetes-mediating proteins. The diabetes-mediating proteins of the invention can also be used to produce antibodies which are immunoreactive or bind to epitopes of the diabetes mediating proteins. An antibody may consist essentially of pooled monoclonal antibodies with different epitopic specificities, as well as distinct monoclonal antibody preparations. Monoclonal antibodies are made from antigen containing fragments of the protein by methods well known in the art (Kohler et al. *Nature* 256:495 (1975); Current Protocols in Molecular Biology, Ausubel et al., ca., 1989).

The term "antibody" as used in this invention includes intact molecules as well as fragments thereof, such as Fab, F(ab')2, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab')2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. See, for example, Harlow and Lane, *Antibodies: A Laboratory Manual*, Cold Spring Harbor Laboratory, New York (1988), incorporated herein by reference.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the diabetes-mediating polypeptides of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elusion from a matrix to which the polypeptide or a peptide to which the antibodies were raised is bound. Those of skill in the art will know of various techniques common in the immunology arts for purification and/or concentration of polyclonal antibodies, as well as monoclonal antibodies. See, for example, Coligan et al. Unit 9, *Current Protocols in Immunology*, Wiley Interscience (1994), herein specifically incorporated by reference.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

For purposes of the invention, an antibody or nucleic acid probe specific for a diabetes-mediating protein may be used to detect the diabetes-mediating protein (using antibody) or encoding polynucleotide (using nucleic acid probe) in biological fluids or tissues. The antibody reactive with the diabetes-mediating protein or the nucleic acid probe is preferably labeled with a compound which allows detection of binding to the diabetes-mediating protein. Any specimen containing a detectable amount of antigen or polynucleotide can be used. Further, specific proteins may be selected by their ligands, e.g., galectin-3 binding to lectin-binding protein), and is useful for diagnosis and/or purification of the protein of interest.

When the cell component is nucleic acid, it may be necessary to amplify the nucleic acid prior to binding with a diabetes-mediating protein-specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

II. Method for Identifying a Diabetes-Mediating Protein

In vivo animal transplantation model. The invention features a method for identifying a diabetes-mediating protein, by providing an in vivo assay system which detects proteins which are involved in the development of diabetes or which are specifically effected during development of diabetes. The in vivo transplantation assay of the invention described herein allows the identification of proteins involved or effected.

In the method for identifying a diabetes-mediating protein of the invention, insulin-secreting cells or cells capable of developing into insulin-secreting cells are transplanted into a host animal. Transplanted cells are rescued at time points between transplantation and the onset of diabetes, and protein expression determined, and protein expression compared with non-transplanted islets and syngeneic transplants in animals not developing diabetes. The method of the invention allows proteins exhibiting an altered expression during development of diabetes to be identified. Identified proteins are then isolated and tested further to identification as protective or deleterious diabetes-mediating proteins.

Cells capable of developing into insulin-producing cells include pancreatic islet cells and β cells. Transplanted cells may be obtained from any species of interest, including human cells. A host animal is preferably one which is immunologically compatible with the transplanted cells such that the transplanted cells do not undergo rejection in the host animal.

The host animal may be any animal which develops diabetes and is convenient for study. Preferred host animals are mice, rats and hamsters, with rats and mice being most preferred. In particularly preferred embodiments, the host animal is selected from a strain bred for an increased incidence of diabetes, including BB-DP rats and NOD mice. The method of the invention may also be used with host animals engineered to develop diabetes at a predetermined time, e.g., upon exposure to a specific antigen. See, for example, Oldstone et al. *APMIS* 104:689-97 (1996); von Herrath et al. *J. Clin. Invest.* 98:1324-1331 (1996); Morgan et al. *J. Immunol.* 157: 978983 (1996). Other possible host animals include those belonging to a genus selected from *Mus* (e.g. mice), *Rattus* (e.g. rats), *Oryctolagus* (e.g. rabbits), and *Mesocricetus* (e.g. hamsters) and *Cavia* (e.g., guinea pigs). In general mammals with a normal full grown adult body weight of less than 1 kg which are easy to breed and maintain can be used.

Method of determining protein expression. Protein expression may be assessed by a variety of means known to the art, including one or two-dimensional gel electrophoresis and immunoblotting.

Two-dimensional gel electrophoresis (2-DGE) is a particularly effective tool for separating mixtures of proteins (Andersen et al. *Diabetes* 44:400-407 (1995)). Cell protein extracts are put onto a gel, and the individual proteins are separated first by charge and then by size. The result is a characteristic picture of as many as 1,000 to 5,000 spots, each usually a single protein. Resolution is improved by increasing gel size, and by enhancing the sensitivity trough the use of radiolabel methods, silver staining, and the reduction in thickness of the gels to 1.5 mm and less.

Method for isolating diabetes-mediating proteins. As described in the Examples below, single proteins recovered from 2D gels can be identified by mass spectrometry to obtain a trypsin cleavage pattern as well as the precise molecular weight of each peptide. These observed values are then used to search in DNA and protein databases to determine if matches exist to previously identified proteins. Identity can be determined from a known protein or deduced from high homology to a known protein. When 2D gel electrophoresis is used to separate and identify protein spots which exhibit an altered synthesis during development of diabetes, an identified protein spot is excised from the gel and digested with trypsin to produce peptides. The peptides are recovered from the gel and subjected to mass spectroscopy (matrix assisted laser desorption/ionization mass spectrometry) (MALDI) and the resulting MS-profiles are analyzed against the computerized MS-profiles of all sequences found in the public sequence databases, as well as against propriety sequence information. If any matches to previously cloned sequences are obtained, information about the corresponding gene and encoded protein is collected. When an identified diabetes-mediating protein does not match a previously cloned protein, the protein may be microsequenced to obtain partial amino acid sequence information by methods known to the art (see Example 5 below). Based upon results obtained from database searches or amino acid sequencing, specific or degenerate primers are constructed and used to screen rat and human islets libraries or first-strand cDNA by PCR is used to clone partial sequences of the corresponding cDNA. The obtained sequences are then used to obtain full-length coding regions either by 5'-race PCR or by conventional hybridization screening techniques, followed by expression of the recombinant protein (Kalsen et al. *Proc. Natl. Acad. Sci. USA* 88:8337-8341 (1991); Karlsen et al. in: *Insulin secretion and pancreatic B-cell research*, Flatt, P. R., ea., Smith-Gordon, USA; Chapter 64, pp. 1-9 (1994); Kartsen et al. *Diabetes* 44:757-758 (1995).

Diabetes-mediating proteins can be isolated in a variety of ways known to the art, including purification from biological material, expression from recombinant DNA (see above). Conventional method steps include extraction, precipitation, chromatography, affinity chromatography, and electrophoresis. For example, cells expressing a diabetes-mediating protein can be collected by centrifugation, or with suitable buffers, lysed, and the protein isolated by column chromatography, for example, on DEAE-cellulose (diethylaminoethylcellulose), phosphocellulose, polyribocytidylic acid-agarose, hydroxyapatite or by electrophoresis or immunoprecipitation. Diabetes-mediating proteins may alternatively be isolated by immunoprecipitation with the use of specific antibodies.

III. Transgenic Animals Expressing a Diabetes-Mediating Protein Transgene.

In one aspect, the invention includes a transgenic animal containing a gene encoding a diabetes-mediating protein, as well as transgenic animals which are the offspring of a transgenic animal of the invention. The gene encoding a diabetes-mediating protein may be comprised of a naturally occurring or partially or completely of an artificial polynucleotide sequence, i.e. codon sequences not present in the native gene sequence. Transgenic animals containing elevated levels of expression of the diabetes-mediating gene of the invention can be obtained for example, by over-expression of the gene with an enhanced promoter and/or with high copy numbers of the natural gene. Transgenic animals also specifically include a hybrid transgenic animal produced by crossing a transgenic animal with an animal in which one or more diabetes-mediating protein gene(s) are ablated.

Transgenic animals of the invention are useful in a number of ways, including in assays for determining the effect of a candidate protective or deleterious diabetes-mediating protein on the development of diabetes. For example, a transgenic animal carrying a transgene for a candidate protective protein is useful for determining the effect of the expression of the protective transgene on the development of diabetes.

Preferred host animals are mice, rats and hamsters, with rats and mice being most preferred in that there exists considerable knowledge on the production of transgenic animals. Other possible host animals include those belonging to a genus selected from *Mus* (e.g. mice), *Rattus* (e.g. rats), *Oryctolagus* (e.g. rabbits), and *Mesocricetus* (e.g. hamsters) and *Cavia* (e.g., guinea pigs). In general mammals with a normal full grown adult body weight of less than 1 kg which are easy to breed and maintain can be used.

The transgenic non-human mammal of the invention (preferably a rat or mouse) will have in some or all of its nucleated cells a gene encoding a diabetes-mediating protein, e.g., one or more of a protection protein or deleterious protein, which gene was introduced into the mammal, or an ancestor of that mammal, at an embryonic or germ cell stage. This "embryonic stage" may be any point from the moment of conception (e.g., as where the sperm or egg bears the foreign gene) throughout all of the stages of embryonic development of the fetus. A "transgenic mammal" as used herein denotes a mammal bearing in some or all of its nucleated cells one or more genes derived from the same or a different species; if the cells bearing the foreign gene include cells of the animal's germline, the gene may be transmissible to the animal's offspring.

Genetics constructs and methodologies of the invention may be used to create animals which due to their genetic make up will develop diabetes and will exhibit symptoms of the disease in a predictable period of time. In a preferred embodiment, the transgenic mammal of the invention exhibits a 80% incidence of diabetes within 70±10 days; more preferably, a 90% incidence of diabetes within 60±5 days; most preferably, a 95% incidence of diabetes within 55±5 days; and even more preferably, a 97% incidence of diabetes within 50±5 days. The animals of the invention are used in assays to test the ability of a candidate protective or deleterious diabetes-mediating protein, or a test compound to prevent, enhance, or slow the development of diabetes.

In one aspect of the invention, genetic constructs and methodologies of the invention are used to create animals having a transgene encoding a candidate protective or deleterious protein. Transgenic animals may be selected from a genetic background predisposed for development of diabetes, or may be double-transgenic animals which will develop diabetes predictable and in a short period of time. In this embodiment of the invention, the animals are used in assays to test the ability of the candidate protective protein to inhibit or reduce the incidence of disease onset. In a related aspect, the animals are used in assays to test the ability of a compound to induce expression of a protective protein and thus to protect the animal from disease development.

In one aspect of the invention, genetics constructs and methodologies of the invention are used to create animals which due to their genetic make up will develop diabetes within a predictable period of time. For example, in one embodiment, transgenic animals are created which express a deleterious diabetes-mediated disease such as mortalin. The animals of the invention are used in assays to test compounds able to prevent or delay the onset of diabetes. In one embodiment, it is preferable to include a deleterious protein gene within the transgenic animal in a relatively high copy number, in that increasing the copy number tends to decrease the time required for disease onset.

Further, adjustments can be made with respect to the use of specific types of enhanced promoters in order to elevate the levels of expression without increasing copy numbers. Specific types of enhanced promoters are known which would provide enhanced expression to the diabetes-mediating protein transgene without increased copy numbers. The enhanced promoters may operate constitutively or inducibly.

The invention also provides a means of creating animal models for diabetes or diabetes related diseases. The transgenic animals of the invention provide a way to develop and test potential therapies for the diabetes, and will eventually lead to cures for this disease.

IV. Assays for Screening for Drugs Capable of Effecting the Expression of Diabetes-Mediating Proteins.

Assay methods provided by the invention are useful for screen compounds capable of effecting the expression of a diabetes-mediating protein, and thus the development of diabetes in a mammal. One model for screening drugs capable of effecting the expression of one or more diabetes-mediating proteins is the administration of compounds suspected of having beneficial effects (including antisense oligonucleotides) to cells in culture. Useful cells are RIN, transfected, or islet cells. The effects of the test compound on protein expression may then be assayed by 2D gel electrophoresis.

Another screening model is an in vivo method with the use of a mammal at risk for development of diabetes. Briefly, a mammal with an increased risk for diabetes (e.g., diabetes-prone BB rat or NOD mouse) is exposed to a test compound, and the effect of exposure to the test compound on the development of diabetes determined.

The development of diabetes may be monitored throughout the developmental period by determining the expression of one or more diabetes-mediating. proteins and comparing the time of disease onset with expression and timing in the absence of disease development. Determining the expression of one or more diabetes-mediating proteins includes the diabetes-mediating protein itself, a post-translational modification product, and/or diabetes-mediating protein degradation product. In one embodiment, activation of a diabetes-mediating protein is determined by measuring the level of the diabetes-mediating protein expression in a test sample. A suitable test sample includes a body fluid, such as blood, urine, or cerebrospinal fluid, or fluid derived from it, such as plasma or serum. In a specific embodiment, the level of protein expression in a test sample is measured by Western blot analysis. The proteins present in a sample are fractionated by gel electrophoresis, transferred to a membrane, and probed with labeled antibodies specific for the protein(s). In another specific embodiment, the level of diabetes-mediating protein expression is measured by Northern blot analysis. Polyadenylated [poly(A)$^+$] mRNA is isolated from a test sample. The mRNA is fractionated by electrophoresis and transferred to a membrane. The membrane is probed with labeled cDNA. In another embodiment, protein expression is measured by quantitative PCR applied to expressed mRNA.

In a more specific embodiment, a mammal capable of developing diabetes is one selected from a strain of mammals which have been bred for an increased incidence of diabetes. Preferable, the mammal is selected from a strain which exhibits a 75% chance of developing diabetes within 69±25 days. More preferably, the mammal is a transgenic mammal of engineered to exhibit a high incidence of diabetes within a predictable period of time. In specific embodiments, the transgenic mammal exhibits a 80% incidence of diabetes within 70±10 days; more preferably, a 90% incidence of diabetes within 60±5 days; most preferably, a 95% incidence of diabetes within 55±5 days; and even more preferably, a 97% incidence of diabetes within 50±5 days.

In yet another aspect, the invention provides for methods for identifying compounds capable of suppressing or reducing the expression of an endogenous deleterious protein, as well as methods for preventing and/or treating diabetes by administering a therapeutically effective among of a compound capable of suppressing or reducing the expression of an endogenous deleterious protein.

The diabetes-mediating proteins of the invention are also useful to screen reagents that modulate diabetes-mediating protein activity. Accordingly, in one aspect, the invention features methods for identifying a reagent which modulates diabetes-mediating protein activity, by incubating a cell expressing a diabetes mediating protein with the test reagent and measuring the effect of the test reagent on diabetes mediating protein synthesis, phosphorylation, function, or activity. When activation of a diabetes-mediating protein is via phosphorylation, the test reagent is incubated with the diabetes-mediating protein and with either gamma- [labeled-ATP or [$^{35}$S]-methionine, and the rate of phosphorylation determined. In another embodiment, the test reagent is incubated with a cell transfected with a diabetes-mediating protein polynucleotide expression vector, and the effect of the test reagent on diabetes-mediating protein transcription is measured by Northern blot analysis. In a further embodiment, the effect of the test reagent on diabetes-mediating protein synthesis is measured by Western blot analysis using an antibody to the diabetes-mediating protein. In still another embodiment, the effect of a reagent on diabetes-mediating protein activity is measured by incubating diabetes-mediating protein with the test reagent, [$^{32}$P]-ATP, and a substrate in the diabetes-mediating protein pathway. All experiments would be compared against a normal labeling of cells with [$^{35}$S]-methionine to determine modulation of protein expression. The rate of substrate phosphorylation is determined by methods known in the art.

The term modulation of diabetes-mediating protein activity includes agonists and antagonists. The invention is particularly useful for screening reagents that inhibit deleterious protein activity. Such reagents are useful for the treatment or prevention of diabetes.

V. Therapeutic Applications

The invention provides methods for preventing and/or treating diabetes in a mammal by administering a therapeutically effective amount of a protective diabetes-mediating protein. Preferably the mammal is a human subject at risk for diabetes.

Drug screening using identified diabetes-mediating proteins and related diabetes therapeutic agents. In a drug-screening assay of the invention, identified protective or deleterious diabetes-mediating proteins are used to identify test compounds capable of effecting their expression. Test compounds so identified are candidate therapeutic agents for preventing, ameliorating, or delaying the onset of diabetes in a subject at risk.

A test therapeutic compound which effects the expression of a diabetes-mediating proteins can be, but is not limited to, at least one selected from a nucleic acid, a compound, a protein, an element, a lipid, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies, as described herein. Such labels include, but are not limited to, enzymatic labels, radioisotope or radioactive compounds or elements, fluorescent compounds or metals, chemiluminescent compounds and bioluminescent compounds.

A therapeutic compound is identified in the drug screening assay of the invention through its ability to induce or enhance the expression of a protective protein, such that disease onset is prevented or delayed in a subject at risk for the development of diabetes. A candidate therapeutic compound is also identified by its ability to prevent or decrease the expression of a deleterious protein, such that disease onset is prevented or delayed in a subject at risk for the development of diabetes.

A therapeutic nucleic acid as a therapeutic compound can have, but is not limited to, at least one of the following therapeutic effects on a target cell: inhibiting transcription of a deleterious protein DNA sequence; inhibiting translation of a deleterious protein RNA sequence; inhibiting reverse transcription of an RNA or DNA sequence corresponding to a deleterious protein; inhibiting a post-translational modification of a protein; inducing transcription of a DNA sequence corresponding to a protective protein; inducing translation of an RNA sequence corresponding to a protective protein; inducing reverse transcription of an RNA or DNA sequence corresponding to a protective protein; translation of the nucleic acid as a protein or enzyme; and incorporating the nucleic acid into a chromosome of a target cell for constitutive or transient expression of the therapeutic nucleic acid.

Therapeutic effects of therapeutic nucleic acids can include, but are not limited to: turning off a defective gene or processing the expression thereof, such as antisense RNA or DNA; inhibiting viral replication or synthesis; gene therapy as expressing a heterologous nucleic acid encoding a therapeutic protein or correcting a defective protein; modifying a defective or underexpression of an RNA such as an hnRNA, an mRNA, a tRNA, or an rRNA; encoding a drug or prodrug, or an enzyme that generates a compound as a drug or prodrug in pathological or normal cells expressing the diabetes-mediating protein or peptide; and any other known therapeutic effects.

Also included in the invention is gene therapy by providing a polynucleotide encoding a protective diabetes-mediating protein.

The invention further includes a method for preventing diabetes by administering an effective amount of a polynucleotide which inhibits the in vivo expression of a deleterious diabetes-mediating protein.

In the therapeutic method of the invention, a therapeutic compound is administered to a human patient chronically or acutely. Optionally, a protective protein is administered chronically in combination with an effective amount of a compound that acts on a different pathway than the therapeutic compound. The therapeutic method of the invention can be combined with other treatments for diabetes or with methods for the management of diabetes.

Therapeutic formulations of the therapeutic compound for treating or preventing diabetes are prepared for storage by mixing the compound having the desired degree of purity with optional physiologically acceptable carriers, excipients, or stabilizers (*Remington's Pharmaceutical Sciences*, 16th edition, Oslo, A., Ed., 1980), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutarine, aspargine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or non-ionic surfactants such as Tween, Pluronics, or polyethylene glycol (PEG). The compound is also suitably linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337. The amount of carrier used in a formulation may range from about 1 to 99%, preferably from about 80 to 99%, optimally between 90 and 99% by weight.

The therapeutic compound to be used for in vivo administration must be sterile. This is readily accomplished by methods known in the art, for example, by filtration through sterile filtration membranes, prior to or following lyophilization and reconstitution. The therapeutic compound ordinarily will be stored in lyophilized form or in solution.

Therapeutic compositions generally are placed into a container having a sterile access port, for example, an intravenous solution bag or vial having a stopper pierce-able by a hypodermic injection needle.

The therapeutic compound administration is in a chronic fashion using, for example, one of the following routes: injection or infusion by intravenous, intraperitoneal, intracerebral, intramuscular, intraocular, intraarterial, or intralesional routes, orally or using sustained-release systems as noted below. The therapeutic compound is administered continuously by infusion or by periodic bolus injection if the clearance rate is sufficiently slow, or by administration into the blood stream or lymph The preferred administration mode is targeted to the tissue of interest (β cell or pancreatic cells) so as to direct the molecule to the source and minimize side effects of the compound.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al. *J. Biomed. Mater. Res.* 15:167-277 (1981) and *Langer Chem. Tech.* 12:98-105 (1982), or poly(vinyl alcohol)), polylactides (U.S. Pat. No. 3,773,919, EP 58,481), copolymers of L-glutamic acid and gamma ethyl-L-glutamate (Sidman et al. *Biopolymers* 22:547-556 (1983)), non-degradable ethylene-vinyl acetate (Larger et al. supra (1981)), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid (EP 133,988).

The therapeutic compound also may be entrapped in microcapsules prepared, for example, by coacervation techniques or by interracial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nanoparticles and nanocapsules), or in macroemulsions. Such techniques are disclosed in *Remington's Pharmaceutical Sciences*, supra.

While polymers such as ethylene-vinyl acetate and lactic acid-glycolic acid enable release of molecules for over 100 days, certain hydrogels release molecules for shorter time periods. When encapsulated molecules remain in the body for a long time, they may denature or aggregate as a result of exposure to moisture at 37° C., resulting in a loss of biological activity and possible changes in immunogenicity. Rational strategies can be devised for stabilization depending on the mechanism involved, e.g., using appropriate additives, and developing specific polymer matrix compositions.

Sustained-release compositions also include liposomally entrapped therapeutic compound(s). Liposomes containing therapeutic compound(s) are prepared by methods known per se: DE 3,218,121; Epstein et al. *Proc. Natl. Acad. Sci. USA* 82:3688-3692 (1985); Hwang et al. *Proc. Natl. Acad. Sci. USA* 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol % cholesterol, the selected proportion being adjusted for the optimal agonist therapy. A specific example of a suitable sustained-release formulation is in EP 647,449.

An effective amount of therapeutic compound(s) to be employed therapeutically will depend, for example, upon the therapeutic objectives, the route of administration, and the condition of the patient. Accordingly, it will be necessary for the clinician to titer the dosage and modify the route of administration as required to obtain the optimal therapeutic effect.

If two therapeutic compounds are administered together, they need not be administered by the same route, nor in the same formulation. However, they can be combined into one formulation as desired. Both therapeutic compounds can be administered to the patient, each in effective amounts, or each in amounts that are sub-optimal but when combined are effective. In one embodiment, the administration of both therapeutic compounds is by injection using, e.g., intravenous or subcutaneous means, depending on the type of protein employed. Typically, the clinician will administer the therapeutic compound(s) until a dosage is reached that achieves the desired effect for treatment or prevention of diabetes. For example, the amount would be one which ameliorates symptoms of diabetes and restores normoglycemia. The progress of this therapy is easily monitored by conventional assays.

In specific embodiments of this aspect of the invention, the therapeutic compound is a protective diabetes-mediating gene encodes gal-3, and/or a post-translational modification product of gal-3. A typical daily dosage of a therapeutic compound used alone might range from about 1 μg/kg to up to 100 mg/kg of patient body weight or more per day, depending on the factors mentioned above, preferably about 10 μg/kg/day to 50 mg/kg/day.

Gene therapy. The present invention also provides gene therapy for the treatment of diabetes and diabetes-related disorders, which are improved or ameliorated by a protective polypeptide. Such therapy would achieve its therapeutic effect by introduction of the protective polynucleotide into insulin-producing cells. Delivery of a protective polynucleotide can be achieved using a recombinant expression vector such as a chimeric virus or a colloidal dispersion system. Especially preferred for therapeutic delivery of sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector for in vitro cell transformation is a derivative of a murine or avian retrovirus adenovirus. The advantage of adenovirus transduction compared to other transfection methods is the high transfection affectivity and the ability to transfect whole islets. Furthermore, the level of expression can be adjusted by the virus concentration and transduction-time used. Even though the adenovirus-mediated expression is transient, the expression in islets is stable for at least several weeks (Becker et al. *J. Biol. Chem.* 269:21234 (1994); Korbutt et al. *Transplantation Proc.* 27:3414 (1995)).

For stable integration of a transgene into a mammal, a retroviral vector is preferred. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a diabetes-mediating protein sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the protective polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfect with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for protective polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LW), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form (Fraley, et al. *Trends Biochem. Sci.* 6:77 (1981)). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Manning et al. *Biotechniques* 6:682 (1988)).

The composition of the liposome is usually a combination of phospholipids, particularly high-phase-transition-temperature phospholipids, usually in combination with sterols, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidyl-glycerol, phosphatidylcholine, phosphatidylserine, phosphatidylethanolamine, sphingolipid, cerebrosides, and gangliosides. Particularly useful are diacylphosphatidyl-glycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the biological activity of therapeutic compounds in enhancing synthesis of secondary therapeutic compounds, there are a variety of applications using the polypeptide or polynucleotide of the invention, including application to disorders related to the expression of such secondary proteins.

The invention provides methods for treatment of diabetes and diabetes-related disorders, which are improved or ameliorated by modulation of deleterious diabetes-mediating gene expression or activity. In one specific embodiment of this aspect of the invention, the deleterious diabetes-mediating gene encodes mortalin. The term "modulate" envisions the suppression of expression of mortalin.

Where suppression of a deleterious protein expression is desirable, for example, suppression of mortalin, nucleic acid sequences that interfere with mortalin expression at the translational level can be used. This approach utilities, for example, antisense nucleic acid, ribozymes, or triplex agents to block transcription or translation of a specific mortalin mRNA, either by masking that mRNA with an antisense nucleic acid or triplex agent, or by cleaving it with a ribozyme.

Antisense nucleic acids are DNA or RNA molecules that are complementary to at least a portion of a specific mRNA molecule (Weintraub *Scientific American* 262:40 (1990)). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target mortalin-producing cell.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher et al. *Antisense Res. and Dev.* 1:227 (1991); Helene *Anticancer Drug Design,* 6:569 (1991)).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech *J. Amer. Med. Assn.* 260:3030(1988). A major advantage of this approach is that, because they are sequence-specific, only mRNAs with particular sequences are inactivated.

There are two basic types of ribozymes namely, tetrahymena-type (Hasselhoff *Nature* 334:585 (1988)) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Blocking mortalin action either with anti-mortalin antibodies or with a mortalin antisense polynucleotide may be useful for slowing or ameliorating diabetes. The above described method for delivering a protective polynucleotide are fully applicable to delivery of an mortalin antagonist for specific blocking of mortalin expression and/or activity when desirable. A mortalin antagonist can be a mortalin antibody, an antisense polynucleotide sequence, or a compound which suppresses or inhibits the expression of mortalin.

Identification and Characterization of Diabetes-Mediating Proteins

Figure 1B:
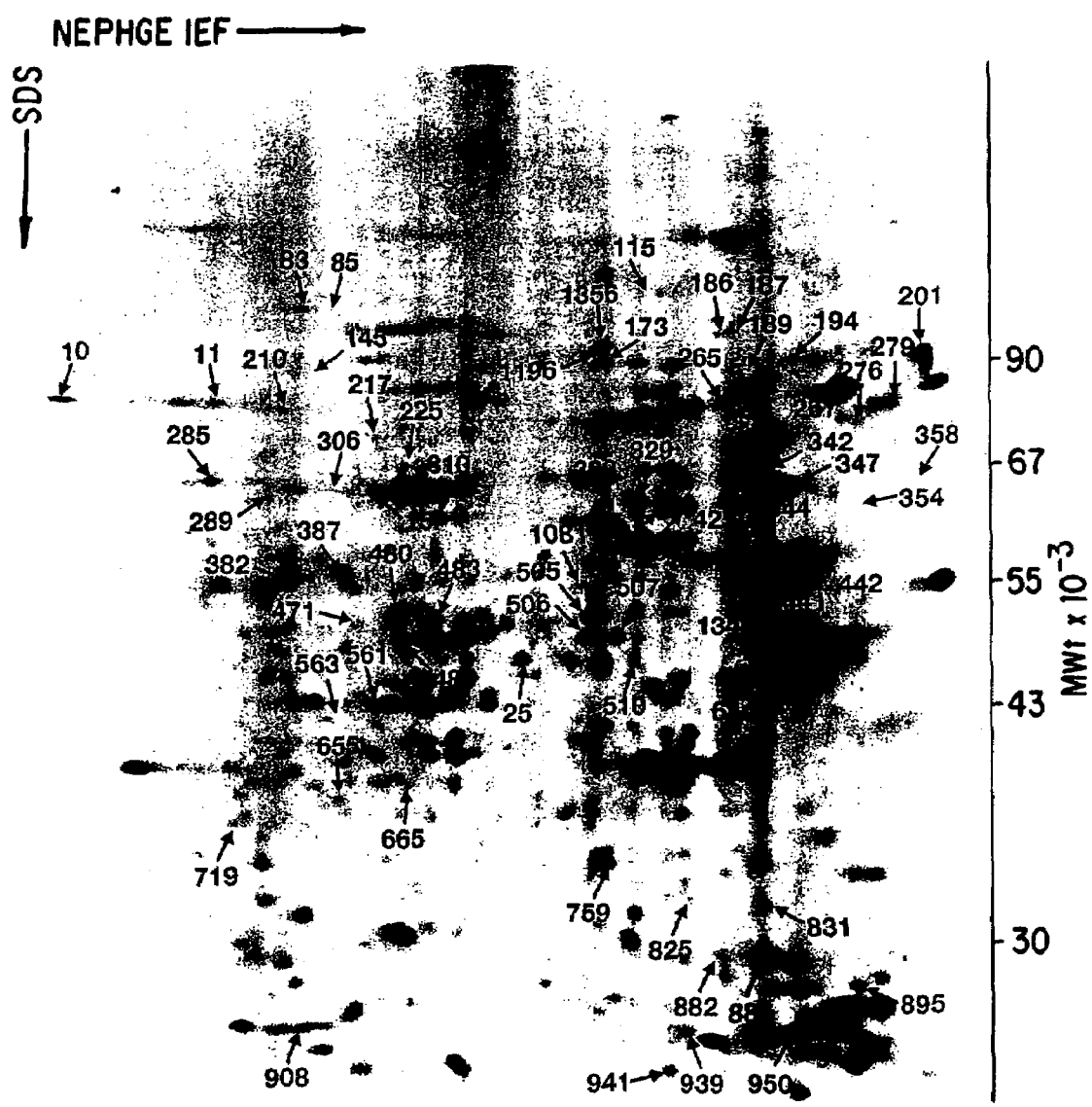
Figure 6:
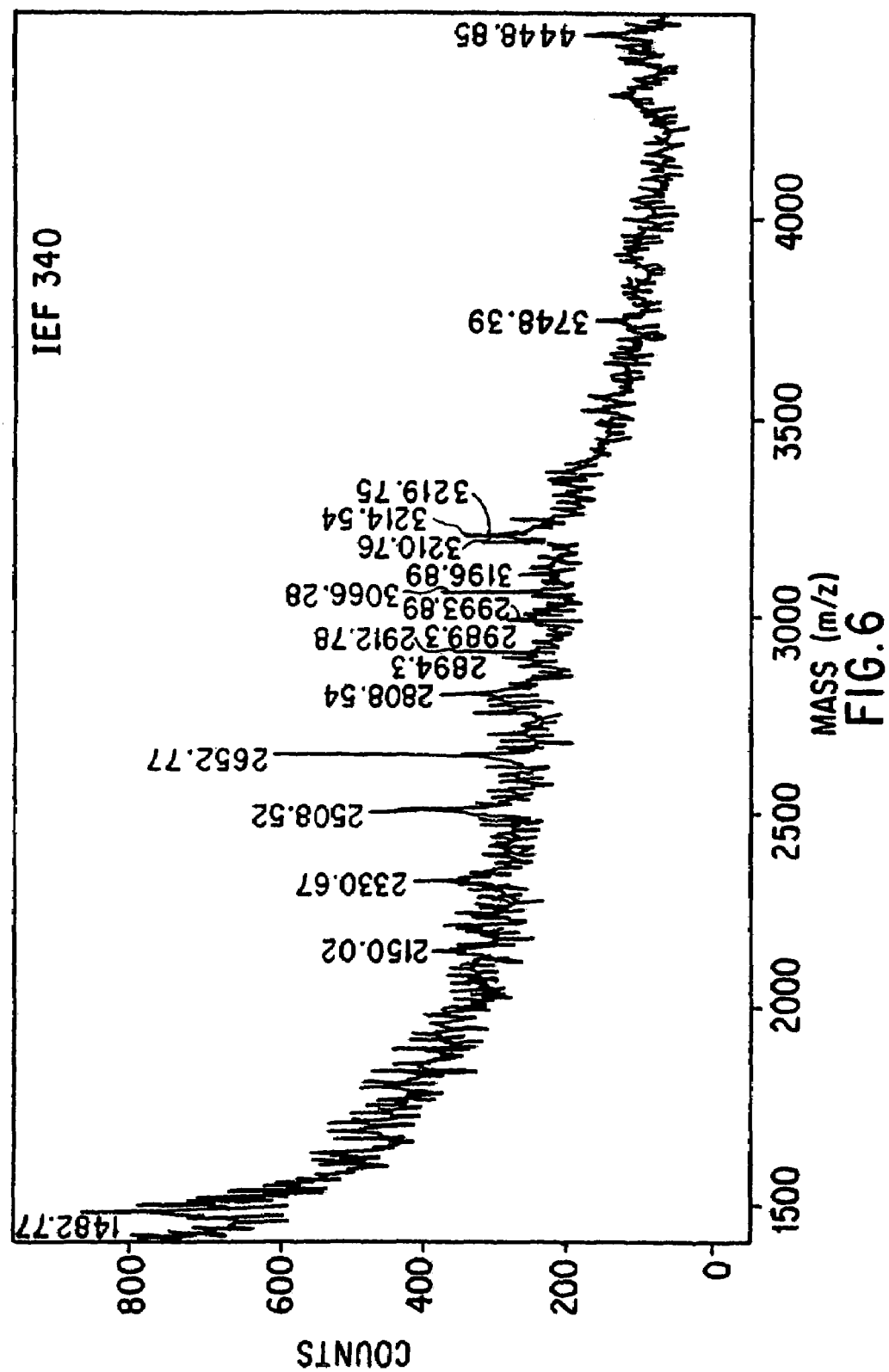
FIG. 6 is the mass spectroscopy spectrum for diabetes-mediating protein GR75 (mortalin), IEF Spot No. 340, determined using the parameters indicated on the figure legend.
Figure 7:
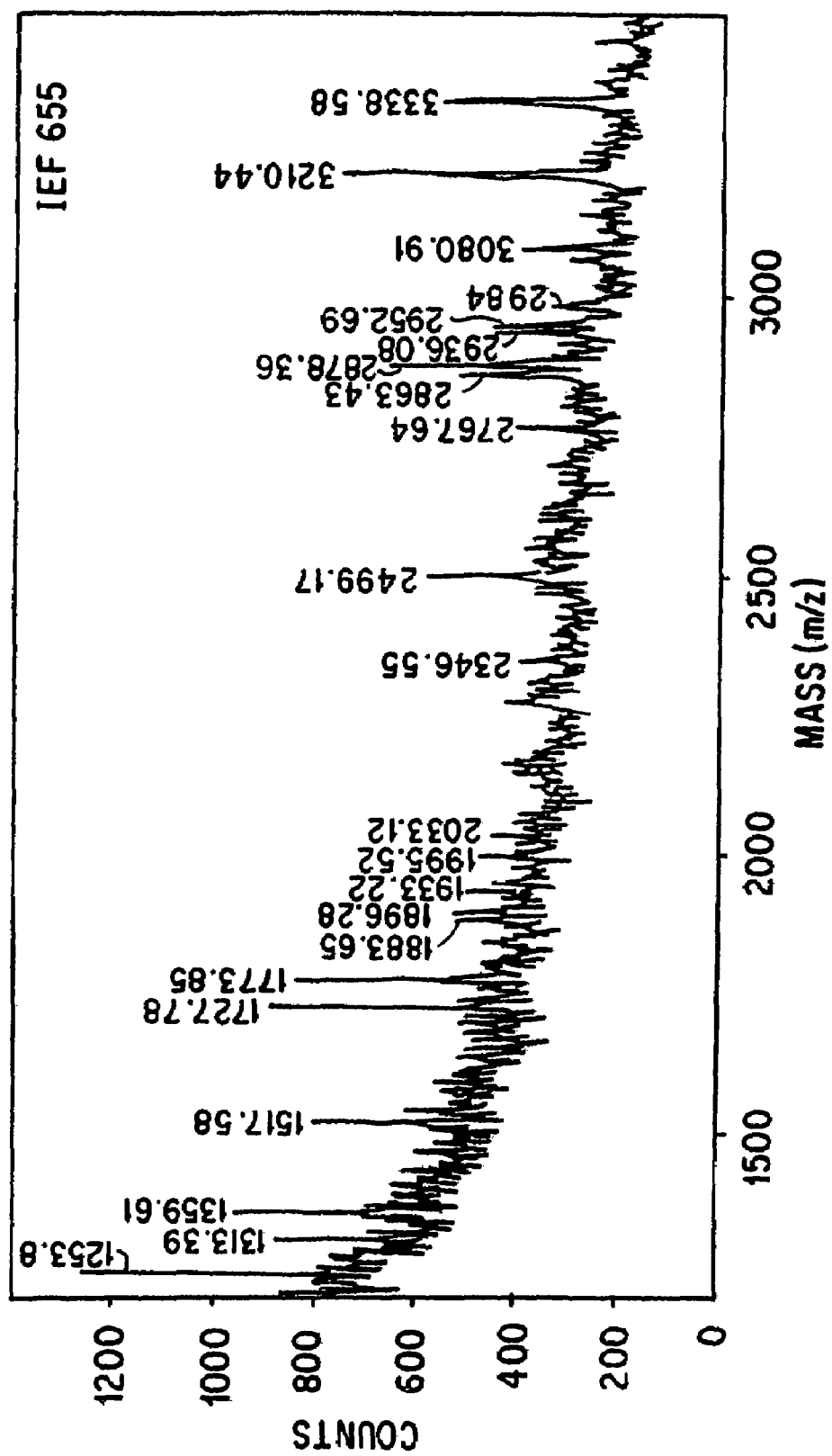
FIG. 7 is the mass spectroscopy spectrum for diabetes-mediating protein, tentatively identified as lamin a, IEF Spot No. 655, determined as indicated.
Figure 8:
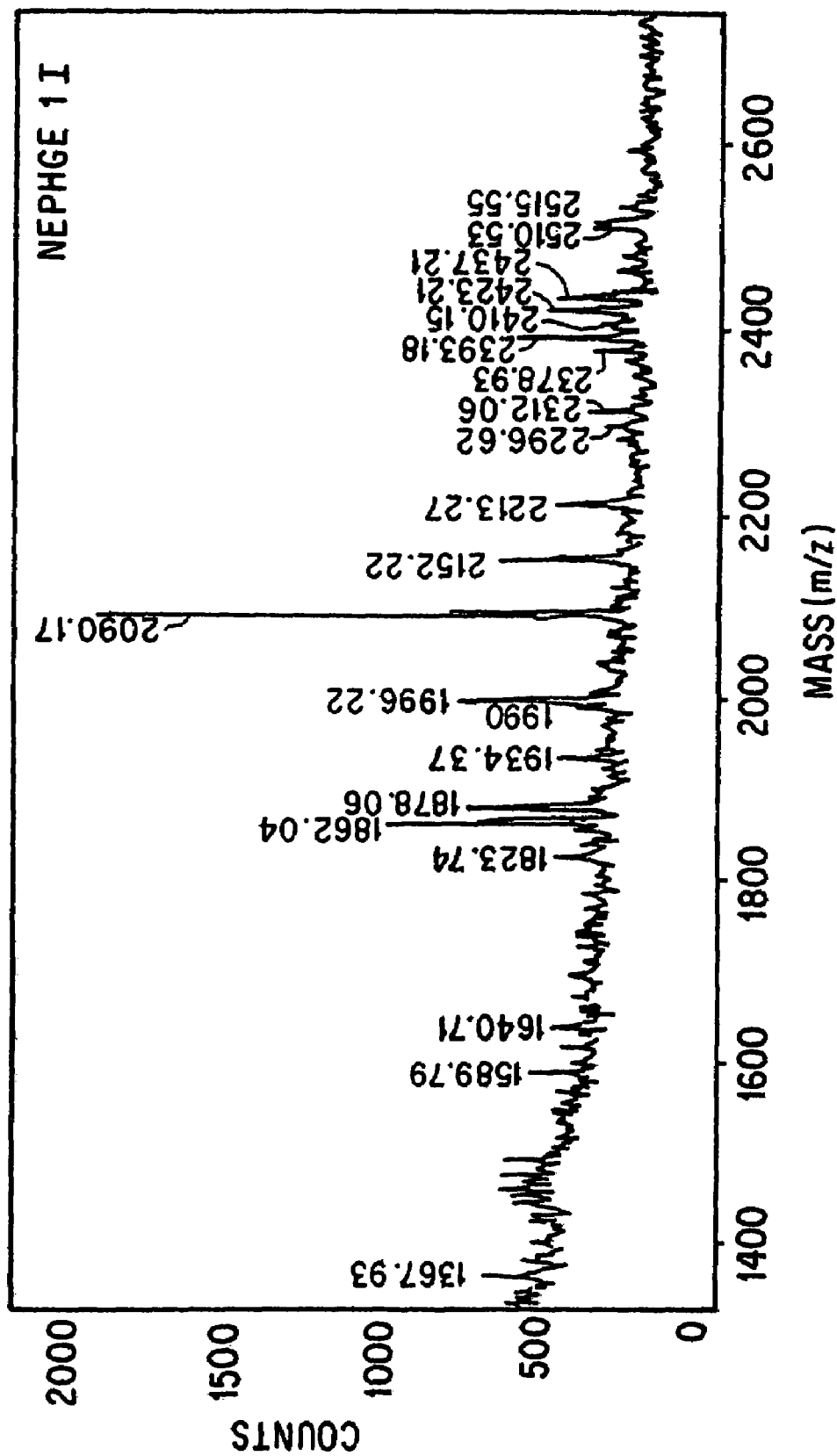
FIGS. 8-10 are the mass spectroscopy spectrum for a diabetes-mediating, tentatively identified as pyruvate kinase, NEPHGE Spot No. 1, determined as indicated.
Figure 9:
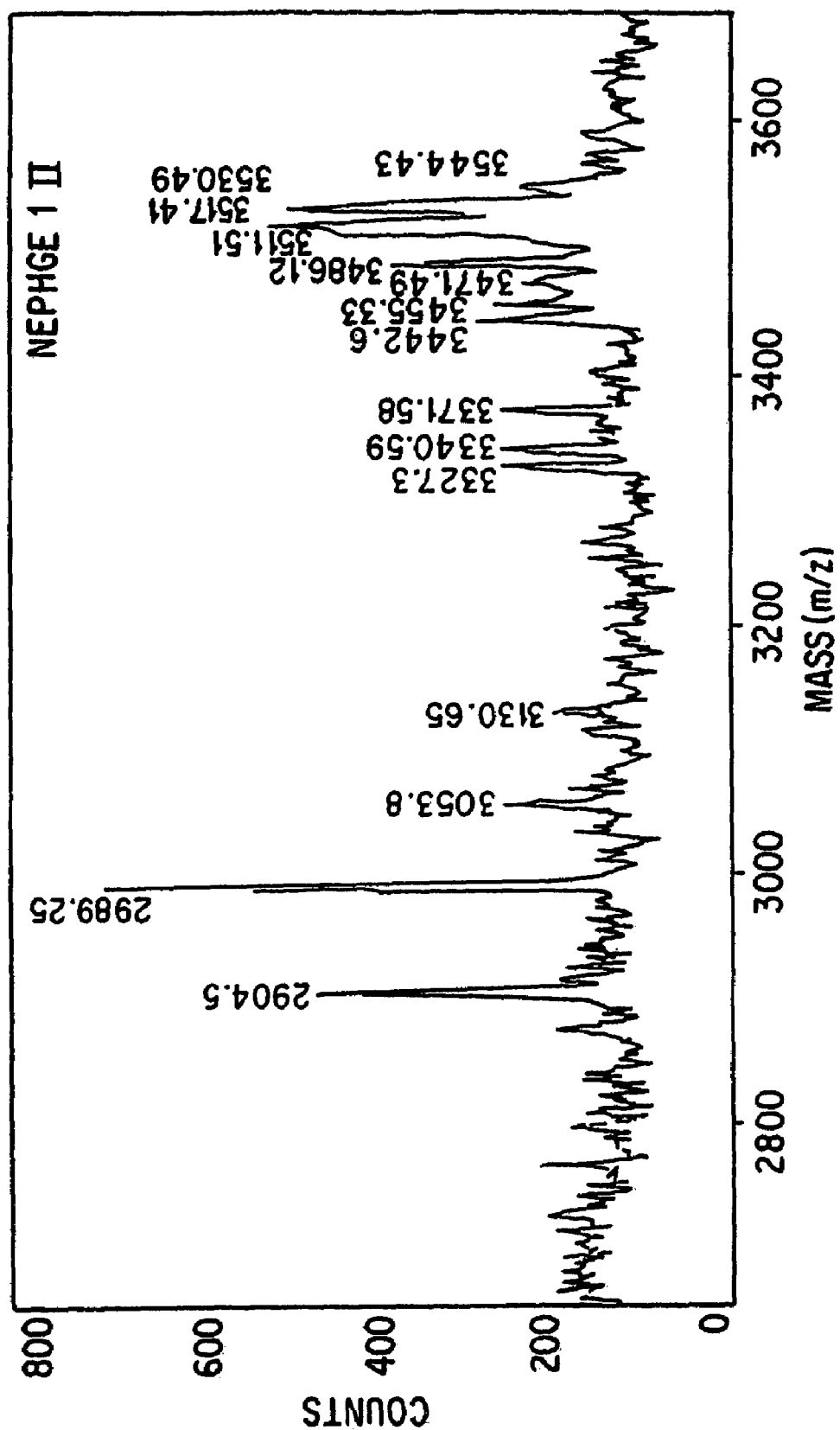
Figure 10:
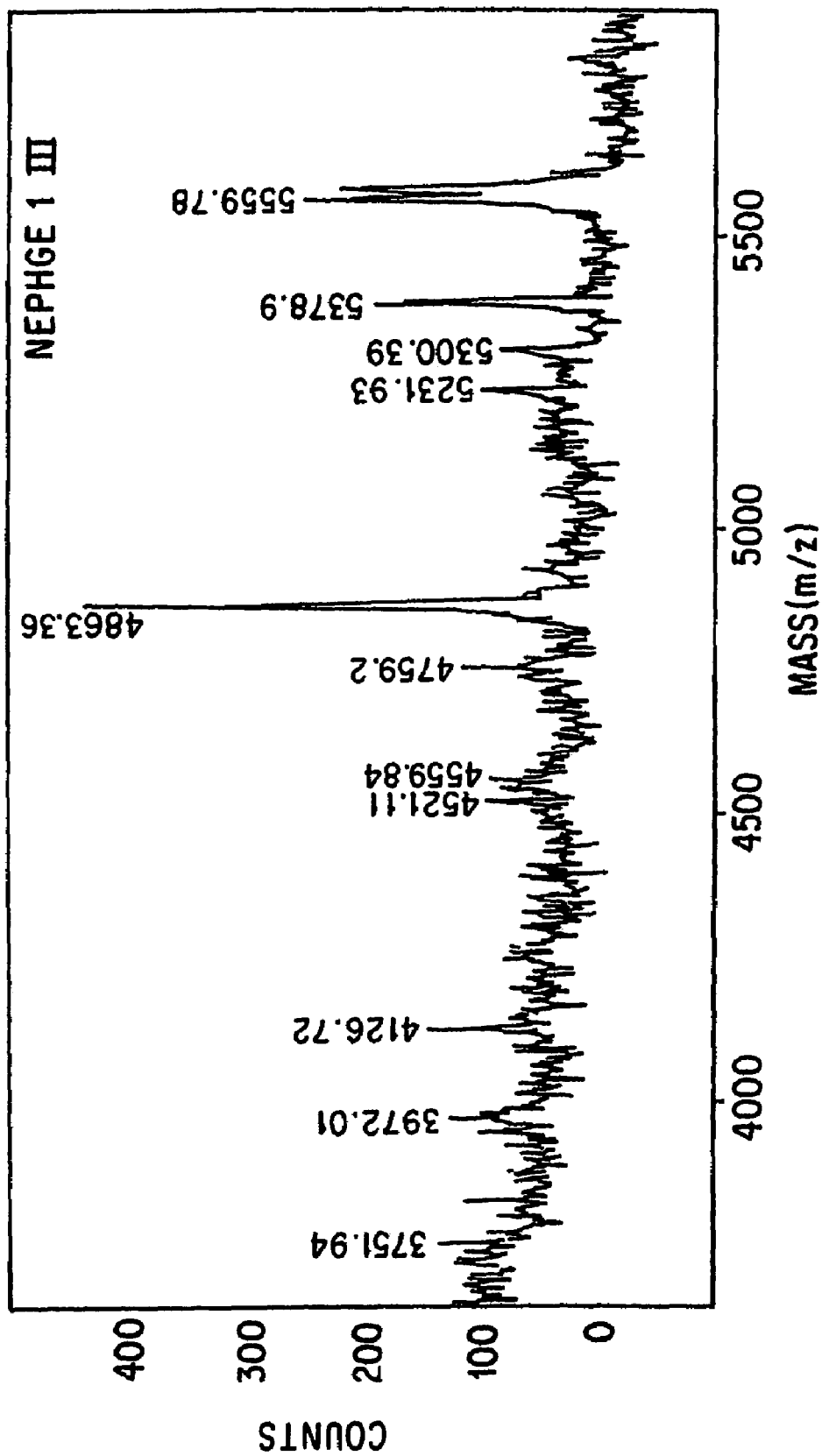
Figure 11:
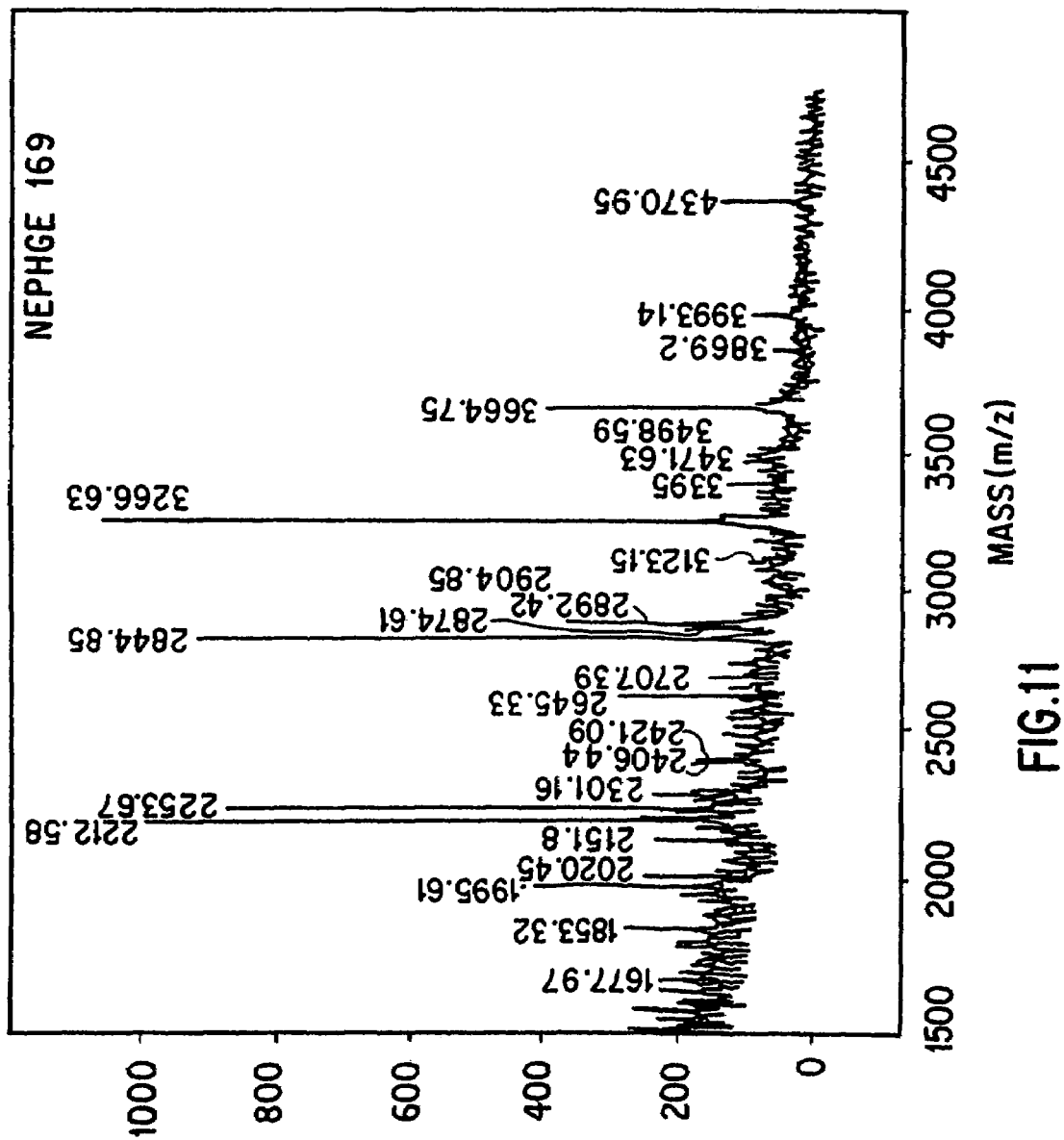
FIG. 11 is the mass spectroscopy spectrum for a diabetes-mediating, tentatively identified as 6-phosphobructose-2-kinase, NEPHGE Spot No. 169, determined as indicated.
Figure 12:
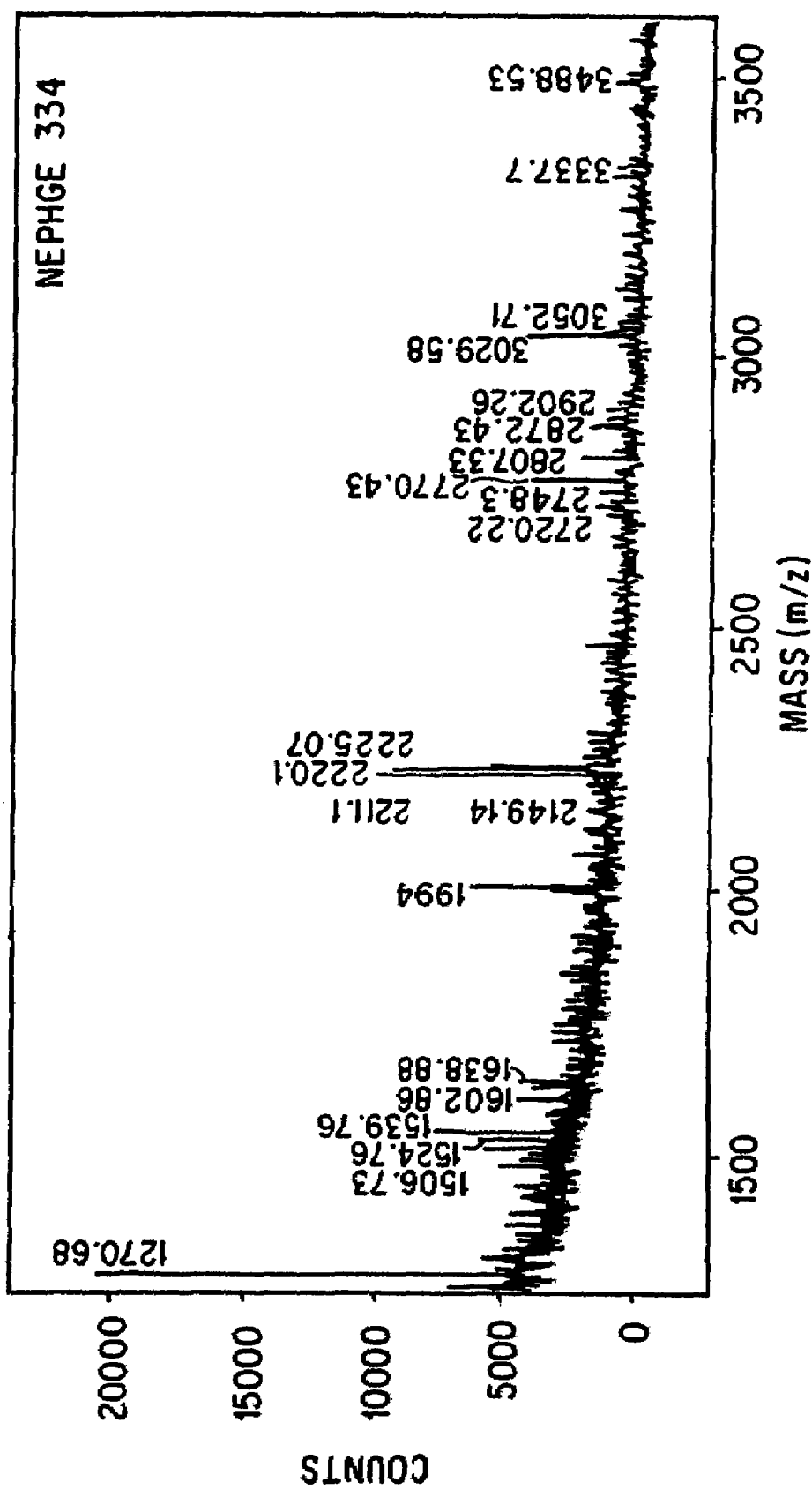
FIG. 12 is the mass spectroscopy spectrum for a diabetes-mediating, tentatively identified as triose phosphate isomerase, NEPHGE Spot No. 334, determined as indicated.
Figure 13:
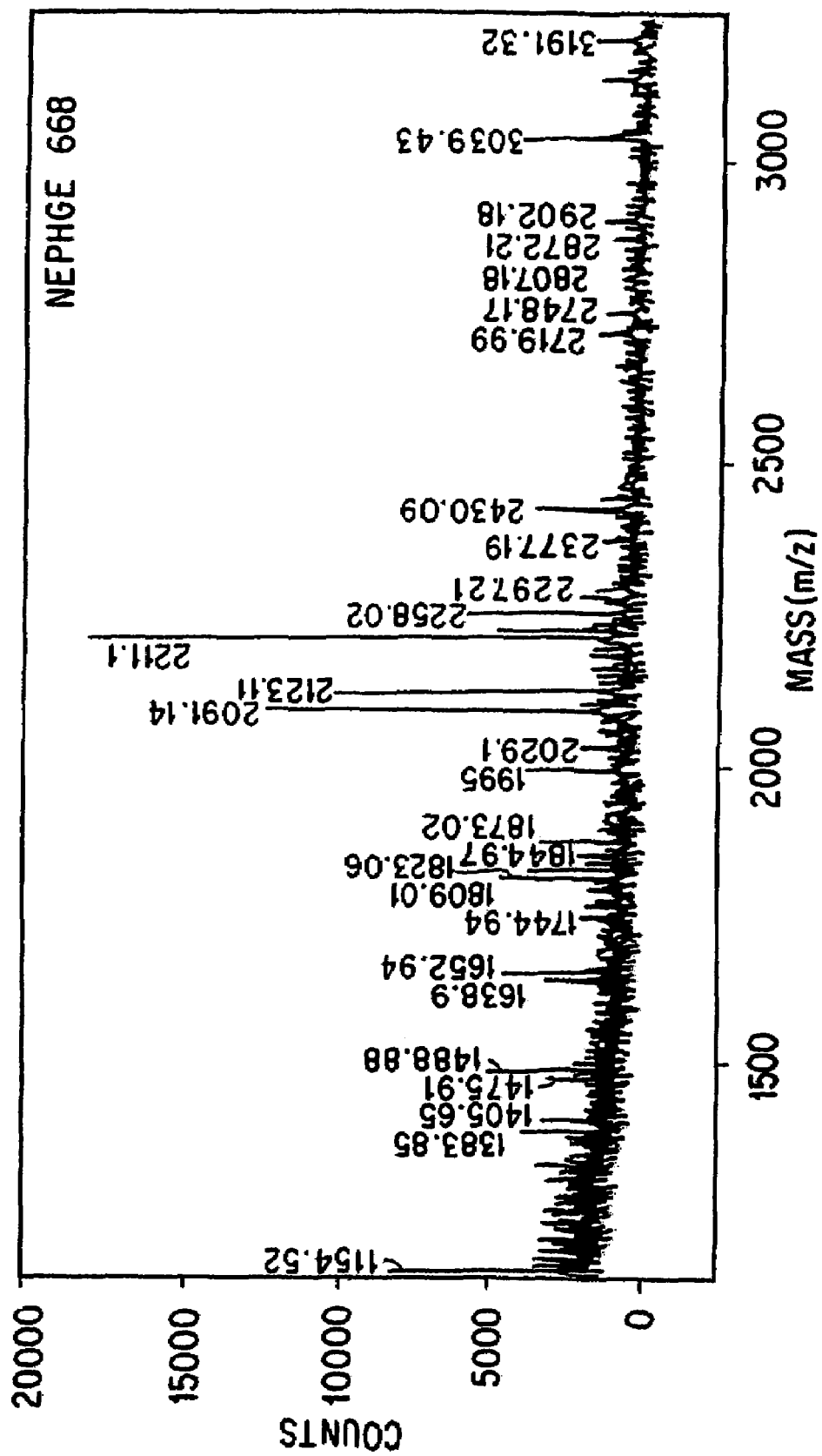
FIG. 13 is the mass spectroscopy spectrum for a diabetes-mediating, tentatively identified as fructose biphosphate aldolase, NEPHGE Spot No. 668, determined as indicated.
Figure 14:
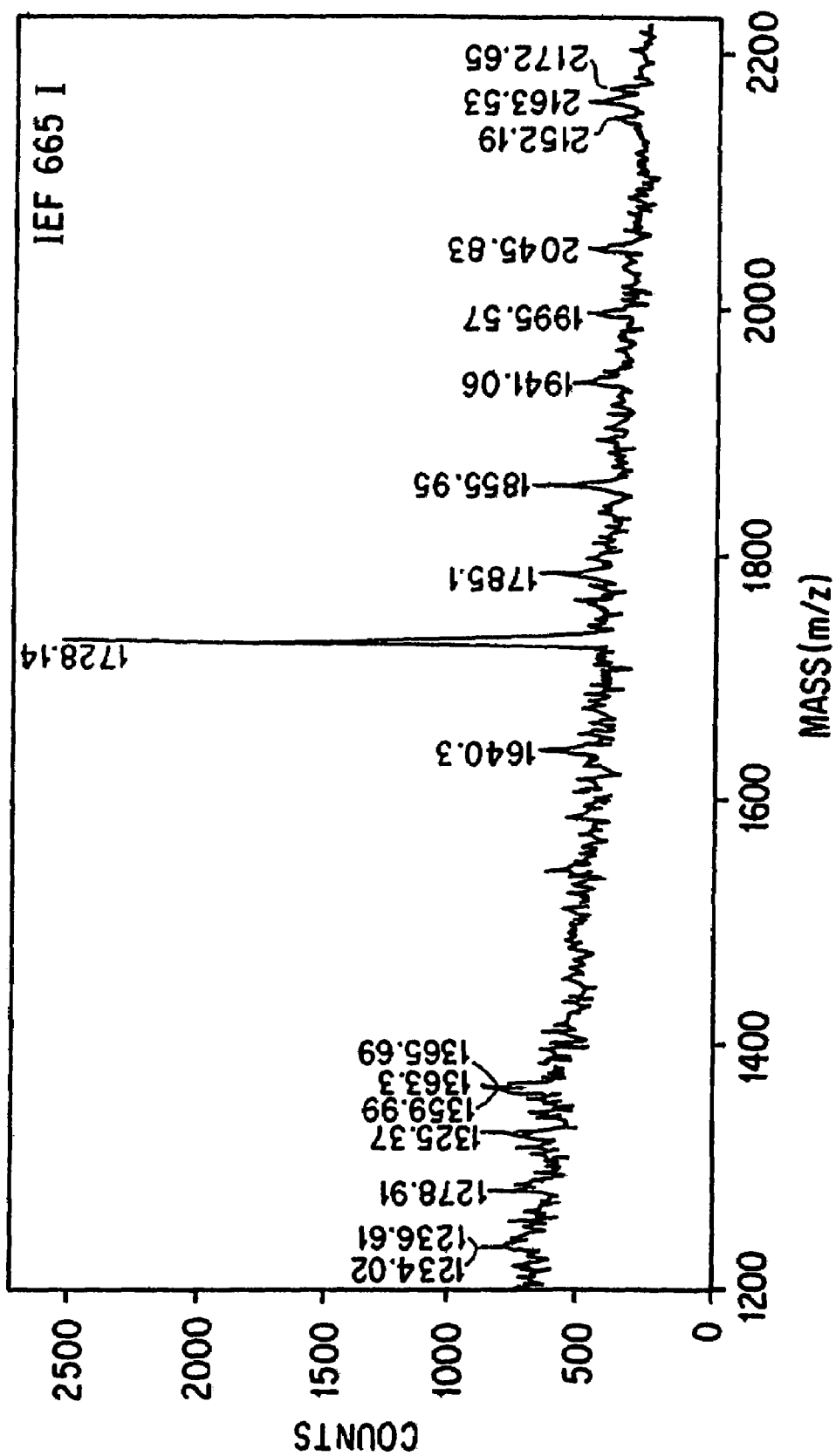
FIGS. 14-15 are the mass spectroscopy spectrum for a novel diabetes-mediating protein, termed "IEF Spot No. 665," having a molecular weight of 42,243 daltons and a pI of 5.82, determined as indicated.
Figure 15:
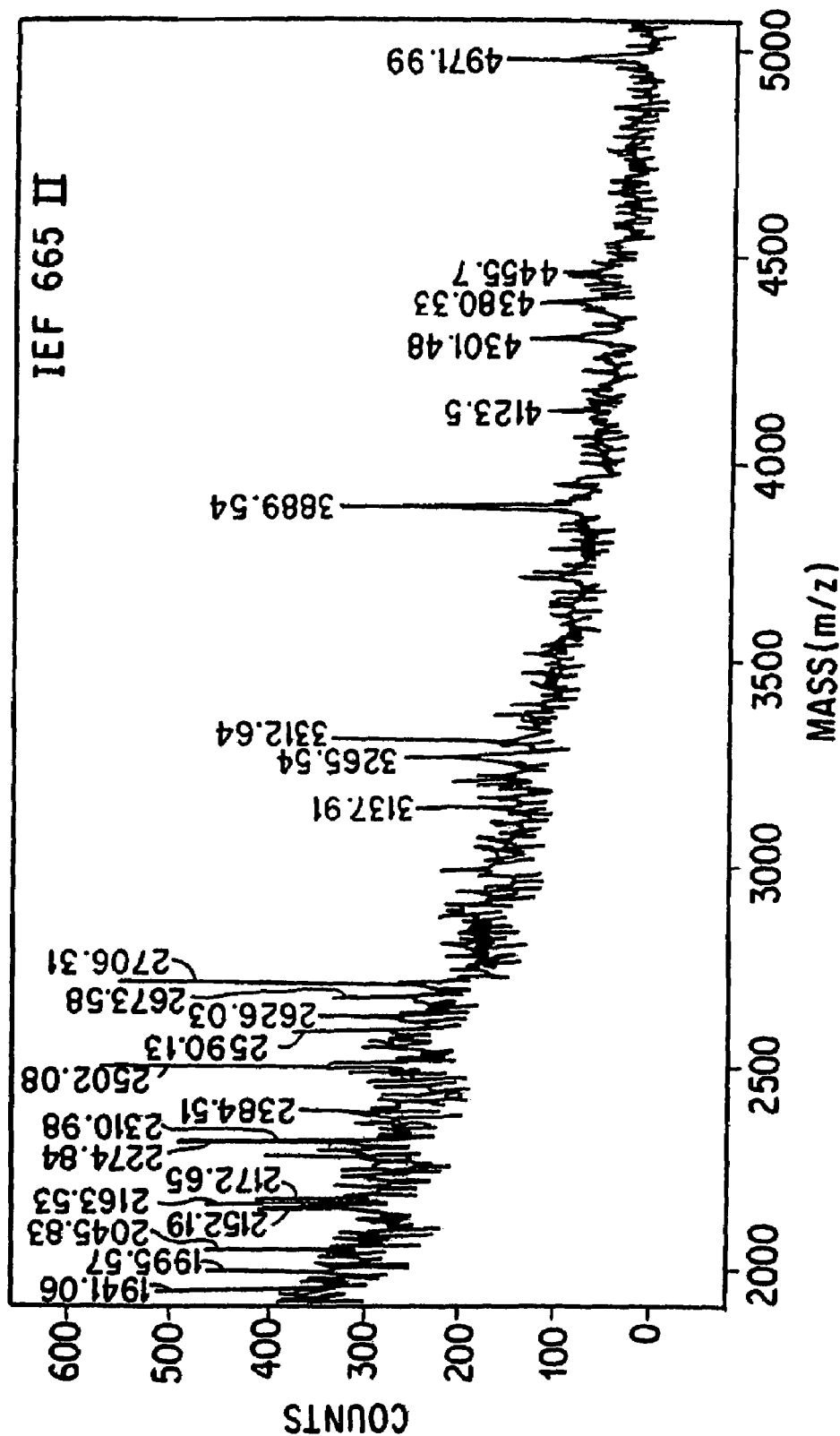
Figure 16:
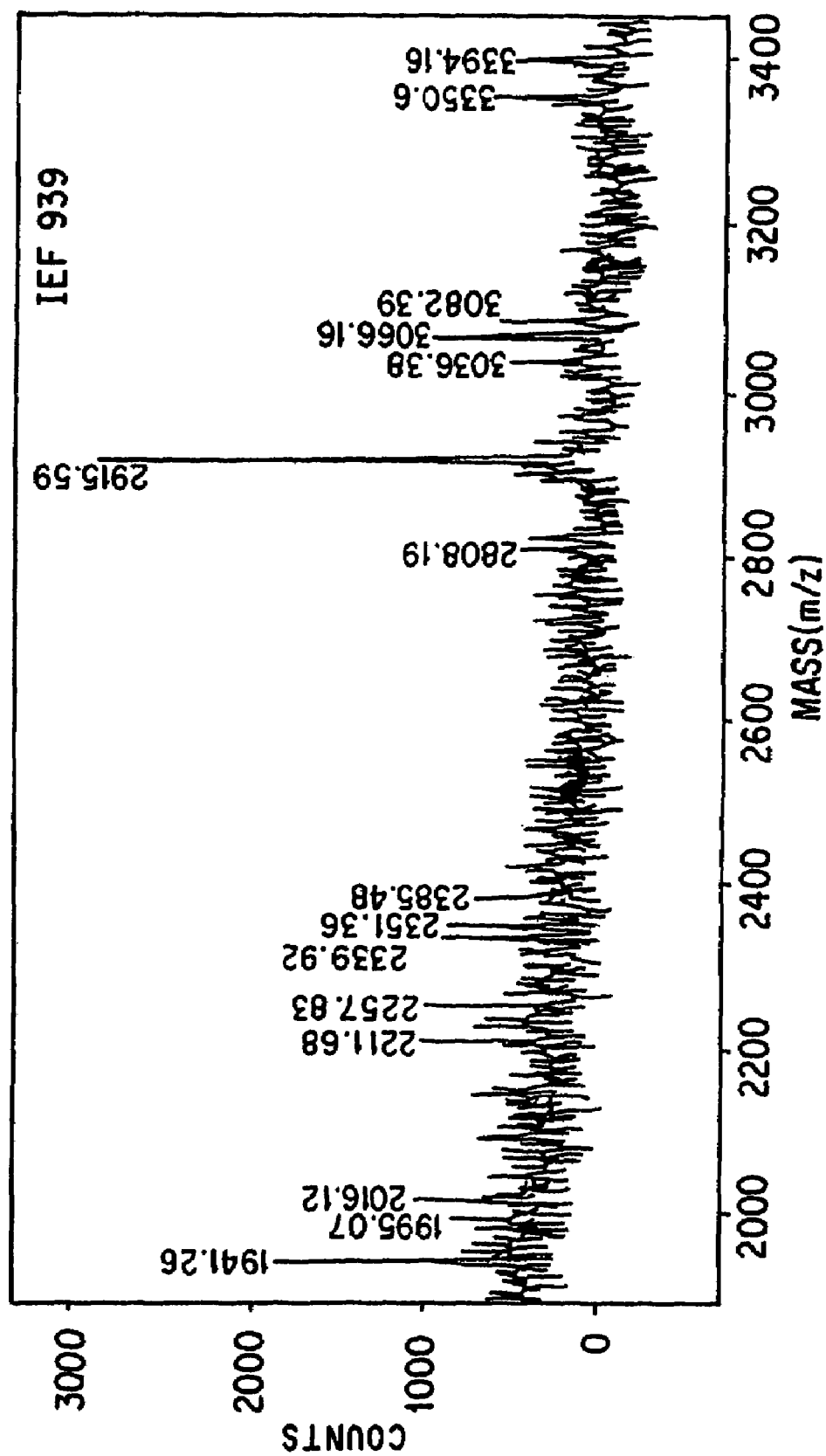
FIG. 16 is the mass spectroscopy spectrum for a novel diabetes-mediating protein, termed, "IEF Spot No. 939," having a molecular weight of 25,851 daltons and a pI of 5.09, determined as indicated.
Figure 17:
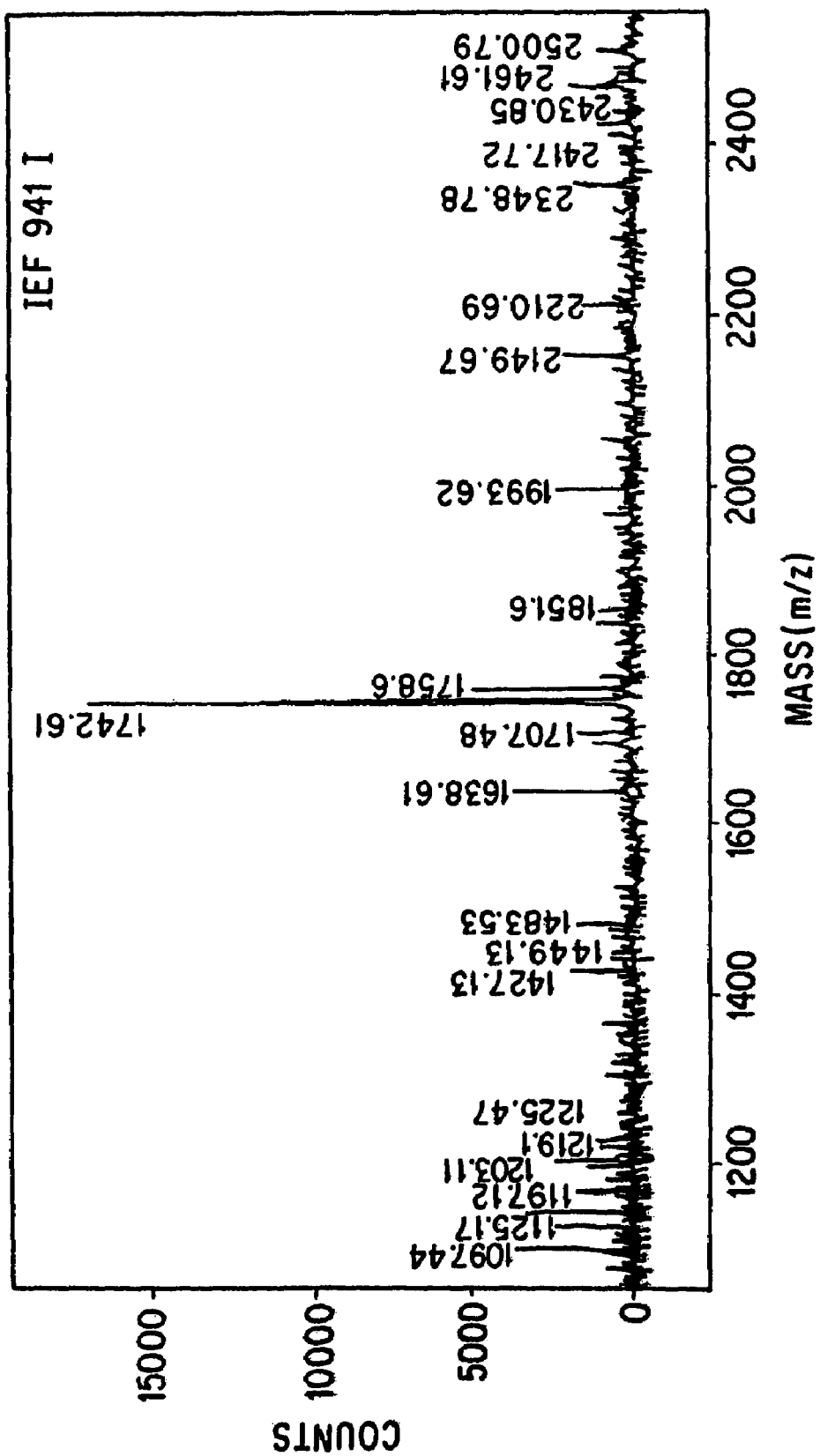
FIGS. 17-18 are the mass spectroscopy spectrum for a novel diabetes-mediating protein, termed "EF Spot No. 941" having a molecular weight of 22,704 daltons and a pI of 5.15, determined as indicated.
Figure 18:
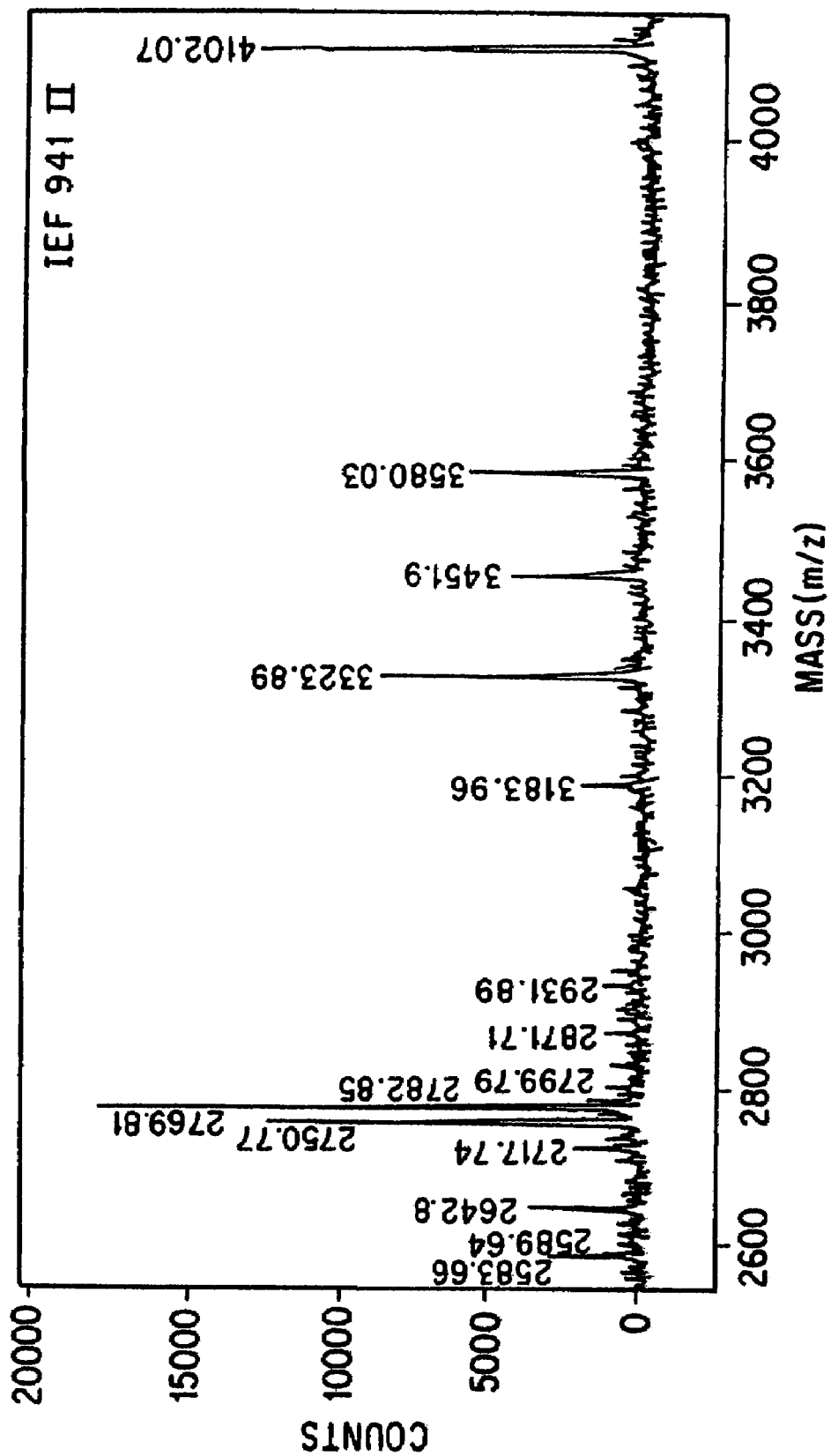
Figure 19:
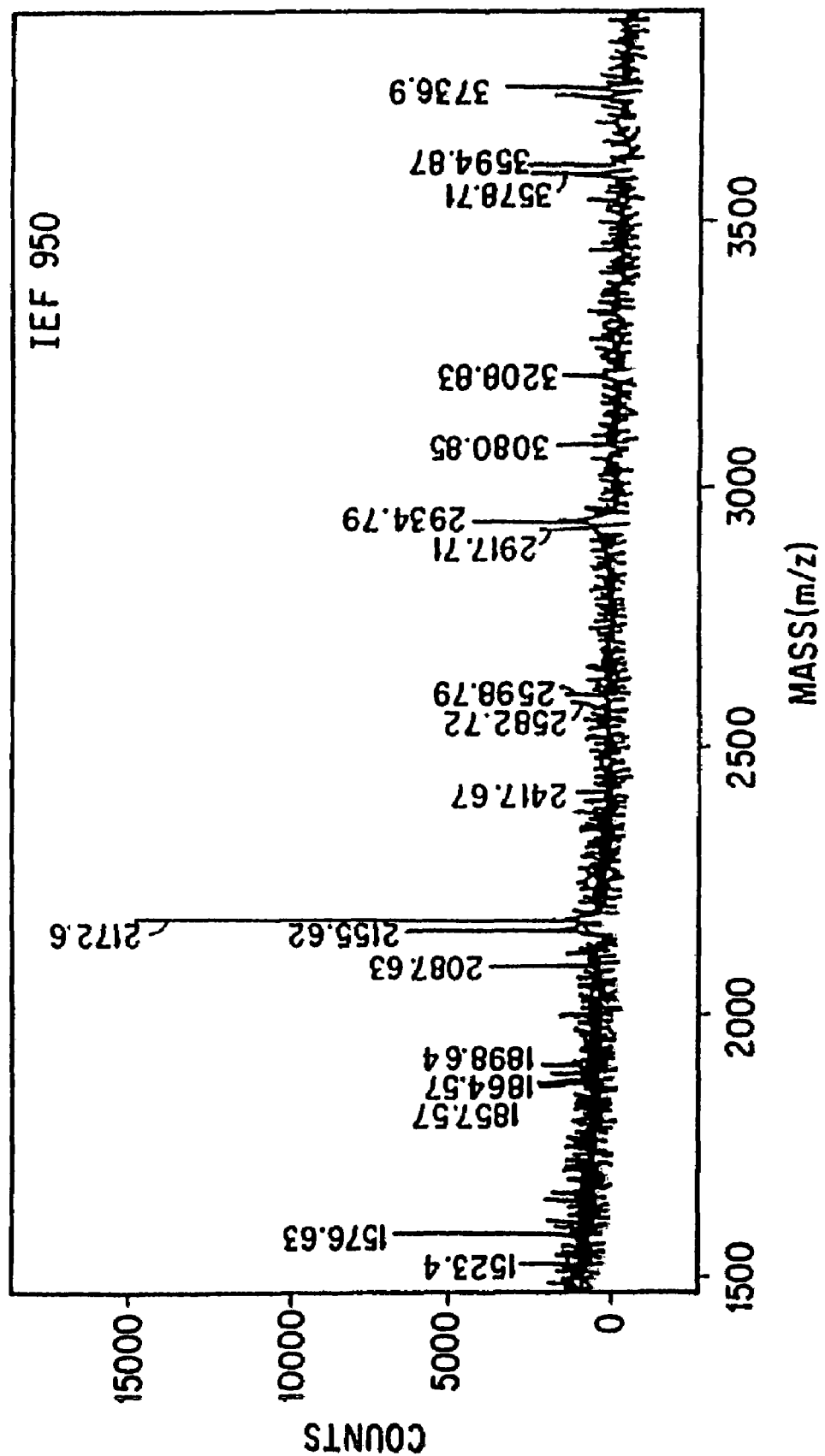
FIG. 19 is the mass spectroscopy spectrum for a novel diabetes-mediating protein, termed "IEF Spot No. 950," having a molecular weight of 25,753 daltons and a pI of 4.53, determined as indicated.
Figure 20:
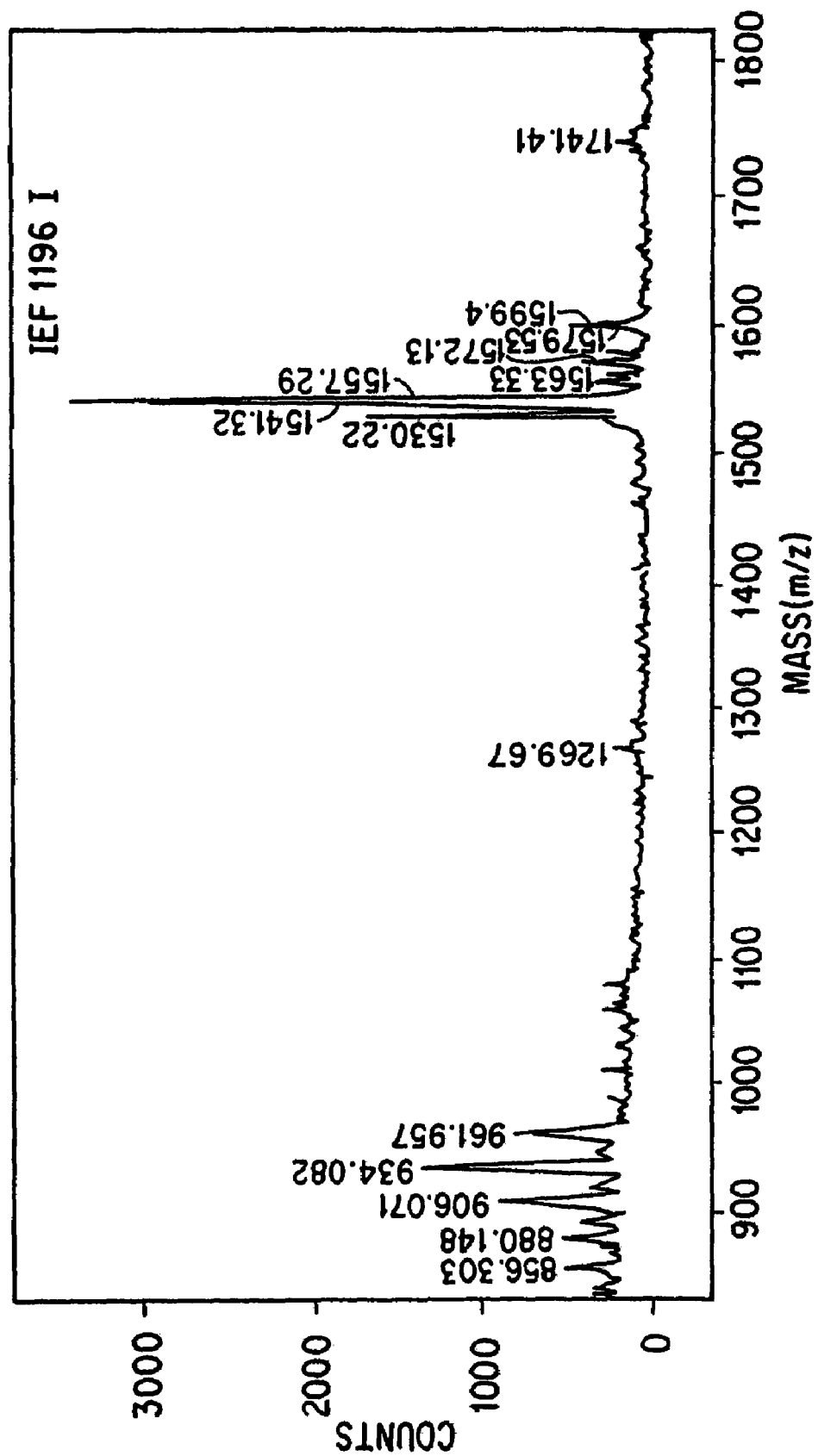
FIGS. 20-23 are the mass spectroscopy spectrum for a novel diabetes-mediating protein, termed "IEF Spot No. 1196" having a molecular weight of 143,064 daltons and a pI of 5.41, determined as indicated.
Figure 21:
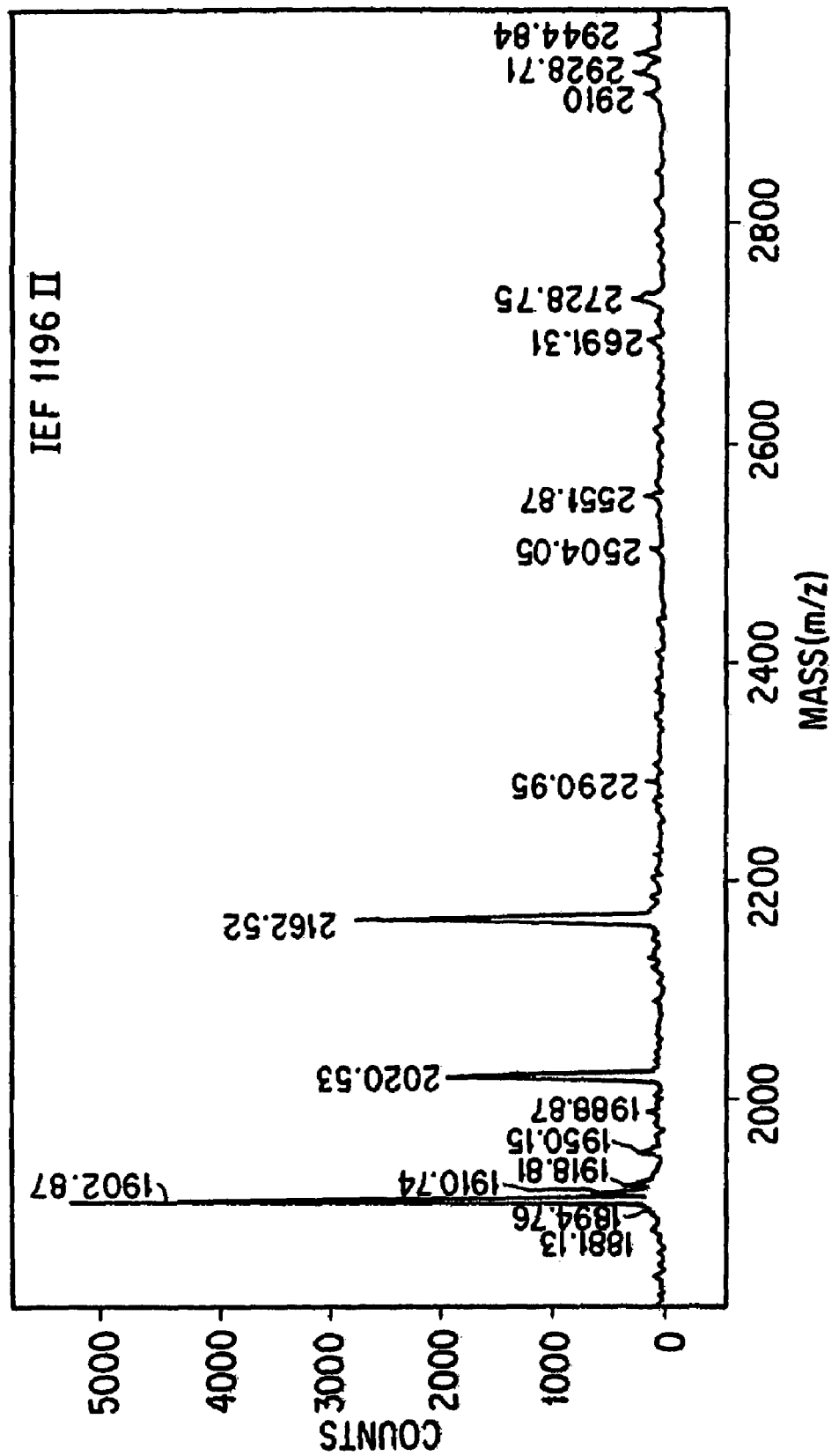
Figure 22:
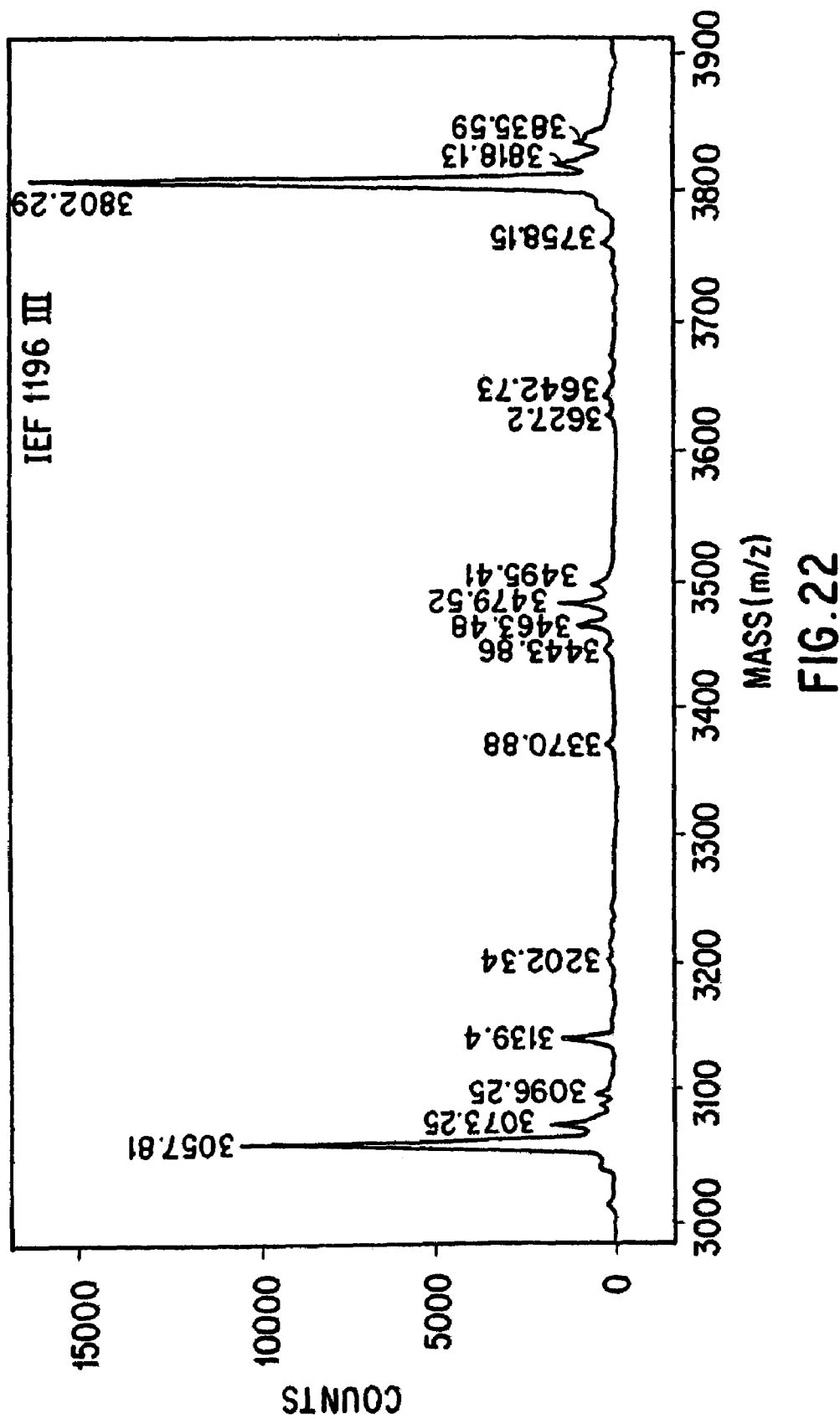
Figure 23:
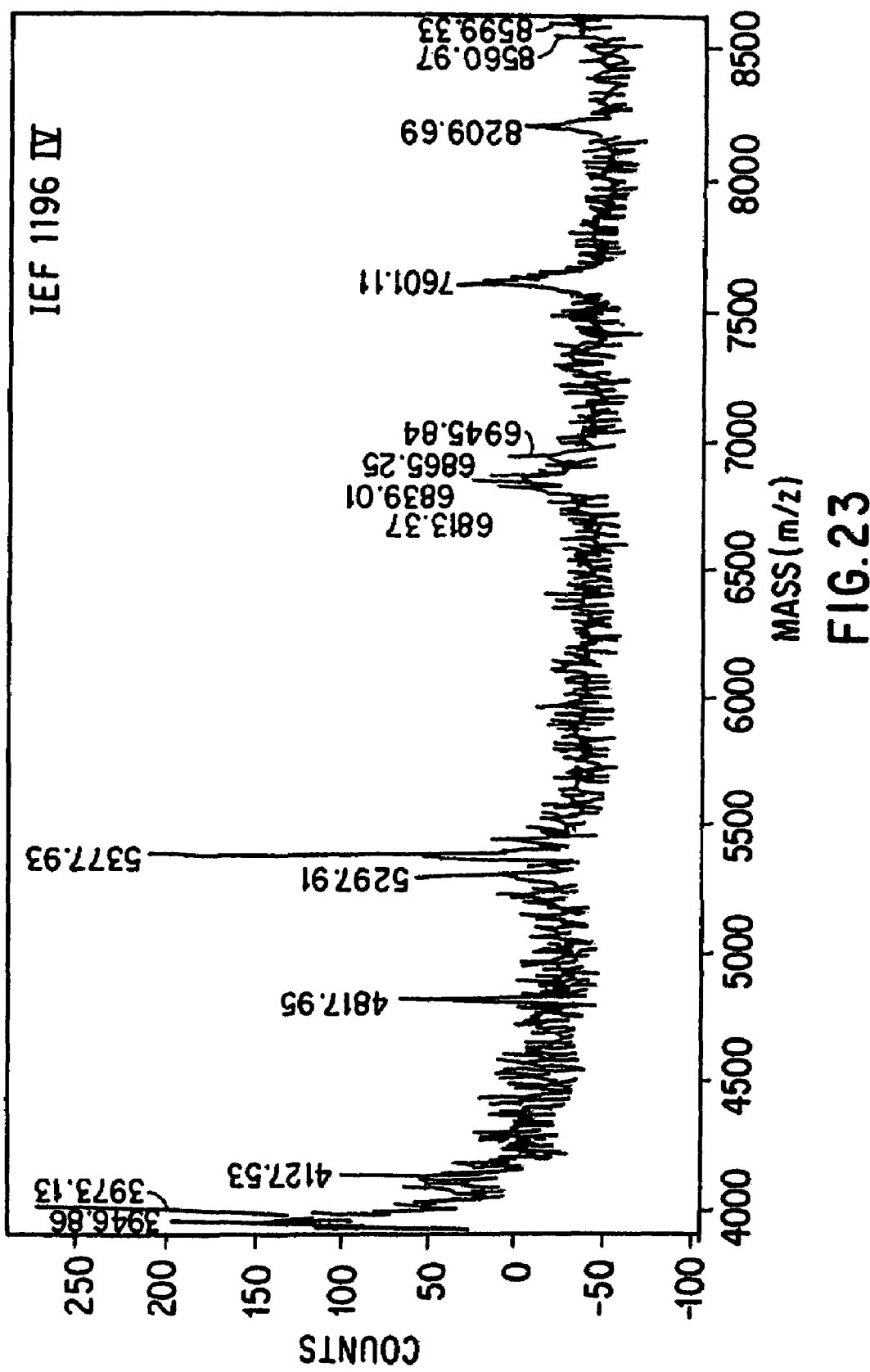
Figure 24:
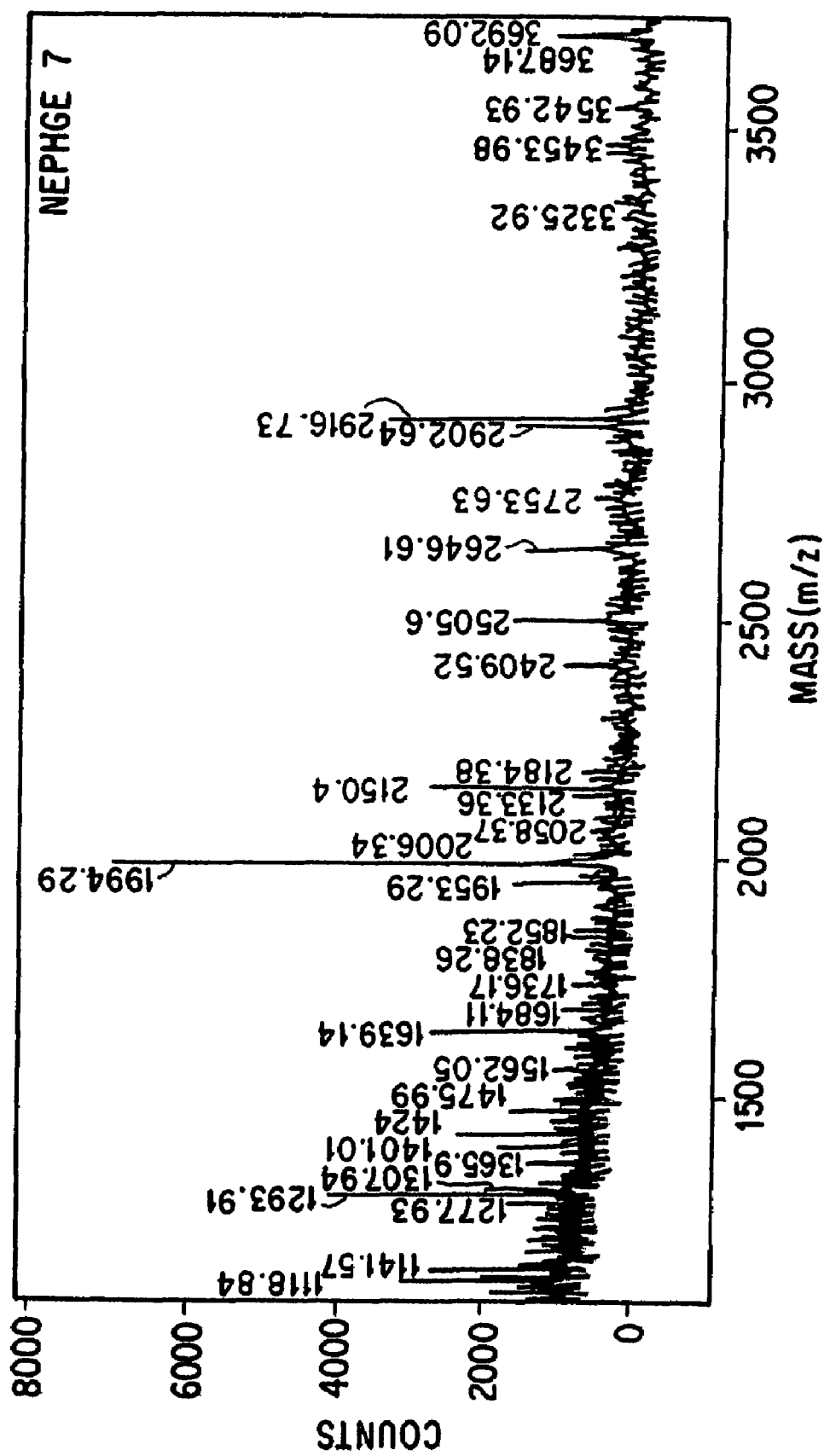
FIG. 24 is the mass spectroscopy spectrum for a novel diabetes-mediating protein, termed "NEPHGE Spot No. 7," having a molecular weight of 65,522 daltons and a pI of 7.28, determined as indicated.
Figure 25:
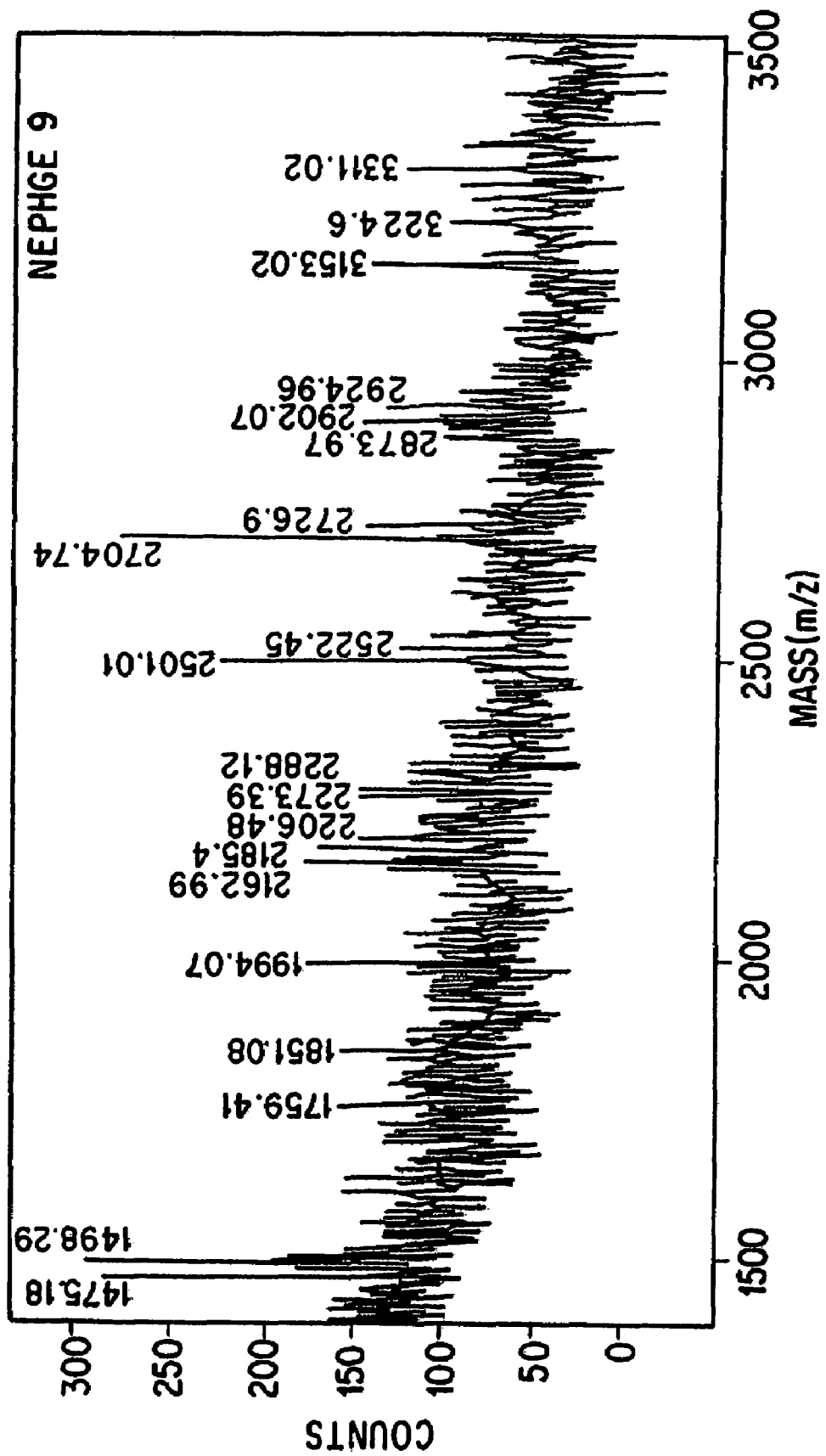
FIG. 25 is the mass spectroscopy spectrum for a novel diabetes-mediating protein, termed "NEPHGE Spot No. 9," having a molecular weight of 115,709 daltons and a pI of 8.33, determined as indicated.
Figure 26:
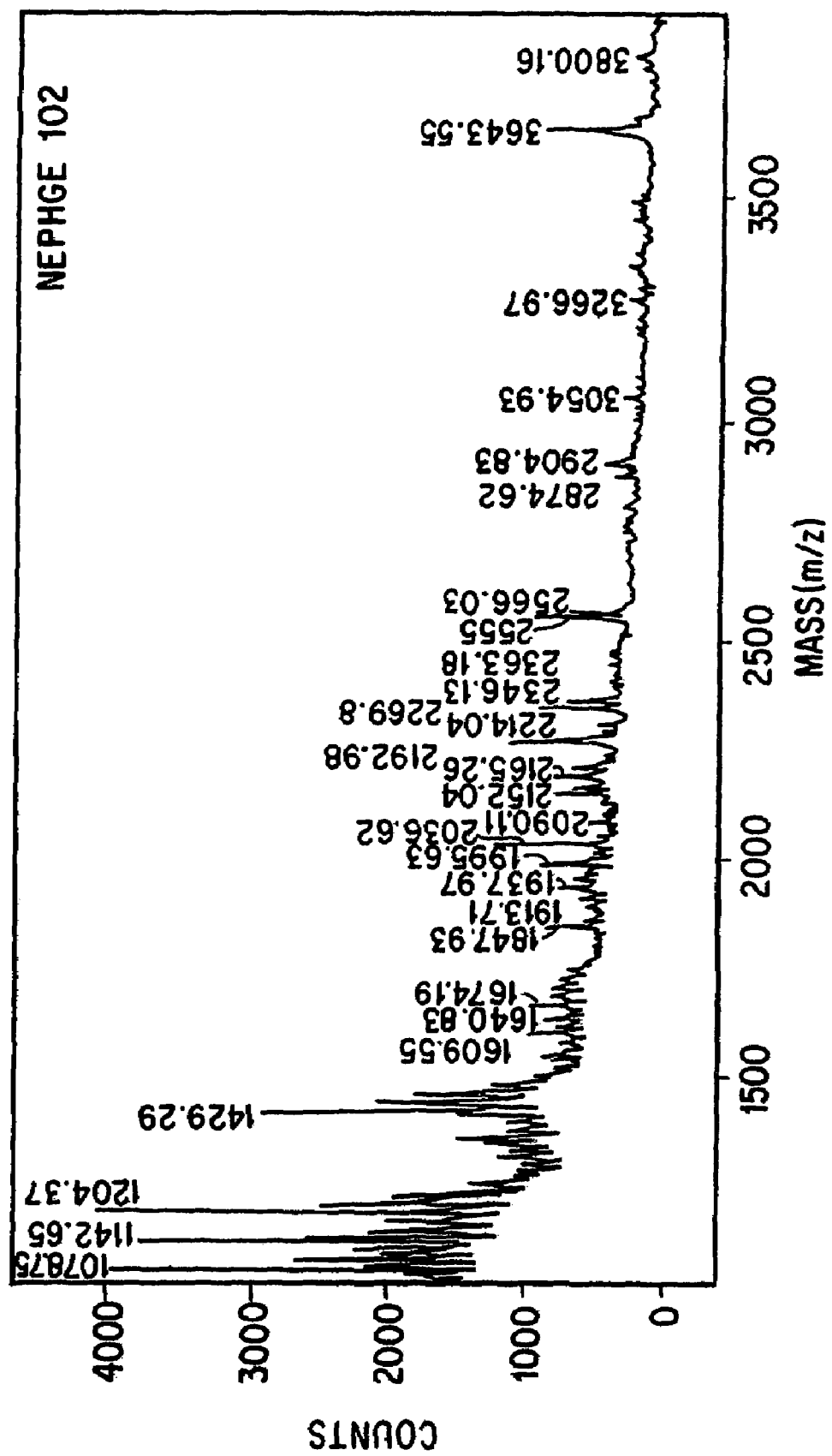
FIG. 26 is the mass spectroscopy spectrum for a novel diabetes-mediating protein, termed "NEPHGE Spot No. 102," having a molecular weight of 63,560 daltons and a pI of 7.26, determined as indicated.
Figure 27:
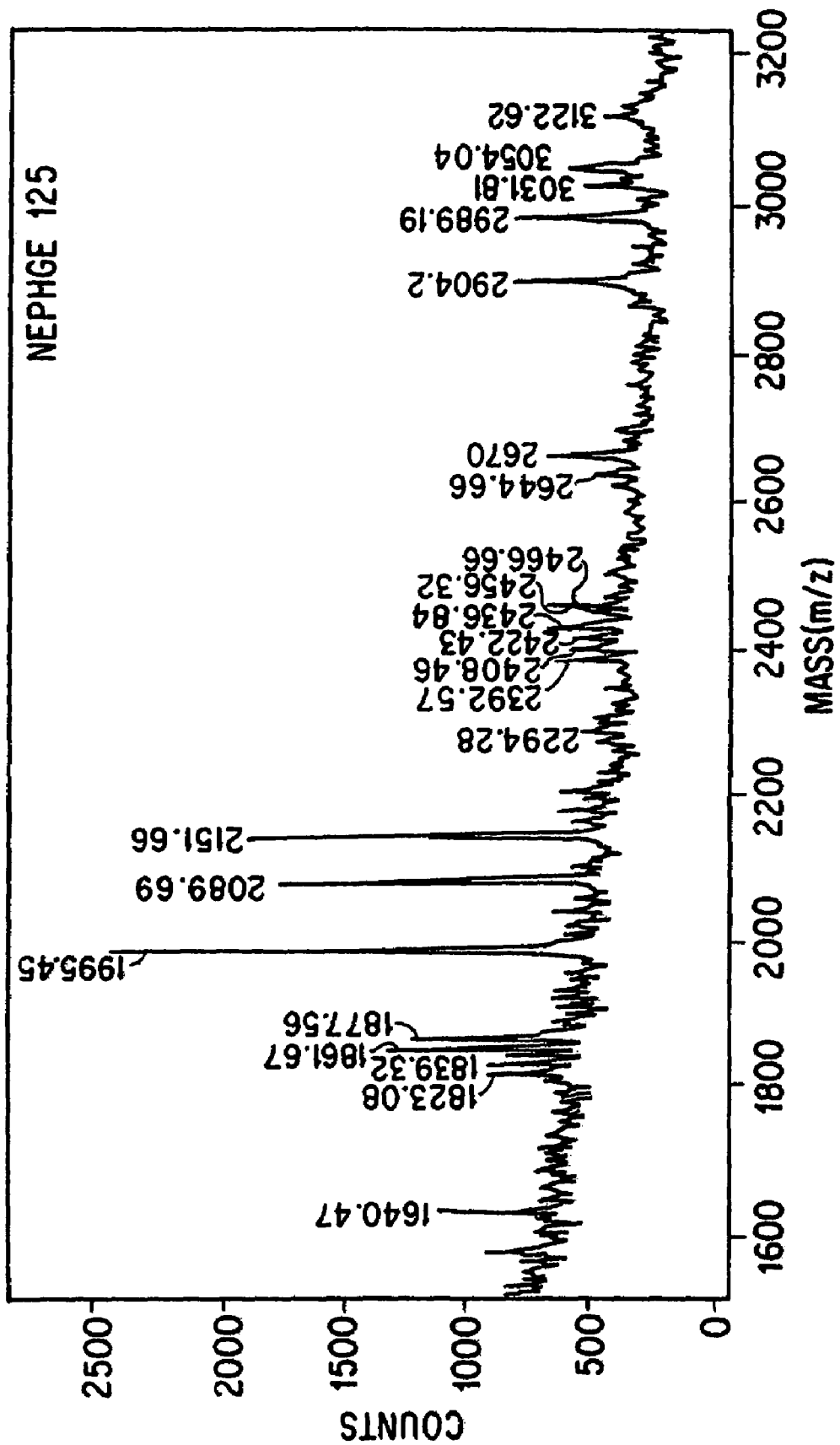
FIG. 27 is the mass spectroscopy spectrum for a novel diabetes-mediating protein, termed "NEPHGE Spot No. 123," having a molecular weight of 57,040 daltons and a pI of 8.17, determined as indicated.
Figure 28:
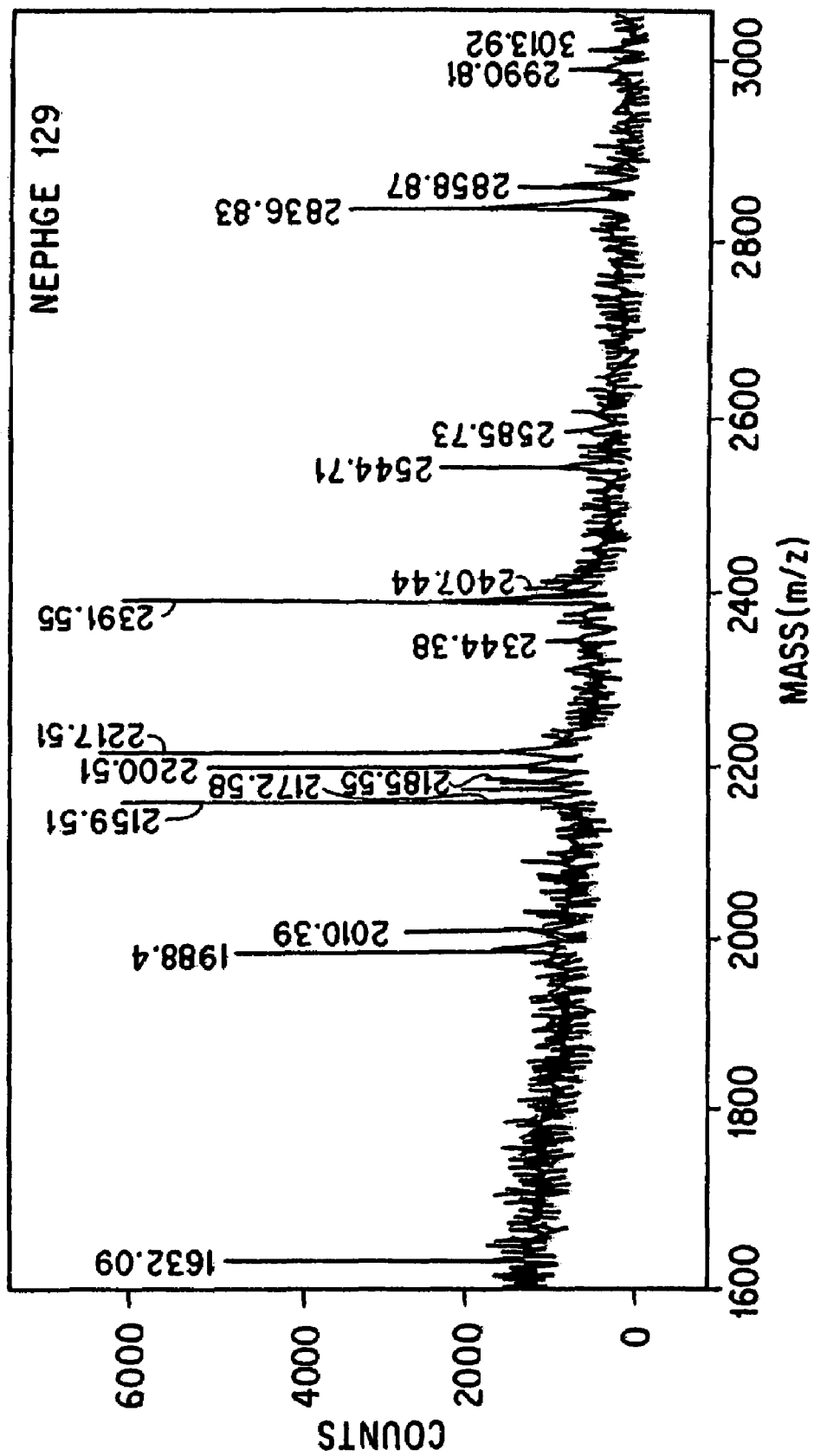
FIG. 28 is the mass spectroscopy spectrum for a novel diabetes-mediating protein, termed "NEPHGE Spot No. 129," having a molecular weight of 57,609 daltons and a pI of 7.72, determined as indicated.
Figure 29:
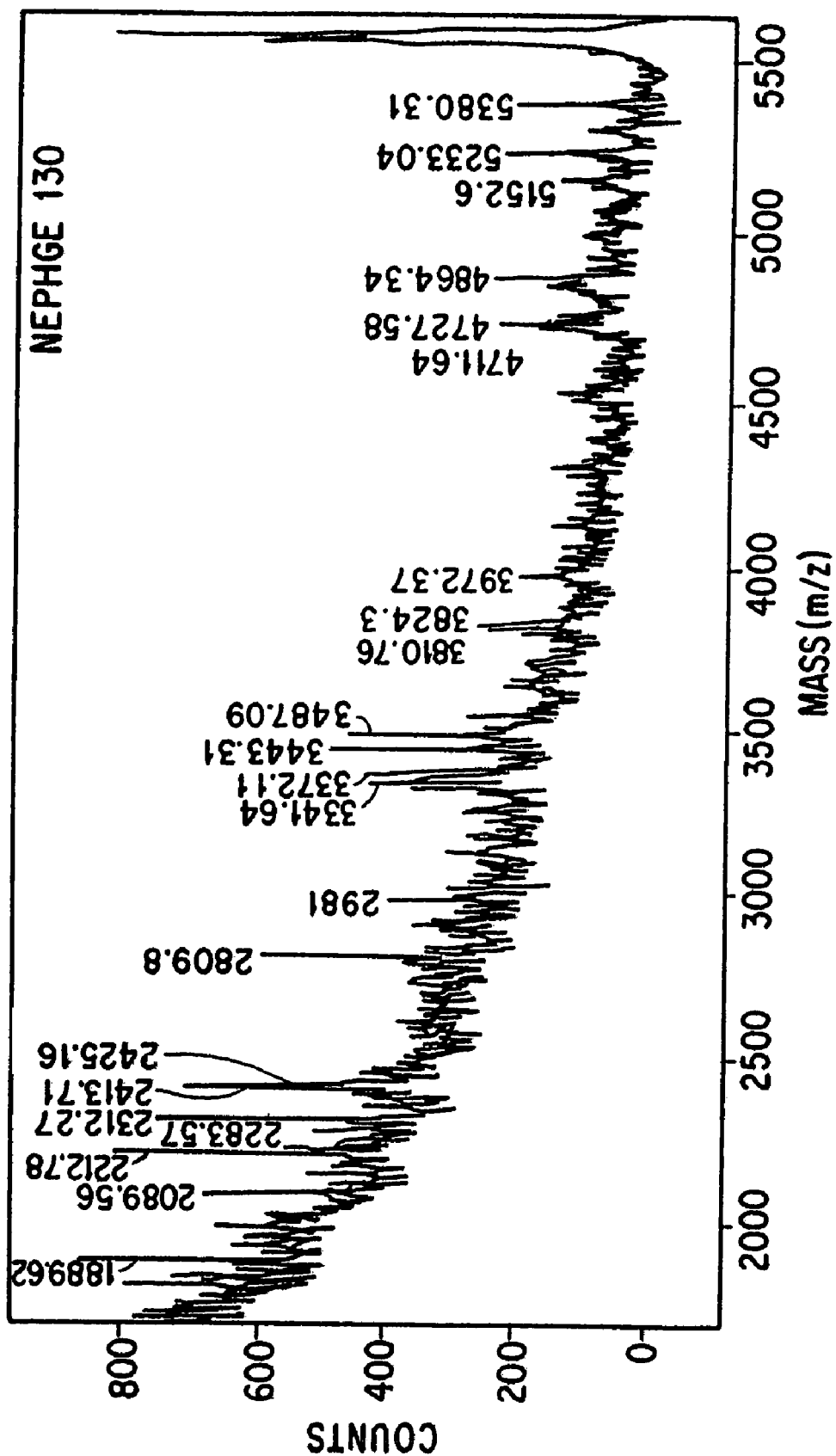
FIG. 29 is the mass spectroscopy spectrum for a novel diabetes-mediating protein, termed "NEPHGE Spot No. 130," having a molecular weight of 55,734 daltons and a pI of 8.07, determined as indicated.
Figure 30:
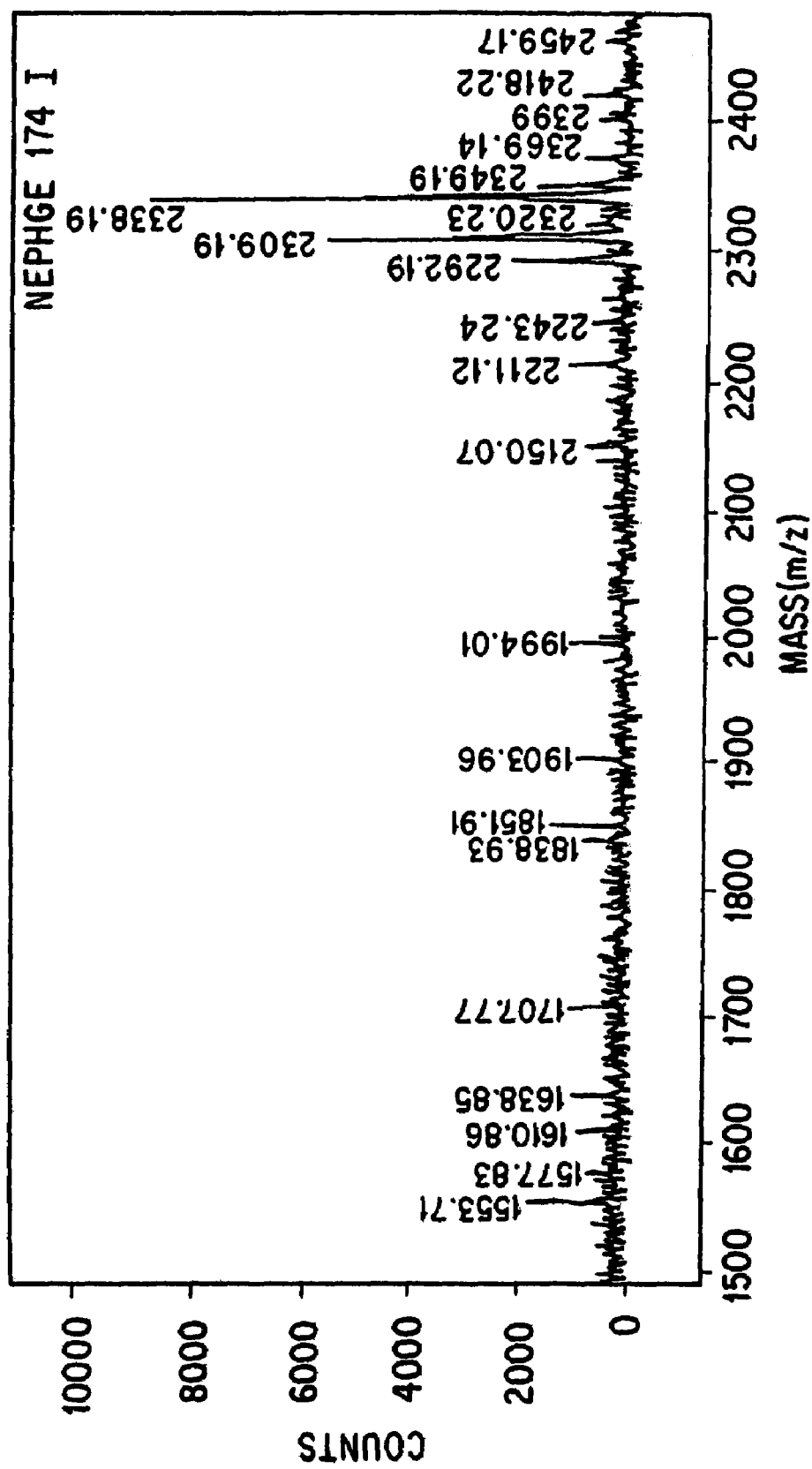
FIGS. 30-31 are the mass spectroscopy spectrum for a novel diabetes-mediating protein, termed "NEPHGE Spot No. 174," having a molecular weight of 53,830 daltons and a pI of 7.92, determined as indicated.
Figure 31:
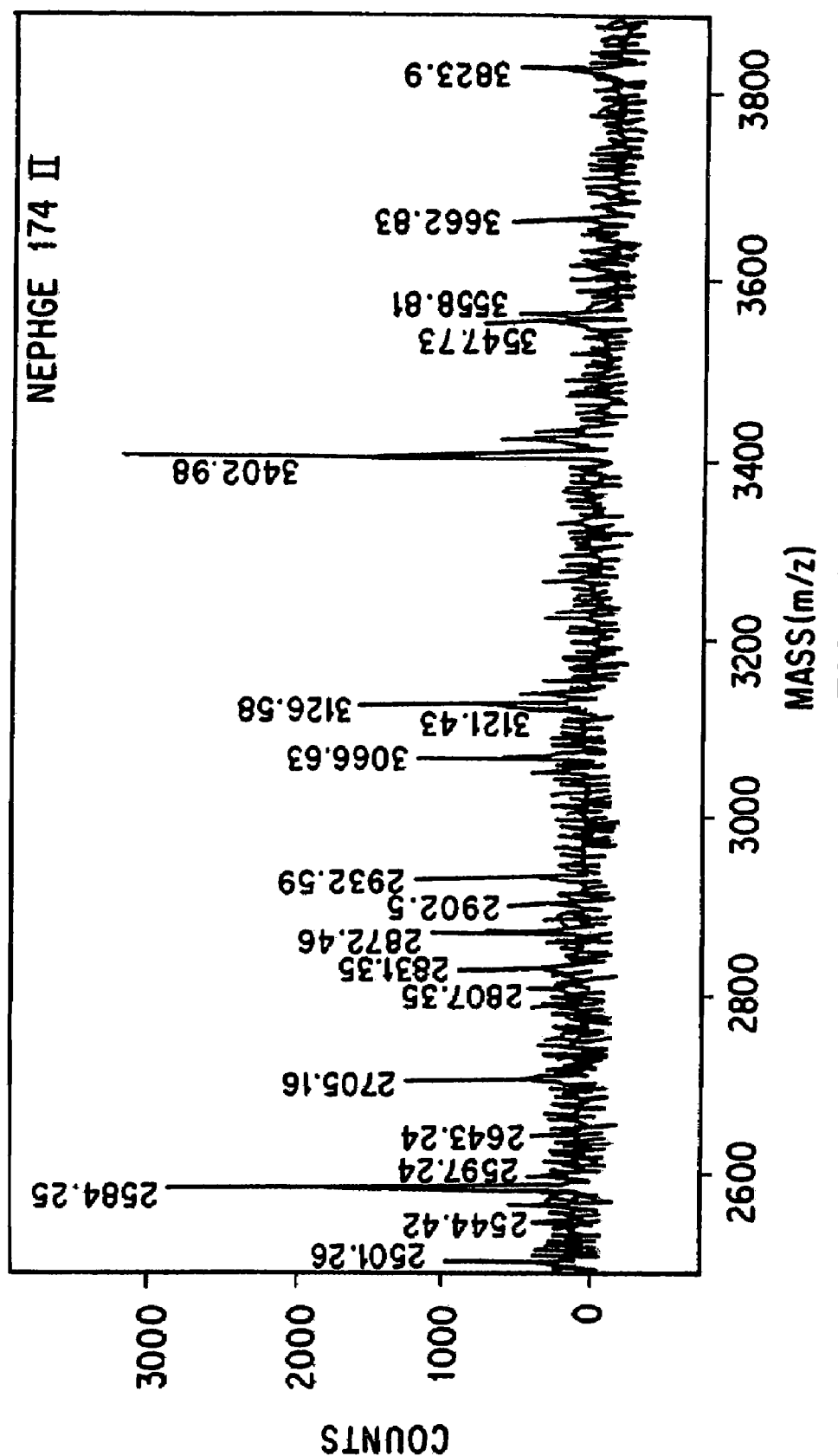
Figure 32:
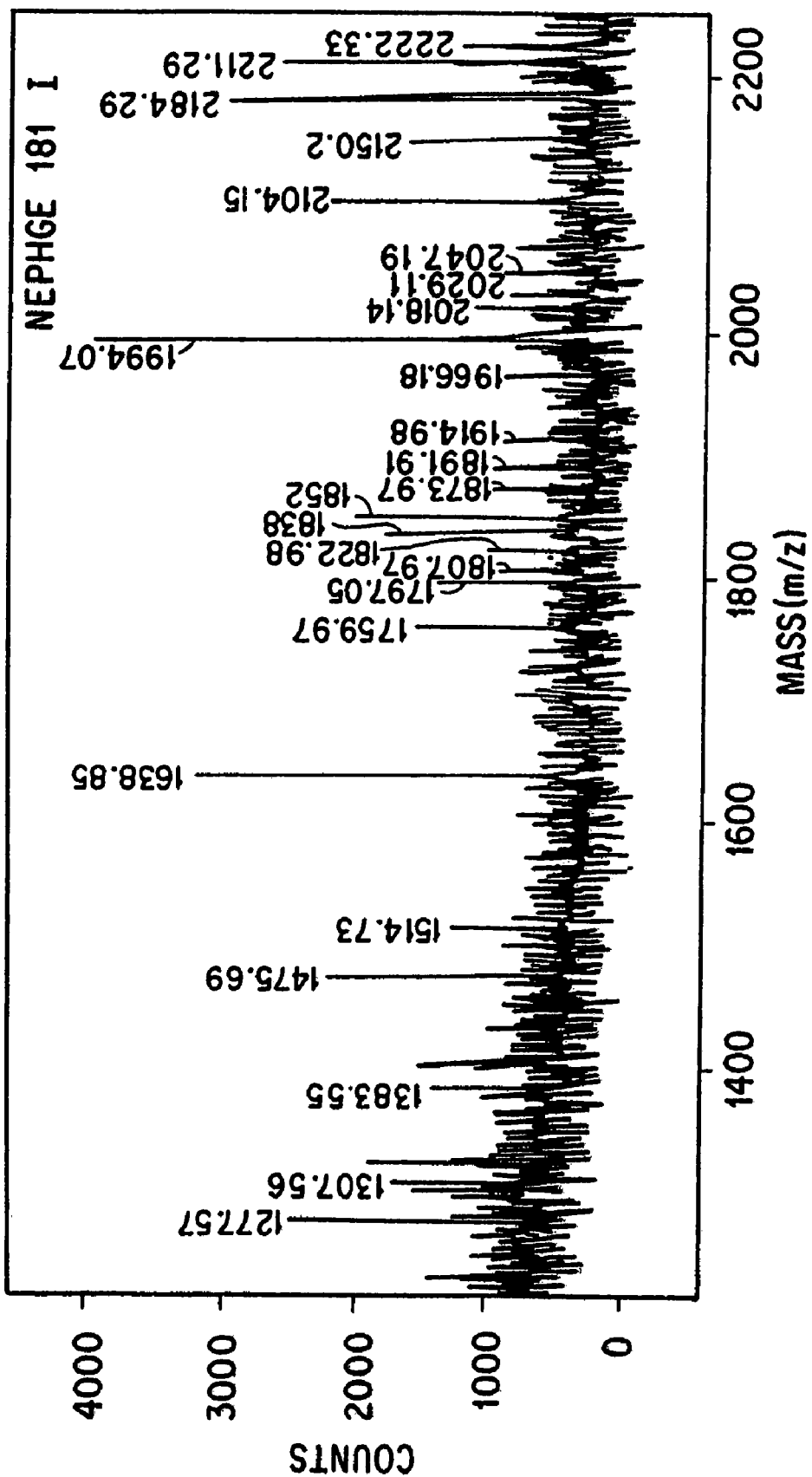
FIGS. 32-33 are the mass spectroscopy spectrum for a novel diabetes-mediating protein, termed "NEPHGE Spot No. 181," having a molecular weight of 49,422 daltons and a pI of 7.40, determined as indicated.
Figure 33:
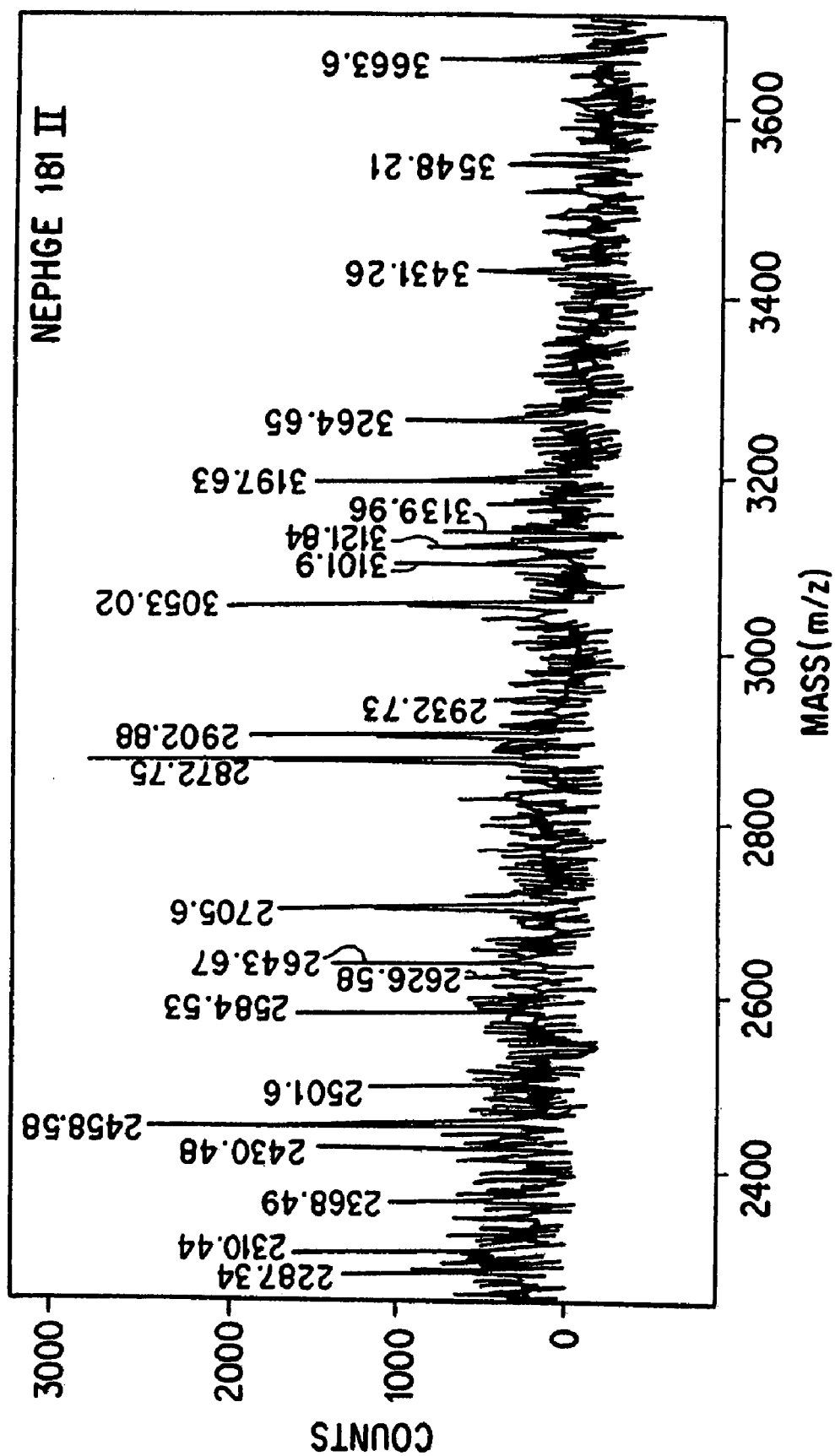
Figure 34:
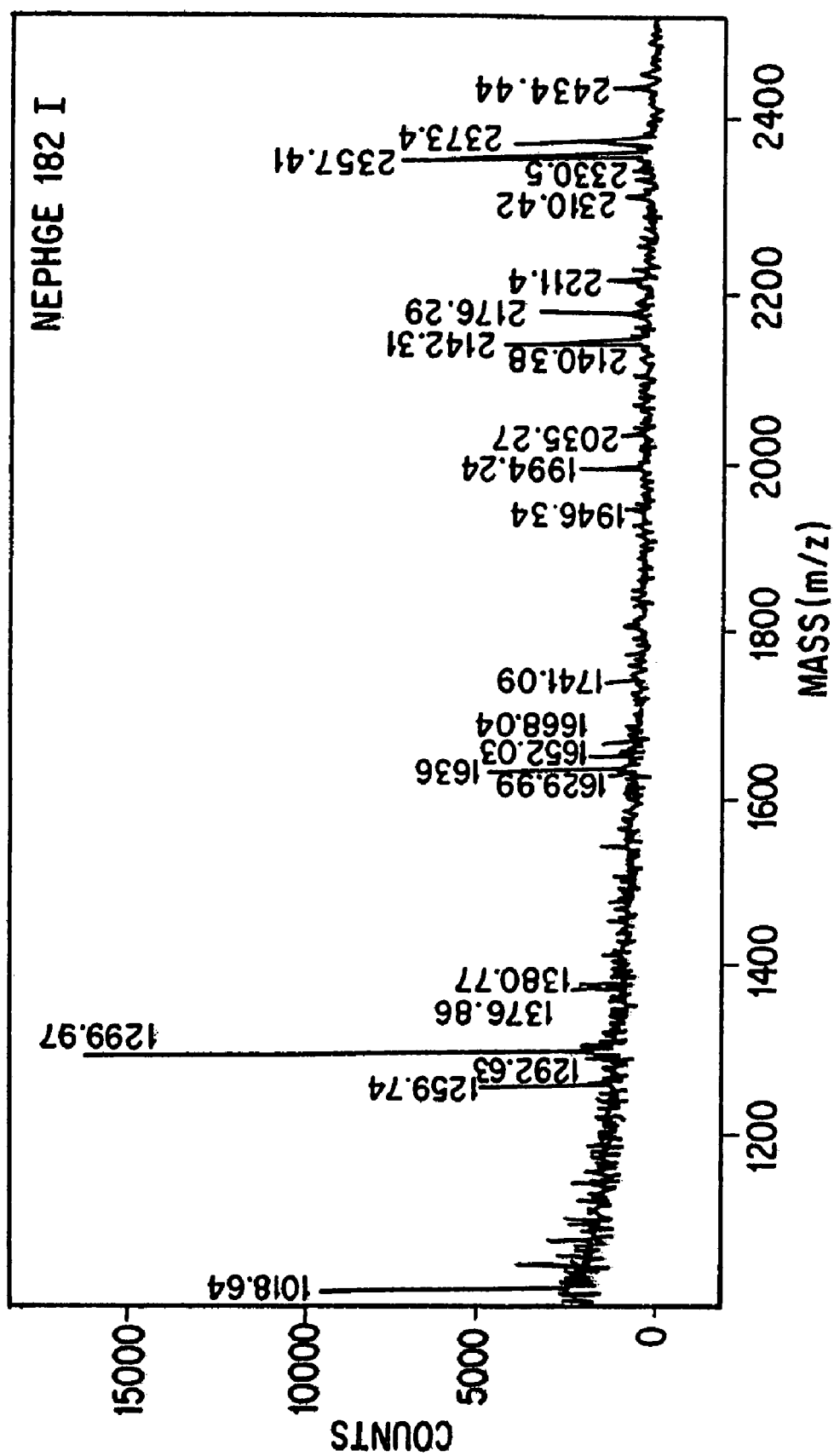
FIGS. 34-35 are the mass spectroscopy spectrum for a novel diabetes-mediating protein, termed "NEPHGE Spot No. 182," having a molecular weight of 54,098 daltons and a pI of 7.61, determined as indicated.
Figure 35:
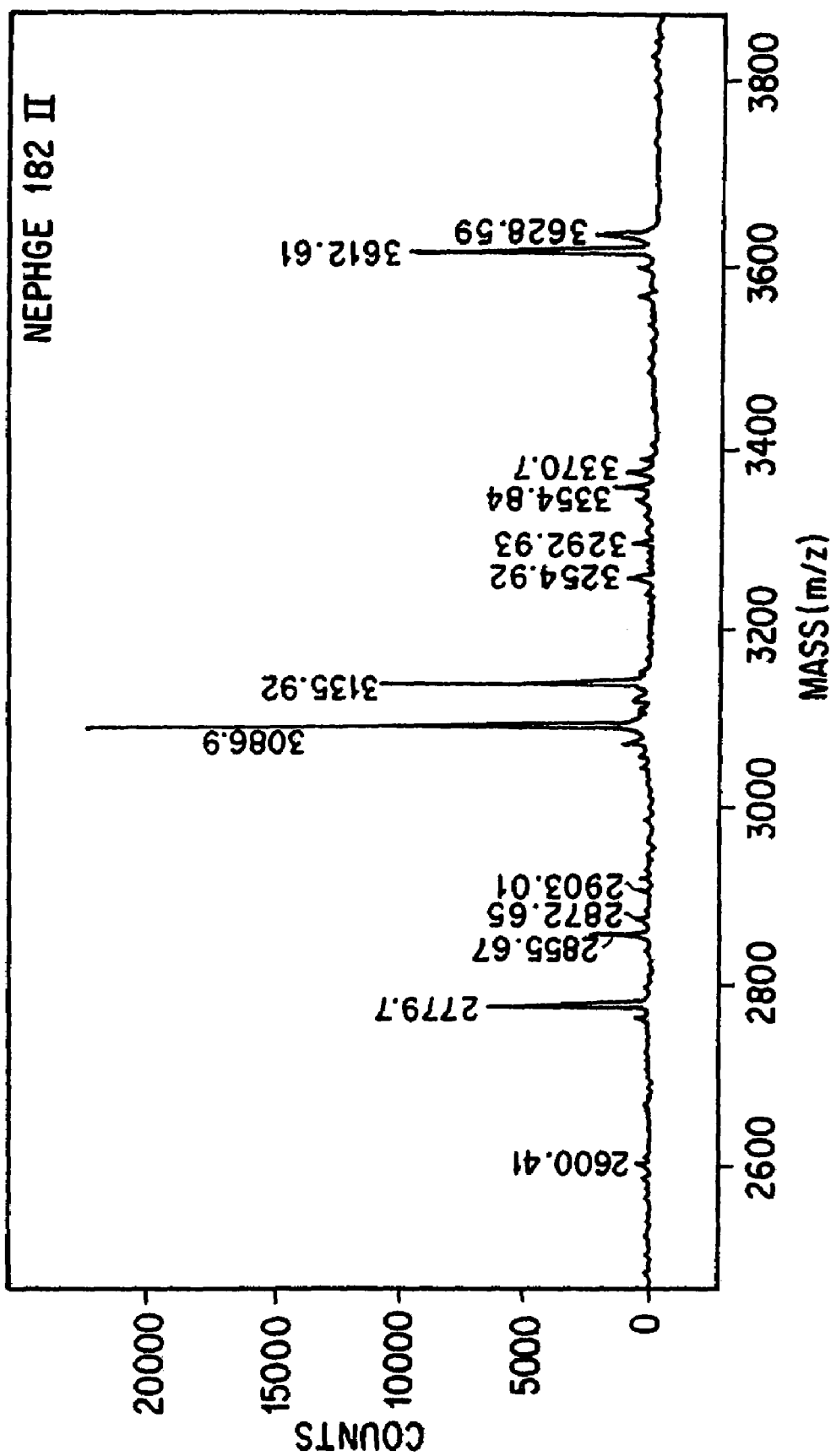
Figure 36:
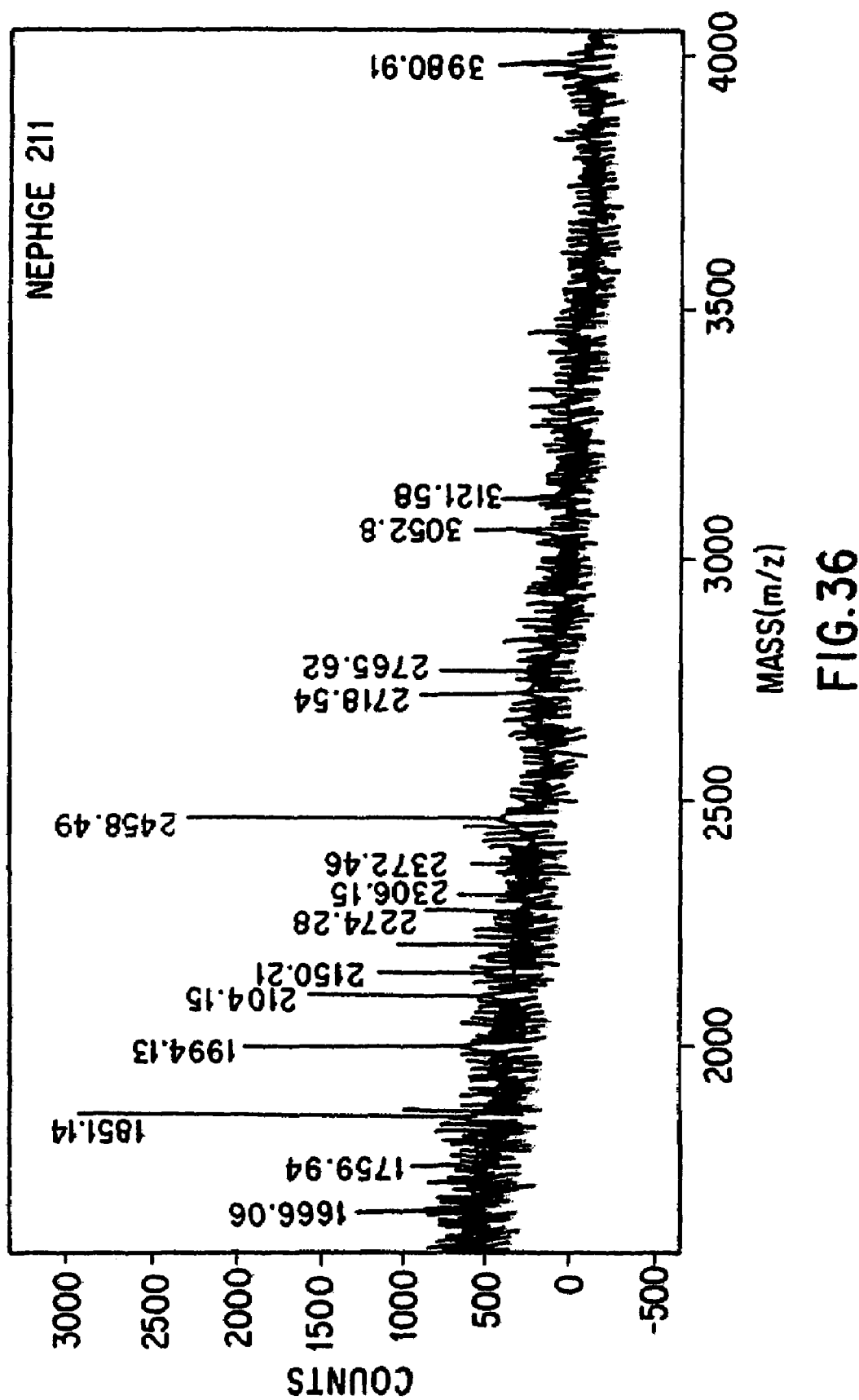
FIG. 36 is the mass spectroscopy spectrum for a novel diabetes-mediating protein, termed "NEPHGE Spot No. 211," having a molecular weight of 47,925 daltons and a pI of 7.28, determined as indicated.
Figure 37:
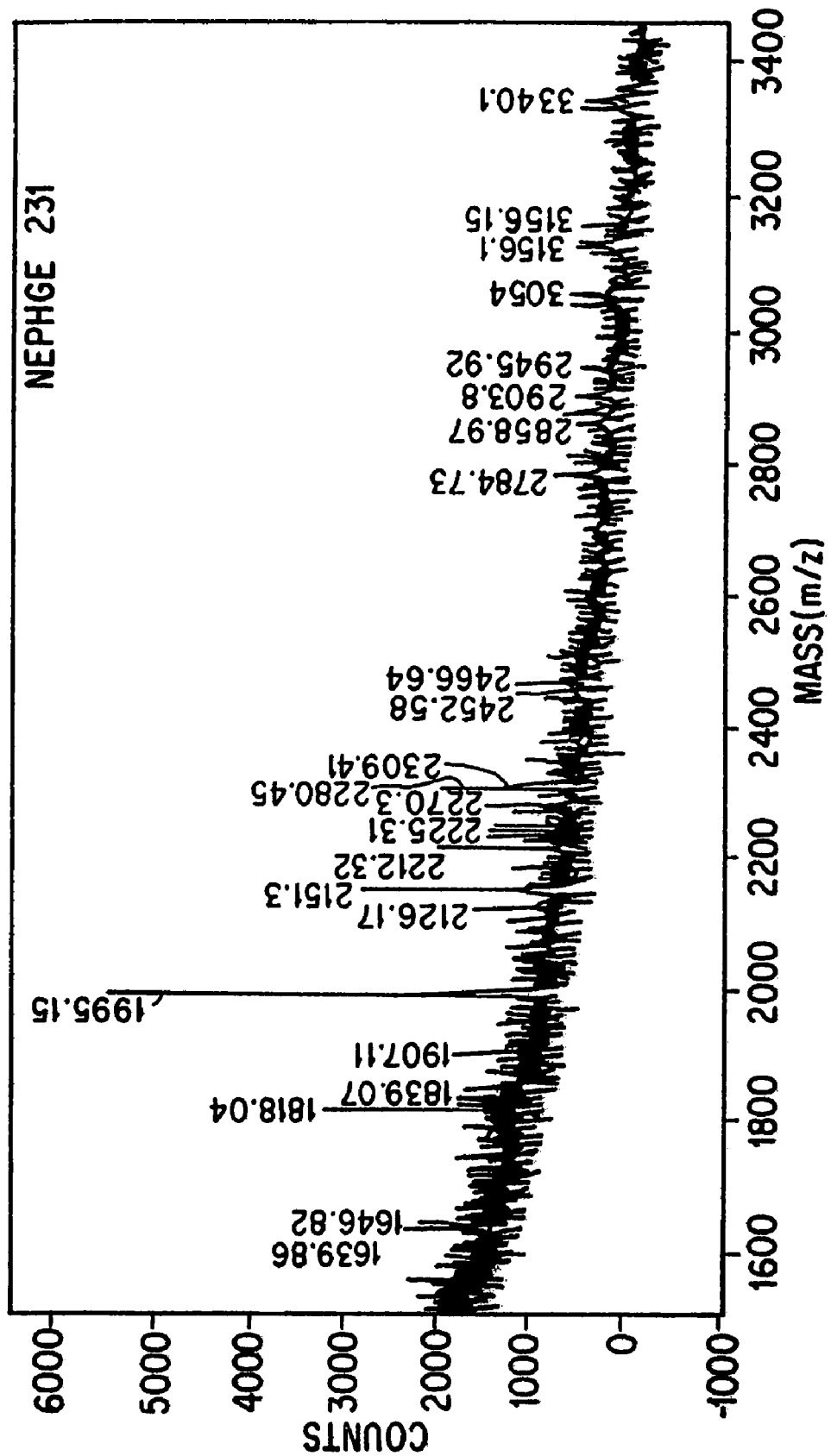
FIG. 37 is the mass spectroscopy spectrum for a novel diabetes-mediating protein, termed "NEPHGE Spot No. 231," having a molecular weight of 44,362 daltons and a pI of 8.34, determined as indicated.
Figure 38:
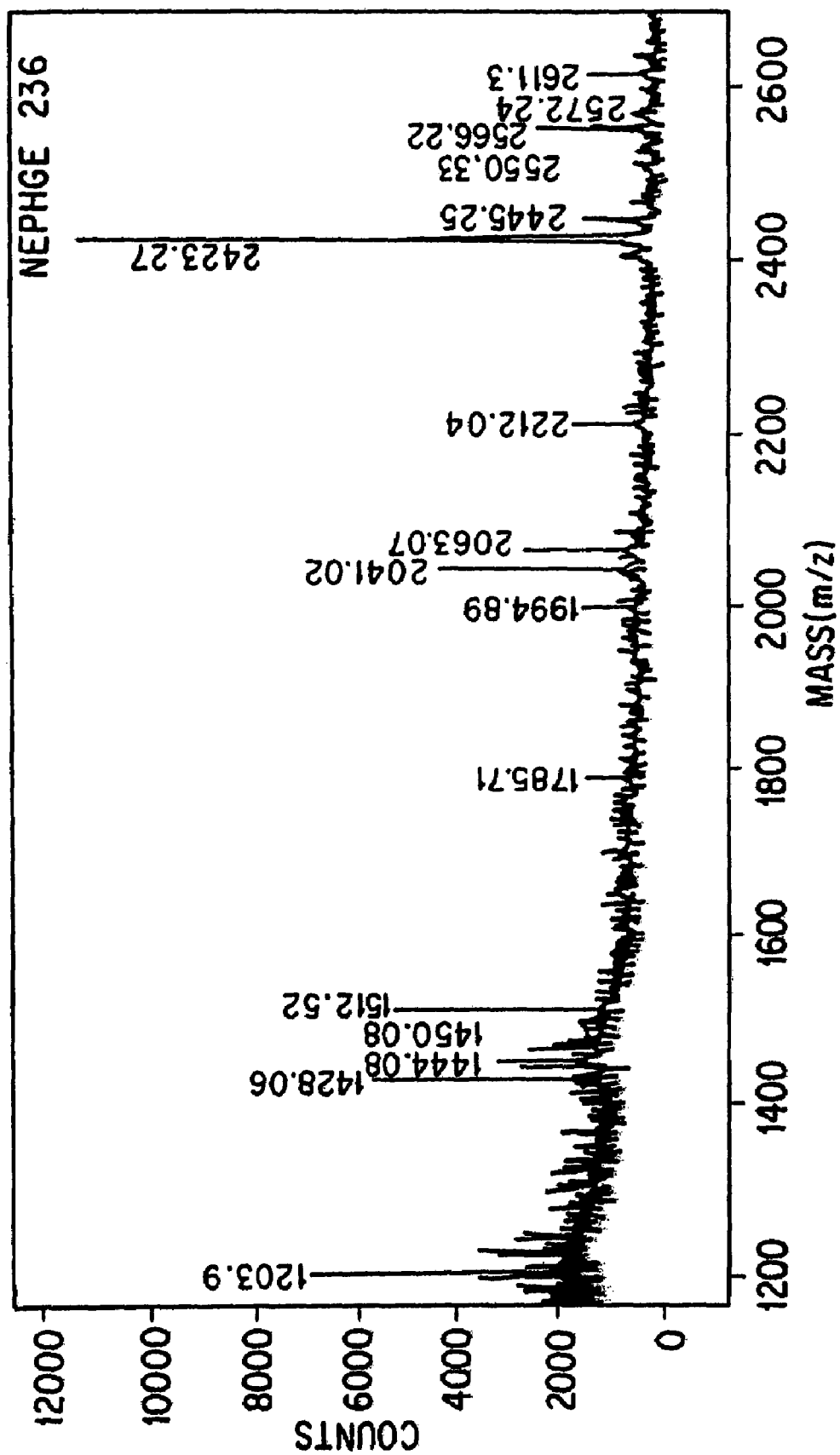
FIG. 38 is the mass spectroscopy spectrum for a novel diabetes-mediating protein, termed "NEPHGE Spot No. 236," having a molecular weight of 43,162 daltons and a pI of 7.90, determined as indicated.
Figure 39:
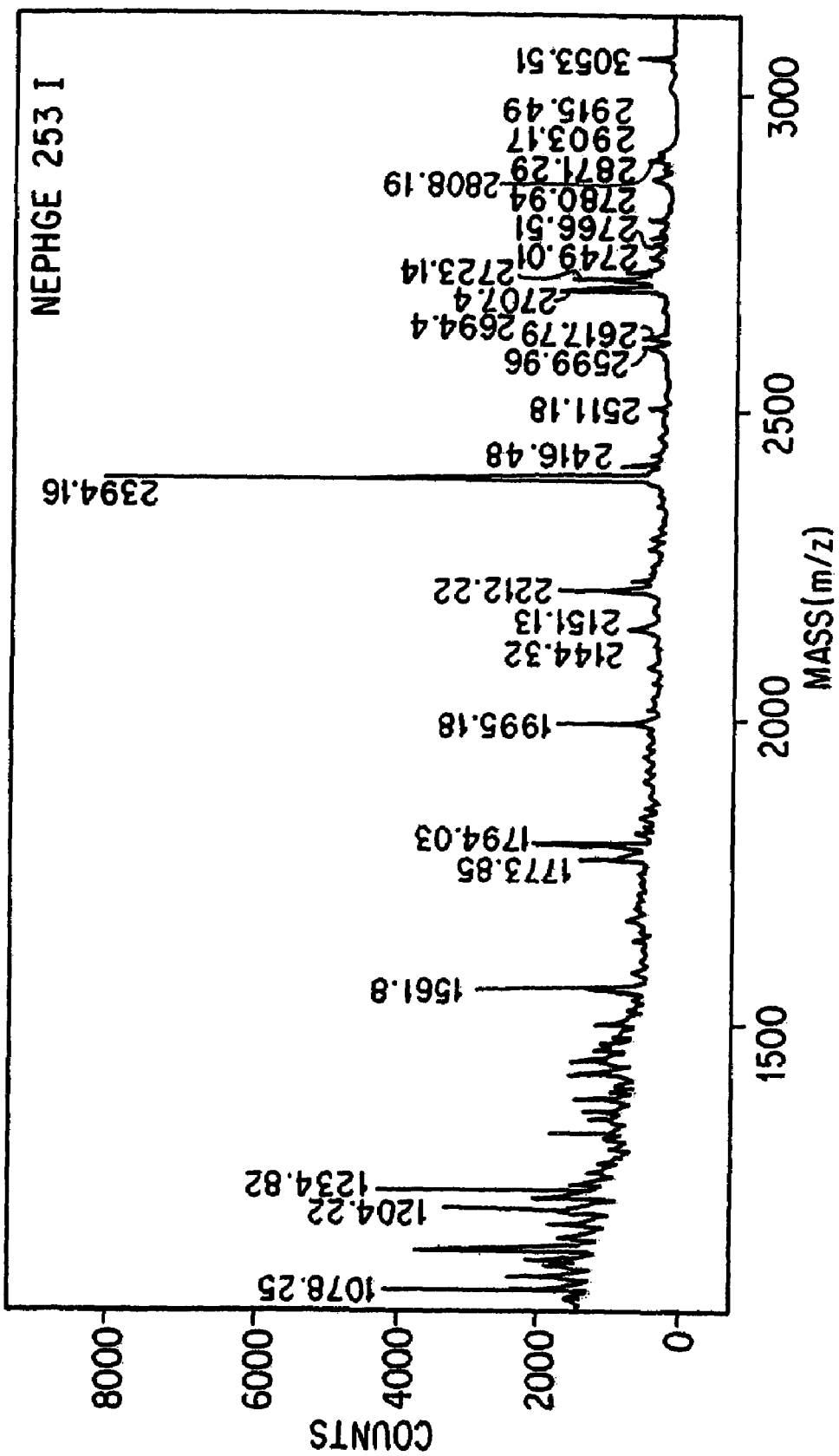
FIGS. 39-40 are the mass spectroscopy spectrum for a novel diabetes-mediating protein, termed "NEPHGE Spot No. 253," having a molecular weight of 39,106 daltons and a pI of 9.05, determined as indicated.
Figure 40:
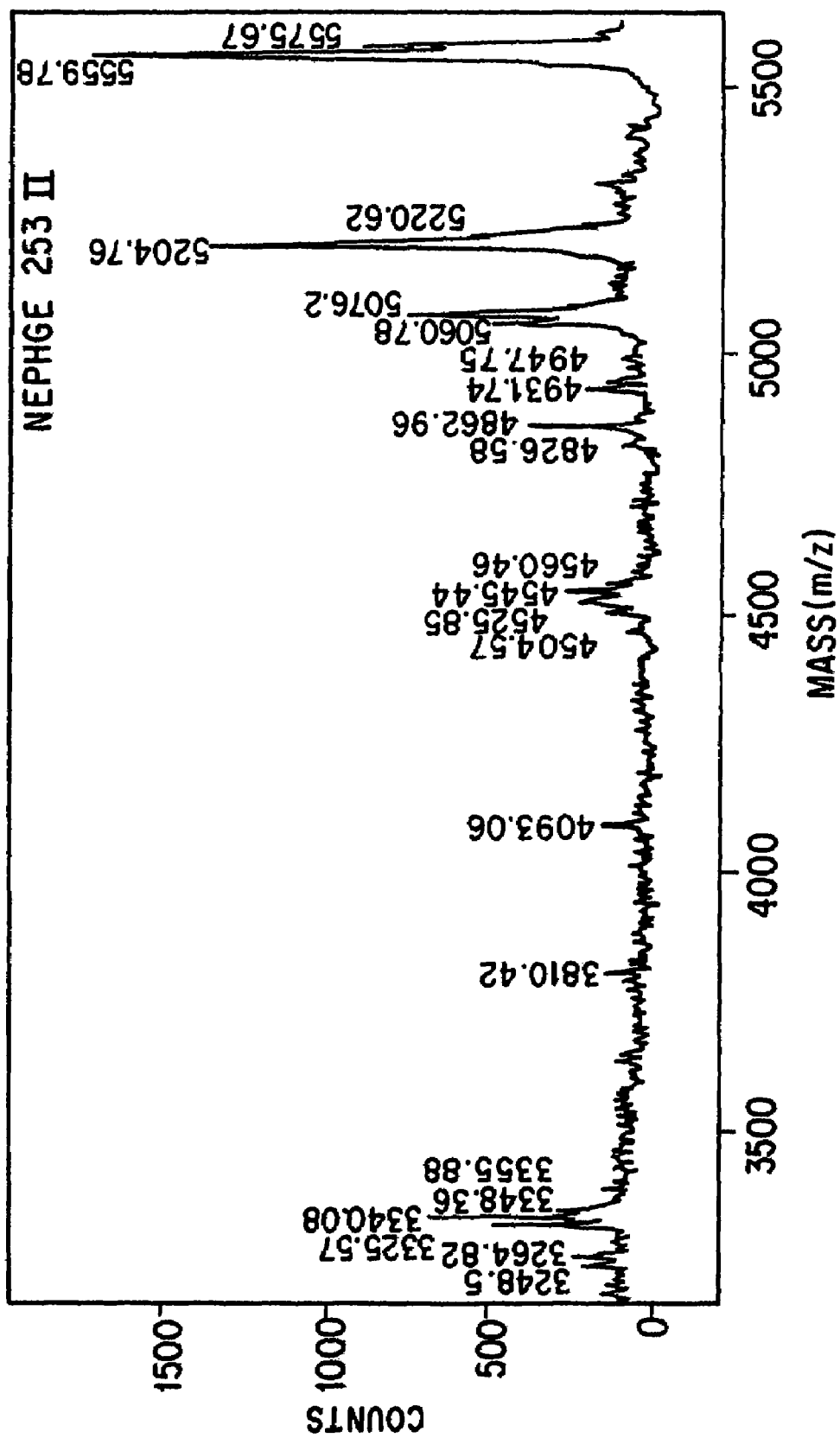
Figure 41:
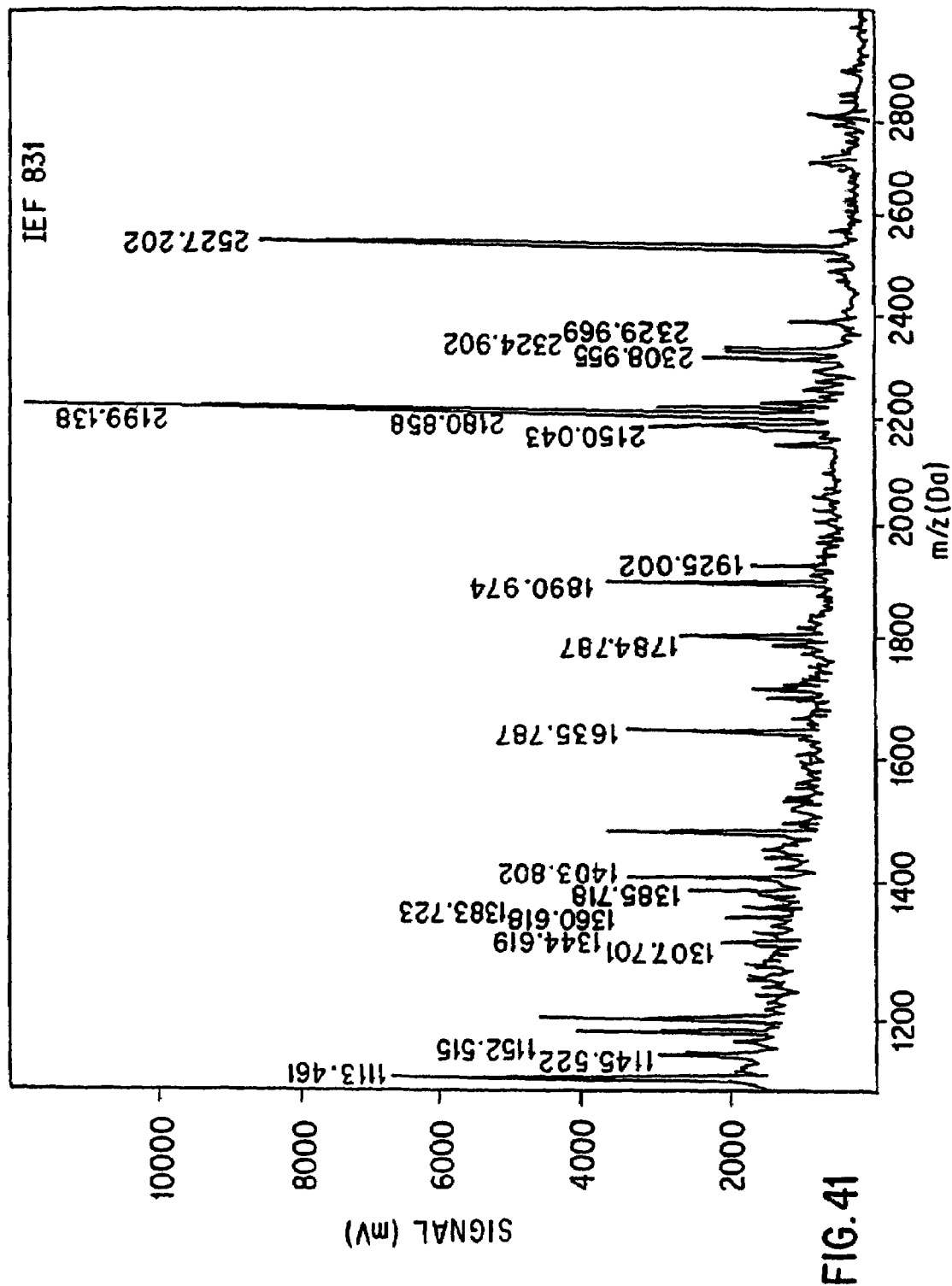
FIG. 41 is a mass spectroscopy spectrum for a novel diabetes-mediating protein, termed "IEF Spot No. 831," having a molecular weight of 34,600 daltons and a pI of 4.76, determined as indicated.
Figure 42:
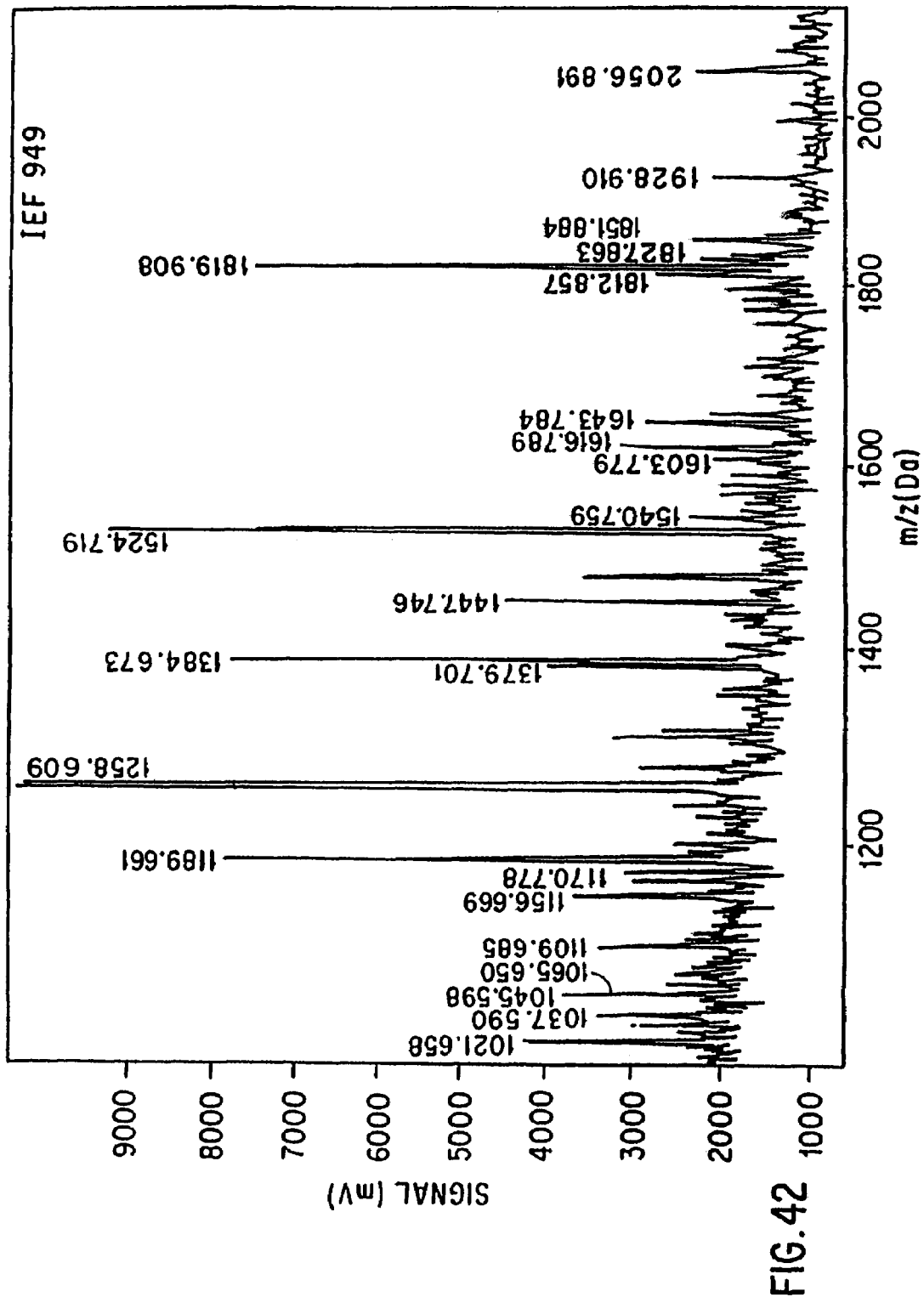
FIGS. 42-43 are the mass spectroscopy spectrum for a novel diabetes-mediating protein, termed "IEF Spot No. 949," having a molecular weight of 26,800 daltons and a pI of 4.49, determined as indicated.
Figure 43:
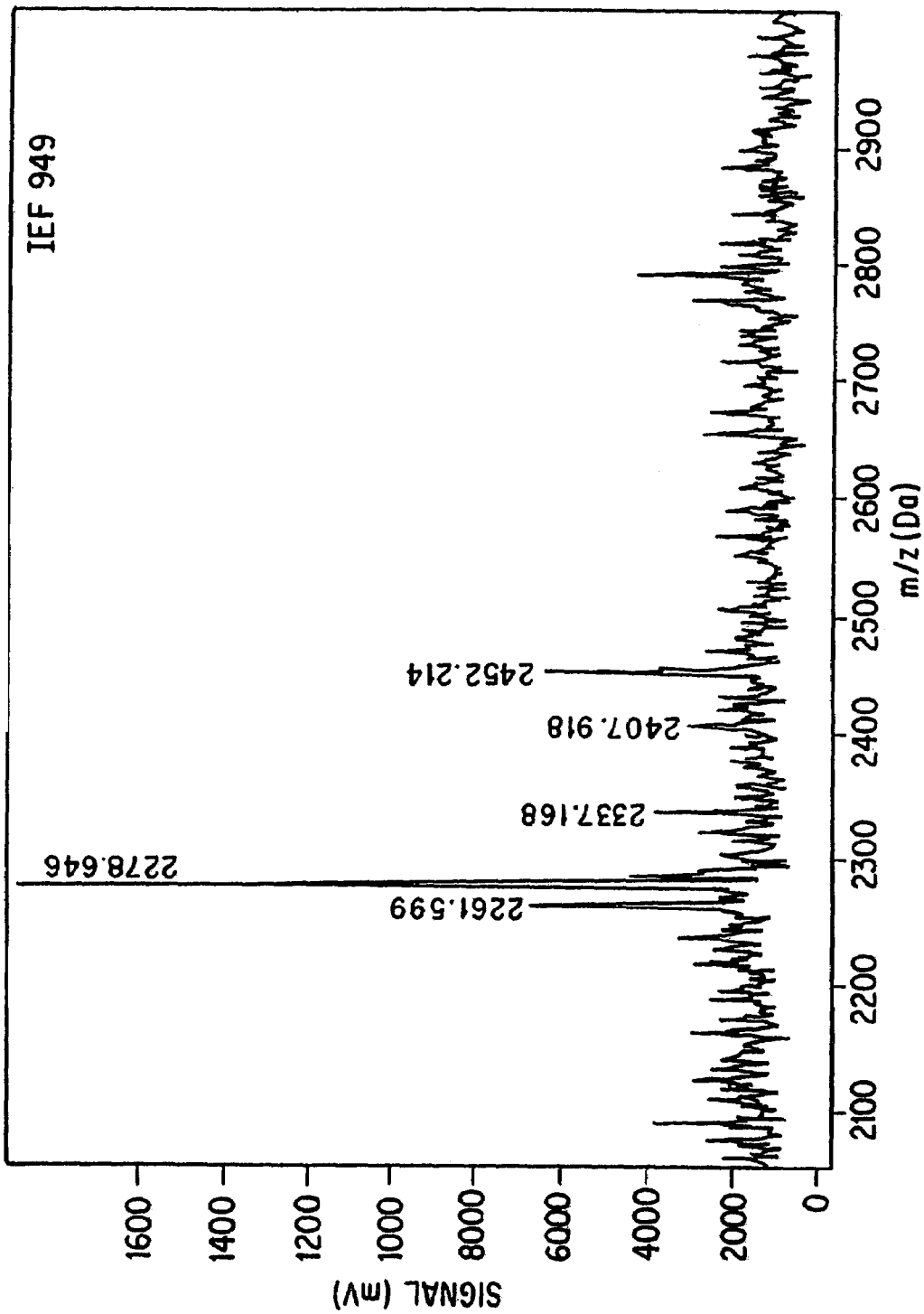

High resolution two-dimensional (2D) gel electrophoresis may be used to separate approximately 2500 protein spots, each spot corresponding to a protein according to molecular weight and pI. A computerized 2-D gel database of 1373 WF rat islet proteins has recently been reported (Andersen et al. *Diabetes* 44:400-407 (1995)) with a qualitative reproducibility of 81% (FIGS. 1A-1B). IL-1β has been shown to induce changes in the expression of 82 protein in BB-DP islet cells incubated in vitro. in vitro incubation of BB-DP islets taken from animals after the onset of diabetes shows that 33 of the 82 proteins determined to respond to IL-1β show significant changes in expression at the onset of diabetes.

Based on the results of 2D gel analysis and peptide sequencing or mass spectroscopy analysis, several candidate diabetes-mediating proteins have been identified (Table 1) and cloned from rat and human islet cells, including iNOS, mortalin, and galectin-3 (Madsen et al. in *Insulin secretion and pancreatic B cell research*, P. R. Flatt & S. Lenzen, eds., Smith-Gordon, USA, pp. 61-68 (1994)). Manganese superoxide dismustase (MnSOD) has been transfected into β-cells and whole islets of Langerhans with the use of adenovirus mediated gene transfer and expression. Transfection includes the generation of stable or transiently transfected cells.

Following transfection, subcloning, and establishment of stable RIN clones expressing the coding region or antisense-fractions of the protein of interest under the control of a CMV or insulin promoter, the diabetes-mediating protein of interest is functionally characterized. Preliminary results show a 100% transduction in RIN cells and up to 70% in isolated islets. Initially, the increased or decreased expression of the protein in the transfected cells is characterized in vitro by measurement of NO production, insulin secretion, and/or cytotoxicity. Furthermore, cell cycle and mitochondrial activity may be determined by FACS analysis (Mandrup-Poulsen et al. *Diabetes/Metabolism Reviews* 9:295-309 (1993)) and semiquantitative analysis of gene expression characterized by multiplex PCR (Nerup et al. *Anales Espanoles Pediatria* 58:40-41 (1994)). Additionally, secondary cellular effects of the over- or under-expression of the protein as well as post-translational modification may be characterized by 2D-gel electrophoresis of the transfected cells. This analysis allows a distinction to be made between primary and secondary effects in the IL-1β induced changes in protein expression pattern.

To establish IL-1β induced changes in islet cells, NO production and insulin release were measured in BB-DP islets of Langerhans in vitro after IL-1β exposure and high resolution twodimensional gel electrophoresis to detect protein changes resulting from IL-1 exposure (Example 2). NO production and insulin release in control islets was similar to that observed in WF islets. IL-1β inhibited NO production 4.4-fold and insulin release 3.4-fold. 2D gel analysis showed that IL-1β changed the expression of 82 proteins-22 proteins were up-regulated and 60 down regulated.

High resolution 2DGE was also used to detect protein changes in BB-DP islet syngrafts transplanted into 30 day old BB-DP rats (Example 3). In BB-DP islet syngrafts from newly onset diabetic BB-DP rats, but not in WF islet syngrafts, 15 of these 82 proteins were found to change level of expression (Example 4).

The IL-1β induced changes in protein expression in vitro were compared to protein changes in the process of disease occurrence in BB-DP islet syngrafts (Example 4) or in BB-DP islet allograft rejection (Example 6). In BB-DP islet syngrafts from newly onset diabetic BB-DP rats, but not in WF islet syngrafts 15 of these 82 proteins were found to change level of expression.

Proteins exhibiting altered expression with diabetes onset in syngrafted islets were further characterized (example 5). One of the altered protein spots was identified by amino acid sequencing to have high homology to the heat shock 70 protein (mortalin), which has been demonstrated to be involved in cellular mortality and apoptosis following translocation of this constitutively expressed protein from a perinuclear to the cytoplasmic region (Wadhwa et al. *J. Biol. Chem.* 268:6615 and 268:22239 (1993)). Based on the amino acid sequence, mortalin cDNA was cloned from rat and human islet for further characterization of its involvement in diabetes development. Over-expression of mortalin in rat insulinoma (RIN) β cells under a CMV promoter was lethal to β cells.

Another diabetes-mediating protein was identified as galectin-3. Galectin-3 (gal-3) was identified in 2D gels as spots 1S (phosphorylated twice), 16 (phosphorylated once), and 19 (non-phosphorylated) (Andersen et al. *Diabetes* 44:400-407 (1995)) (Example 5). Gal-3 is a protein involved in islet development and inhibition of apoptosis. Using the nucleotide sequence, gal-3 was cloned from rat and human islets, subcloned and expressed in RIN cells after selection for stable clones. RIN cells expressing gal-3 exhibited an increased metabolic activity and proliferative rate, and became more resistant to the negative effect of cytokines. The in vivo effect of gal-3 expression was studied by transplanting 200 neonatal islets to 30 day old diabetes prone Bio-Breeding rats (BB-DP) (Example 8).

Further work using the NIGMS (National Institute of General Medical Science) human/rat somatic cell hybrid mapping panel # 2 and primers from intron 2 of the gal-3 gene, has mapped gal-3 to chromosome 14. Using the same primers, a P1 clone was obtained from GenomeSystems, Inc. to use for FISH. Initial FISH results obtained with 48 measurements showed 6.2% localize to the 14q13 region, 54.2% to the 14q21 region, and 39.6% to the 14q22 region, which indicate a distal location in the 14q21.3 region.

Inducible nitric oxide synthase (iNOS) was cloned (Karlsen et al. *Diabetes* 44:753 (1995)). The iNOS gene was mapped to mouse chromosome 11, which is in the middle of the idd4 region; a region identified as a diabetes-linked region in the diabetes prone NOD mouse (Gerling et al. *Mammalian Genome* 5:318 (1994)). When expressed as a recombinant protein in fibroblasts, it was found that the recombinant iNOS was enzymatically active.

Manganese superoxide dismutase (MnSOD) was identified as a down regulated protein by 2D gel analysis. The expression of MnSOD was further characterized in (3 and islet cells in vitro and in vivo following adenovirus transduction and transplantation. Mitochondrial isocitrate dehydrogenase was identified as a diabetes-mediating protein.

Changes in protein expression associated with allograft rejection were also determined. Neonatal BB-DP islet cells transplanted into 30 day old WK rats were retrieved after 12 days, and protein expression determined (Example 6). It was found that BB-DP islet allografts in WK rats but not in WF islet syngrafts 9 of 82 proteins were found to change level of expression.

Both the syn-and allografted BB-DP islets were compared to non-grafted BB-DP islets with regard to the proteins found to change expression levels during IL-1 exposure of the BB-DP islets in vitro. To control for protein-changes induced by the grafting procedure, 200 neonatal WF islets were grafted to 30 day old WF rats. Grafts were retrieved 48 days after transplantation corresponding to the mean time of onset of diabetes in the colony and in the syngrafted BB-DP rats. The grafts were processed and analyzed as described for comparison with WF control islets with regard to the 105 proteins previously found to be changed during IL-1 incubation. This was done to identify protein changes inducible both by IL-1 and islet syngrafting, as well as to identify rejection-specific proteins.

To further determine a potential role of these proteins in the diabetes pathogenesis, and to identify therapeutic compounds and compounds which induce the expression of therapeutic compounds, transgenic animals carrying the gene encoding the candidate protein and able to express the candidate protein under tissue-specific promoters are generated. The transgenic animals of the invention express candidate proteins under specific promoters such as the insulin, amylin, CMV, or HLA promoters.

Initially, a study was conducted to determine the optimal conditions for adenoviral-mediated gene transfer to the islets of Langerhans in the absence of vector-induced toxicity. As described in Example X, adenoviral mediated transduction of islets resulted in dose-dependent efficient gene transfer with stable transgene expression in the absence of toxicity.

EXAMPLES

The following examples are put forth so as to provide those of ordinary skill in the art with a complete disclosure and description of how to make and use the chimeric genes, transgenic mice and assays of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials and Methods

Reagents. Ketamin was purchased from Park-Davis (Barcelona, Spain), xylazin from Bayer (Leverkusen, Germany), and Temgesic® from Reckitt and Colemann (Hull, UK). RPMI 1640, Hanks' balanced salt solution (HBSS), and DMEM were purchased from Gibco, Paisley, Scotland. RPMI 1640 contained 11 mmol D-glucose, and was supplemented with 20 mM HEPES buffer, 100,000 IU/l penicillin and 100 mg/l streptomycin. Authentic recombinant human IL-1β was provided by Novo Nordisk Ltd. (Bagsvaerd, Denmark) having a specific activity of 400 U/ng.

Other reagents used: 2-mercaptoethanol, bovine serum albumin (BSA), Tris HCI, Tris base, glycine, (Sigma, St. Louis, USA); trichloracetic acid (TCA), phosphoric acid, NaOH, glycerol, n-butanol, bromophenol blue, sodium nitroprusside (SNP), $H_3PO_4$ and $NaNO_2$ (Merck, Darmstadt, Germany); filters (HAWP 0.25 mm pore size) (Millipore, Boston, USA); RNAse A, DNAse I (Worthington, Freehold, N.J., USA); [$^{35}$S]-methionine (SJ 204, specific activity: >1.000 Ci/mmol, containing 0.1% 2-mercaptoethanol), Amplify® (Amersham International, Amersham, UK); urea (ultra pure) (Schwarz/Mann, Cambridge, Mass., USA); acrylamide, bisacrylamide, TEMED, ammonium persulphate (BioRad, Richmond, Calif., USA); ampholytes: pH 5-7, pH 3.5-10, pH 7-9, pH 8-9.5 (Pharmacia, Uppsala, Sweden); Nonidet P-40 (BDH, Poole, UK); ampholytes: pH 5-7 and sodium dodecyl sulphate (Serve, Heidelberg, Germany); agarose (Litex, Copenhagen, Denmark); ethanol (absolute 96%) (Danish Distillers, Aalborg, Denmark); methanol (Prolabo, Brione Le Blanc, France); acetic acid (technical quality, 99% glacial) (Bie & Berntsen, Arhus, Denmark) and X-ray film (Curix RP-2) (AGFA).

Animals. Thirty (28-32) day old BB/Wor/Mol-BB2 (BB-DP), Wistar Furth (WF) and Wistar Kyoto (WK) rats were purchased from Møllegården, L1. Skensved, Denmark. At Møllegården and in the animal facilities at the Steno Diabetes Center/Hagedorn Research Institute (Gentofte, Denmark) the BB-DP rats were housed separately in a specific pathogen-free environment. All rats were housed under controlled conditions of light (light on from 6:00 am to 6:00 pm), humidity (60-70%) and temperature (20-22° C.) from five days prior to transplantation until sacrifice. The rats were offered a standard rat chow (Altromin, Chr. Petersen A/S, Ringsted, Denmark) and free access to tap water. Four to five day-old BB-DP and WF rats were picked up at Møllegården in the morning on the day of islet isolation, and transported in animal transport boxes.

Transplantation procedure and graft retrieval. The neonatal islets were transplanted under the kidney capsule of 28-32 day-old recipient rats under sterile conditions as previously described (Korsgren et al. *J. Clin. Invest.* 75:509-514 (1990)). Since diabetes incidence is similar in male and female BB-DP rats (Pries et al. *Frontiers in Diabetes Research* 8:19-24 (Shafrir, E., ed.), Smith-Gordon, London (1991) both sexes were equally used. To reduce a possible risk of graft rejection due to any gender-related incompatibility, male islets were transplanted to male recipients and female islets to female recipients (Steiner et al. *Electrophoresis* 16:1969-1976 (1995)). Two-hundred (range: 187-215) islets were hand-picked using a 10 ml Transpferpettor (Brand, Germany) pipette. The islets were allowed to sediment, and as much supernatant as possible was removed prior to the transplantation of a volume of 1-2 ml. The recipient rats were weighed, and blood glucose (BG) was measured. The rats were then anesthetized with ketamin (8.75 mg/100 g) and xylazin (0.7 mg/100 g) ip. A small incision was made over the left kidney, the kidney was lifted forward, and a small incision using a knife was made. A pocket using a blunt instrument was gently made in the capsule. The islets were placed under the capsule towards the lower kidney pole. The muscle and skin were sutured, the rats allowed to recover in a cage in the operating facility and given Temgesic (0.01 mg) sc in the neck before returning to the animal facility. The rats were given Temgesic twice daily for 3 days post transplantation. Blood glucose (BG) was measured every third day. The rats were killed by cervical dislocation and immediately afterwards the grafted kidneys were removed. The grafts were carefully dissected from the kidneys and capsules under a microscope and placed in HBSS.

Graft and islet labeling. The grafts were labeled immediately after retrieval. Cultured islets were labeled after 24 h of incubation with or without IL-1. Grafts and islets were washed twice in HBSS and labeled for 4 h at 37° C. in 200 ml methionine-free Dulbecco's modified Eagle's medium (DMEM) with 10% NHS dialyzed for amino acids, and either 330 mCi [35S]-methionine for the grafts or 200 mCi [35S]-methionine for the islets. To eliminate 2-mercaptoethanol, [35S]-methionine was freeze-dried for at least 4 h before labeling. After labeling, the grafts and islets were washed three times in HBSS, the supernatant was removed and the tissue immediately frozen at −80° C.

Sample preparation. The frozen grafts were crushed in a mortar. The grafts and islets were resuspended in 100 ml DNAse I/RNAse A solution and lysed by freeze-thawing twice. After the second thawing, the samples were left on ice for 30 min for the digestion of nucleic acids and then freeze dried overnight. The samples were dissolved by shaking in 120 ml lysis buffer (8.5 M urea, 2% Nonidet P-40, 5% 2-mercaptoethanol and 2% ampholytes, pH range 7-9) for a minimum of 4 h.

Determination of [35S]-methionine incorporation. The amount of [35S]-methionine incorporation was quantitated by adding 10 mg BSA (0.2 mg/ml $H_2O$) as a protein-carrier to 5 ml of a 1:10 dilution of each sample in duplicate, followed by 0.5 ml of 10% TCA. This was left to precipitate for 30 min at 4° C. before being filtered through 0.25 mm HAWP filters. The filters were dried and placed into scintillation liquid for counting.

2-D gel electrophoresis. The procedure has been described earlier (O'Farrell et al. *Cell* 12:1133-1142 (1977)). Briefly, first dimension gels contained 4% acrylamide, 0.25% bisacrylamide and ampholytes. Equal numbers of counts (106 cpm) of each sample were applied to the gels. In case of lower amounts of radioactivity it was necessary to regulate the exposure time of the gel so that comparable total optical densities were obtained. The samples were analyzed on both isoelectric focusing (IEF; pH 3.5-7) and non-equilibrium pH-gradient electrophoresis (NEPHGE; pH 6.5-10.5) gels. Second dimension gels contained 12.5% acrylamide and 0.063% bisacrylamide and were run overnight. After electrophoresis, the gels were fixed and treated for fluorography with Amplify® before being dried. The gels were placed in contact with X-ray films and exposed at −70° C. for 3 to 40 days. Each gel was exposed for at least 3 time periods to compensate for the lack of dynamic range of X-ray films.

Determination of MW and pI. Molecular weights of the proteins were determined by comparison with standard gels. The pIs for the individual proteins on the gels were determined by the use of pI calibration kits. Landmark proteins were identified on gels by one or several of the following techniques: immunoblotting, immunoprecipitation, micro sequencing or peptide mapping.

Computer analysis of fluorographs. Computer analysis was performed using the BioImage® program (version 6.1) on a Sunsparc workstation. First, the fluorographs were scanned and spots identified and quantitated by the BioImage® program. Next, anchor points were placed on the gel (same spot in each gel was assigned the same anchor point), and the computer was asked to match the gels. After computer matching, manual editing was performed to ensure identification, correct matching of computer found spots and quantitation of spots not found initially by the computer program. Finally, data were exacted for calculations in the Quatro Pro® spreadsheet (Borland version 4.0). To avoid the presence of duplicate spots in the IEF and NEPHGE subgroups, overlapping spots in either the basic part of IEF gels or in the acidic part of NEPHGE gels were omitted from analysis.

Statistical analysis. Student's t test was applied and P<0.01 was chosen as level of significance.

Example 2

In Vitro Nitrite and Insulin Determinations

To investigate IL-1 induced protein changes in BB-DP islets, 150 neonatal BB-DP rats islets were incubated for 24 hours with or without 150 pg/ml of IL-1, after which the medium was sampled for nitrite and insulin measurements. Two dimensional gel analysis of the islets was performed as described below, and fluorographs of the islets were analyzed on computer (see below, n=3 for each group) and compared with the previously established protein database of IL-1 exposed WF rat islets.

Islet isolation and culture. Islets from pancreata of four to five day old inbred BB-DP and WF rats were isolated after collagenase digestion as described by Brunstedt et al. in *Methods in Diabetes Research*, Vol. 1, Wiley & Sons, New York, pp. 254-288 (1984), specifically incorporated herein by reference. After 4 days of preculture in RPMI 1640+10% fetal calf serum, islets were cultured as follows: 150 BB-DP islets were incubated for 24 h in 37° C. humidified atmospheric air in 300 ml RPMI 1640+0.5% normal human serum (NHS) with or without the addition of 150 pa/ml IL-1β. In separate series of experiments, 200 BB-DP or WF islets were incubated for 24 h in 300 ml RPMI 1640+0.5% NHS before grafting.

Nitrite and insulin measurements. Nitrite was measured by Griess reagents as previously described (Green et al. *Anal. Biochem.* 126:131-138 (1982)). The detection limit of the assay was 1 mmol/l, corresponding to 2 pmol/islet. The nitrite level of the corresponding medium without islets was subtracted if the value of the islet-free medium was above the detection limit. The experiments were run in the same assay. Intra- and interassay coefficients of variation calculated from 3 points on the standard curve were: 1 mmol/l: 1.6%, 16.3%; 10 mmol/l: 1.6%, 15.3%; 25 mmol/l: 1.5, 17.0%. Insulin was measured by RIA (Yang et al. *Proc. Natl. Acad. Sci.* 93:6737-6742 (1996)). The detection limit was 35 fmol/ml. Intra- and interassay coefficients of variation between 3 known controls were A: 5.4%, 12.5%; B: 3.6%, 10.2%; C: 3.1%, 9.4%.

Results. To ensure comparability in terms of function (accumulated insulin release) and response to IL-1 between BB-DP islets and the WF islets previously used for 2-D gel analysis (Andersen et al. supra (1995)), NO production and insulin release were measured after 24 hours of incubation with or without IL-1. The basal insulin release and NO production were similar to data from WF islets (basal insulin release (WF islets) 3.3±0.5 versus (BB-DP islets) 2.0±1.1 pmol*islet-1*24 h-1, basal NO production <2 pmol*islet-1*24 h-1, for both BB-DP and WF islets. IL-1 inhibited accumulated islet insulin release by 3.4 fold and increased NO production by 4.4 fold, similarly to results obtained using neonatal WF rat islets (IL-1 induced NO production: (WF islets) 9.29±1.21 versus (BB-DP islets) 8.91±1.05 pmol*islet-1*24 h-1 and insulin release: (WF islets) 1.4±0.3 versus (BB-DP islets) 0.6±0.6 pmol*islet-1*24 h-1.18.19).

Analysis of fluorographs from BB-DP rat isles ±IL-1. In a computer based analysis of two dimensional gels of neonatal BB-DP rat islet homogenates a total of 1815 (1275 IEF and 540 NEPHGE) proteins were found in 3 of 3 12.5% acrylamide gels. In neonatal BB-DP rat islets incubated with IL-1 for 24 hours, 1721 (1171 IEF and: 550 NEPHGE) were found in 3 of 3 gels. IL-1 was found to significantly change the expression level of 82 proteins compared to control islets ($p<0.01$); 60 proteins were decreased and 22 increased in expression level ($p<0.01$) (Table 1).

Example 3

Animal Transplantation Model

Experiment 1. Initially, to create a synchronized model for the investigation of the cellular and molecular events occurring during development of IDDM, 200 neonatal BB-DP rat islets were isolated and transplanted under the kidney capsule of 30 day old BB-DP rats. Blood glucose was measured every third day, and the incidence of diabetes determined.

The rats were sacrificed 7, 12, 23, 37, 48, and 173 days after transplantation or at onset of diabetes (n=6 in each group). Grafts were double stained for insulin and one of the following MHC class I, II, αβ-TCR, CD4, CD8, or ED1. Staining was expressed as percentage of total graft area (insulin) or number of stained cells per $mm^2$. The host islets in situ were stained in the same way and expressed as percent inflamed islets of the total number of islet cells. Statistical analysis was conducted with Spearman Rank Correlation and Mann-Witney.

Results. The incidence of diabetes (75%) or day of onset of diabetes (69±25 days) did no differ significantly from non-transplanted BB-DP rats. A 2-fold increase in the number of infiltrating cells in both graft and islets in situ was seen days 12 and 37. Forty-eight days after transplantation, the number of cells increased in both graft and islets in situ for the rats developing diabetes ($p<0.04$) compared to day 37 in prediabetic and non-diabetic rats at day 48, respectively. Graft insulin staining area was 80-90% in the nondiabetic and 30% of total graft area in the diabetic grafts with an inverse relationship between insulin content and cellular infiltrate. For all cell types and at all timepoints studied, a positive correlation was found between the percentage of infiltrated islets in the host pancreatic slides and the number of infiltrating cells in the graft from the same animals ($p=0.002-0.00001$; $r=0.4-0.7$).

Experiment 2. 200 neonatal BB-DP rat islets were transplanted under the kidney capsule of 30 day old BB-DP rats. Allogeneic transplantation from Wistar Furth islets to Wistar Kyoto rats was similarly conduced as a control.

The grafted islets did not affect IDDM incidence or time of disease onset. On the day of diabetes onset (78±5 days) and on day 17 in the control WK animals, the grafts were excised for immunohistochemistry and [$^{35}$S]-methionine labeling.

Results. Immunohistochemical examination of the grafts from diabetic BB rats demonstrated massive inflammation with MHC class I positive cells (1982/$mm^2$±534), macrophages (661/$mm^2$±406), T-helper cells (1331/$mm^2$±321), cytotoxic T-cells (449/$mm^2$±117), and insulin positive cells reduced to 33-66$ of the transplant. Allogeneic transplant controls showed fibrosis, less infiltration of mononuclear cells, MHC class II positive cells (152/$mm^2$), MHC class I positive cells (48/$mm^2$), macrophages (172/$mm^2$), T-helper cells (254/$mm^2$), cytotoxic T-cells (42/$mm^2$), and insulin content of 100% in the remaining cells.

Computerized analysis of 2D gels showed a greater than 2-fold increase in the expression of 18 of the 33 proteins altered in vitro by IL-1 exposure. 14 were specific to the syngeneic transplants in the BB-DP animals. 8 proteins specifically changed level of expression.

Example 4

Changes in Protein Expression Induced by Diabetes Onset

To investigate protein changes in BB-DP islet syngrafts during disease occurrence, 200 neonatal BB-DP rat islets were grafted to 30 day old BB-DP rats. Grafts were retrieved at onset of diabetes, defined as BG>14 mmol/l for two consecutive days, n=5, for labeling, two dimensional gel electrophoresis and computer based comparison with non-grafted BB-DP islets.

Analysis of fluorographs from syngeneic islet-grafts from newly onset diabetic BB-DP rats. In BB-DP islet syngrafts from newly onset diabetic BB-DP rats, computer analysis showed 1818 proteins (1259 IEF and 557 NEPHGE) present in 5 of 5 gels. (These data are preliminary proteins present in both islets in vitro and grafts changed expression level (64 were increased and 131 decreased in expression level) when compared to control neonatal BB-DP rat islets ($p<0.01$, data not shown)). Seventy-one of the eighty-two proteins that changed level of expression in BB-DP rat islets after IL-1 incubation in vitro were re-identified in the graft. Of the 71 re-identified proteins 33 significantly changed expression levels (4 up- and 29 down-regulated) in the islet syngrafts at onset of diabetes (Table 2).

Analysis of fluorographs from islet WF syngrafts. To control for changes in protein expression caused by the grafting procedure per se, WF islet syngrafts were compared to the protein changes caused by IL-1 in WF neonatal islets in vitro. Of the 105 proteins that changed expression level in WF islets incubated with IL-I in vitro, 89 proteins were re-identified whereas 12 were absent in the WF islet grafts (n=3) when compared to the WF control islets. Forty-two of the ninety-three re-identified proteins significantly changed level of expression (27 decreased and 15 increased, $p<0.01$, Table 5). IL-1 induced proteins in vitro specifically seen in islet-grafts during disease occurrence or islet-graft rejection. Proteins that were found to change level of expression in islets after IL-1 incubation in vitro and not found to significantly change level of expression in syngrafted WF islets were denoted specific for disease occurrence if found in syngrafted BB-DP islets or specific for graft-rejection if found in allografted BB-DP islets to WK rats. In syngrafted BB-DP islets 28 proteins and in allografted BB-DP islets 29 proteins changed level of expression (data not shown). Fourteen proteins specifically changed level of expression in BB-DP syngrafts and 8 in BB-DP allografts in WK rats.

Example 5

Characterization of Diabetes-Mediated Proteins

Proteins exhibiting IL-1β-induction of synthesis were analyzed by mass spectrometry and microsequencing as described below. Commercially available protein databases were searched for matches, including SWISS-PROT, PIR, NIH, and GENEBANK.

Microsequencing. Protein spots identified by 2DGE as diabetes-mediated proteins were further characterized by being digested with trypsin in the gel, concentrated, HPLC separated, peak sequenced, and partial sequence compared to known sequences, according to known methods.

Results of Microsequences are as Follows:

Protein 22 (peak 22): A Q Y E E L I A N G (D) (M) (SEQ ID NO:5)

(peak 13): K K P L V Y D E G (K) (SEQ ID NO:6)

Protein 25 (peak 15): L L E X T X X L X (SEQ ID NO:7)

(peak 16): P S L N S X E X (SEQ ID NO:8)

Galectin-3 (peak 22): I E L X E I X (SEQ ID NO:9)

Direct sequencing of one protein (mw 68,700) yielded the following partial sequence: PEAIKGAVVGIDLG (SEQ ID NO: 10) (Table 2: GR75). This protein has high homology to 75 kD glucose regulated protein (GR75, Table 2) (PBP74, P66mot, mortalin); is a constitutive member of hsp70 protein family, not heat-inducible; is ubiquitously expressed in different tissues; comprises a 46 residue leader peptide 75 kD processed to 66 kD; is found in mitochondria; is associated with cellular mortality and with antigen presentation.

One protein was identified as galectin-3, a 27 kD protein which is present in several tissues, and known to have a role as a pre-mRNA splicing factor. The amino acid sequence of human gal-3 is shown in FIG. 5 (SEQ ID NO:4).

Mass spectroscopy. In situ digestion is performed on at least one gel plug including at least one protein spot in at least one gel according to the present invention. Gels are prepared by a modification of the method of Rosenfeld et al. *Anal. Biochem.* 203:173-179 (1992), as described in Fey et al. *Electrophoresis* 18:1-12 (1997), both of which references are herein specifically incorporated by reference. Briefly, gels are quickly stained and destained. The protein of interest is obtained by cutting a gel band containing the protein with a scalpel and storing in eppendorf tubes with UHQ water at −20° C. The protein is digested by washing the gel plug for at least 1 hour in 40% acetonitrile/60% digestion buffer until the coomassie stain is removed. This wash removes coomassie stain, gel buffers, SDS and salts. If necessary the wash can be repeated. The gel plug is then dried in a vacuum centrifuge for 20-30 min. until the plug shrinks and becomes white on the surface. Drying time depends on the size and thickness of the gel plug. Trypsin (or the enzyme being used is dissolved in digestion buffer and 5 mls added to the gel plug (depending on the amount of the protein in the gel to be analyzed (0.1 mg)). Additional digestion buffer is added until the gel plug is almost covered by buffer in the bottom of the tube, approximately 10 ml. The gel plug is then incubated at 37° C. for 6 hours or overnight, then incubated with 70-100 ml 60% acetonitrile/40% water for 2-6 hours to extract the peptides. The extraction may be repeated to increase recovery. The extract is then lyophilized and dissolved in 30% acetonitrile/2% TFA before analyzing by MALDI-MS.

FIGS. 6-48 provide the mass spectroscopic data obtain for the indicated protein of Tables 1 and 2.

Example 6

In Vivo Protein Expression During Allograft Rejection

To investigate protein changes in BB-DP islet allografts during rejection, 200 neonatal BB-DP rat islets were grafted to 30 day old WK rats (n=3). Grafts were retrieved 12 days after transplantation at which time point substantial mononuclear infiltration is expected. The grafts were processed and analyzed as described above.

Analysis of fluorographs from BB-DP islet allografts in WK rats. Twelve days after transplantation mononuclear cell infiltration was observed in the grafts (18), and computer analysis of fluorographs from the BB-DP islet allografts sampled at this time-point showed 1714 (1064 IEF and 650 NEPHGE) proteins present in 3 of 3 gels. The gels of the BB-DP islet allografts were compared to gels of neonatal BB-DP rat islets with regard to the 82 proteins that significantly changed level of expression in the BB-DP islets after IL-1 incubation in vitro. Sixty-six of the eighty-two proteins were re-identified. Thirty-three of the sixty-six re-identified proteins were found to change expression levels (28 decreased and 5 increased, $p<0.01$).

Example 7

Establishment of Non-Toxicity of Adenoviral-Mediated Gene Transfer in Islet Cells To determine the optimal conditions for adenoviral-mediated gene transfer to the islets of Langerhans in the absence of vector-induced toxicity, neonatal rat islets were transduced in groups of 25 in triplicate with an adenoviral vector β-galactosidase (AdβGal) at doses of multiplicity of infection (moi) 0, 10, 100, and 1000 pfu per islet. Efficiency of gene transfer was determined by gross inspection and estimated by the percentage of, 6-galactosidase positive cells after islet dispersion at 1, 4, 7, and 10 days post-transduction. Islet toxicity was assessed by measuring accumulated insulin levels at each time-point and by assessing insulin release in response to hyperglycemia at 3 and 10 days.

Results. Efficient dose-dependent gene transfer-to the islets was documented at 1, 4, 7, and 10 days post-transduction. At day 1, 8.3%, 34.1%, and 58.6% of cells in dispersed islets expressed transgene at moi 10, 100, and 1,000, respectively. Transgene expression was stable for the duration of the experiment. Insulin accumulation did not differ between transduced and non-transduced islets at each time-point; and accumulated insulin at 10 days expressed as nmol of insulin per islet was 14.3±1.5 at a moi of 0, 15.0±2.6 at a moi of 10, 22.0±7.8 at a moi of 100, and 15.3±1.5 at a moi of 1,000.

Similarly, the insulin secretory response to glucose, obtained by dividing the insulin response to high glucose incubation by the insulin response to low glucose incubation was similar in transduced and non-transduced islets at 3 days at all doses studied (mod 0; 12.7±4.1; moi 10, 14.9±7.9; moi 100, 15.7±0.7; and moi 1,000, 22.3±6.7). The ratios were similar in transduced and non-transduced cells at 10 days post-transduction.

Example 8

Expression of Galectin-3 in the Spontaneous Development of IDDM 200 neonatal BB-DP rat islets were transplanted under the kidney capsule of 30 day old BB-DP rats. Grafts retrieved day 7 after transplantation (prediabetic, n=6), at diabetes onset (n=6) or day 174 after transplantation (animals escaping diabetes, n=3) and IL-1β stimulated and non-stimulated neonatal BB-DP islets were labeled with [35S]-methionine and prepared for high-resolution two-dimensional gel electrophoresis.

Each sample was run on isoelectric focusing (IEF, pH 3.5-7) and non-equilibrium pH-gradient electrophoresis (NEPHGE, pH 6.5-10.5). Fluorographs of the gel were analyzed as described above. Changes in expression levels of proteins were considered significant at p values below 0.01 (Student's t-test).

Results. Neonatal BB-DP islets stimulated with IL-1β in vitro showed changes in 82 proteins. 97-98% of these proteins were identified in all grafts at all time points. Expression levels of graft proteins compared with non-stimulated normal BB-DP islets in vitro showed the following changes: Of the 82 proteins which exhibit increased expression when neonatal islet cells are treated with IL-1β in vitro, 42 were increased in the 7 day transplant islets, 31 were increased with diabetes onset, and 14 were increased in animals which did not develop diabetes. Of the proteins increased, 4 of them are only seen at onset of IDDM and not at the timepoints detailed. At day 7, five proteins which do not change with in vitro IL-1β exposure were observed to change, while 2 proteins were observed to change at the onset of diabetes, and 3 in the animals which did not develop diabetes. Of the proteins observed to change in vivo but not in vitro, one of these is identified as IDDM specific. Gal-3 expression was significantly down-regulated at day 7 and at onset of IDDM. In contrast, gal-3 expression was increased in in vitro IL-1β stimulated islets and in grafts from animals which did not develop diabetes.

Example 9

Cytokine Induction of IL-1 Converting Enzyme (ICE), Inductible Nitric Oxide Synthase (iNOS), and Apoptosis in Insulin-Producing Cells The expression of ICE, iNOS, and induction of apoptosis was investigated. Rat insulinoma and pluripotent cells lines RIN-SAH and MSL-G2 were cultured 20 hours with a mixture of cytokines (IL-1β, INFoα, and IFNγ), RNA isolated, and multiplex PCR analysis (27 cycles) with primers against ICE, iNOS, and SP-1 (a general transcription factor used as a housekeeping control gene for normalization) were formed. Results were normalized to SP-1 mRNA expression, and calculated following gel electrophoresis separation and PhosphorImager quantification.

Results. Neither ICE or iNOS expression were detected in control cells. A marked up-regulation to that of the level of the SP-1 gene product was seen in both ICE and iNOS after 20 hours of cytokine exposure. In RIN cells, ICE was produced at 98% and iNOS produced at 97% of SP-1. Whereas neither apoptosis or NOS production were detected in the control cells, cytokine-induced iNOS production was followed by a high increase in apoptosis-frequency and NO production. In RIN cells, accumulated nitrite was measured to be 19.7±0.7 µM after 3 days.

TABLE 1b

ISLET CELL DIABETES MEDIATING PROTEINS WHICH INCREASE UPON IL-1S STIMULATION IDENTIFIED BY 2DGE

| Gel Spot No. | Gene | Protein | Database Accession |
|---|---|---|---|
| IEF 010 | Unknown | MWt: 120,500; pI: 7.27 | |
| IEF 011 | EF2 | ELONGATION FACTOR 2 (EF-2) | P05197 |
| IEF 025 | VAT | VACUOLAR ATP SYNTHASE SUBUNIT B, BRAIN ISOFORM (EC 3.6.1.34) | P31408 |
| IEF 028 | MMLAMIN11 | LAMIN B1 (mouse) | D50080 |
| IEF 083 | PYC | PYRUVATE CARBOXYLASE PRECURSOR (EC 6.4.1.1) | P52873 |
| IEF 085 | PYC | PYRUVATE CARBOXYLASE PRECURSOR (EC 6.4.1.1) | P52873 |
| IEF 115 | Unknown | MWt: 175,200; pI: 5.23 | |
| IEF 145 | Unknown | MWt: 133,100; pI: 6.29 | |
| IEF 173 | MVP | MAJOR VAULT PROTEIN | Q62667 |
| IEF 186 | HS74 | HEAT SHOCK 70 KD PROTEIN AGP-2 (mouse) | Q61316 |
| IEF 187 | HS74 | HEAT SHOCK 70 KD PROTEIN AGP-2 (mouse) | Q61316 |
| IEF 189 | Unknown | MWt: 135,100; pI: 4.96 | |
| IEF 194 | UBP1 | UBIQUITIN CARBOXYL-TERMINAL HYDROLASE T (EC 3.1.2.15) | P45974 |
| IEF 201 | CALX | CALNEXIN PRECURSOR | P35565 |
| IEF 210 | Unknown | MWt: 114,500; pI: 6.40 | |
| IEF 217 | Unknown | MWt: 91,300; pI: 6.12 | |
| IEF 225 | Unknown | MWt: 83,300; pI: 5.89 | |
| IEF 265 | TERA | TRANSITIONAL ENDOPLASMIC RETICULUM ATPASE (TER ATPASE) | P46462 |
| IEF 267 | HS9B | HEAT SHOCK PROTEIN HSP 90-BETA (HSP 84) | P34058 |
| IEF 276 | Unknown | MWt: 107,500; pI: 4.34 | |
| IEF 279 | Unknown | MWt: 121,400; pI: 4.20 | |
| IEF 285 | Unknown | MWt: 78,300; pI: 6.66 | |
| IEF 289 | Unknown | MWt: 73,900; pI: 6.44 | |
| IEF 306 | Unknown | MWt: 75,700; pI: 6.20 | |
| IEF 310 | SYG | GLYCYL-TENA SYNTHETASE (EC 6.1.1.14) | P41250 |
| IEF 329 | GR78 | 78 KD GLUCOSE REGULATED PROT. PREC. (GRP 78) | P06761 |
| IEF 329 | NCPR | NADPH-CYTOCHROME P450 REDUCTASE (EC 1.6.2.4) | P00388 |
| IEF 330 | GR75 | MITOCHONDRIAL STRESS-70 PROTEIN PRECURSOR (MORTALIN) | P48721 |
| IEF 342 | Unknown | MWt: 83,300; pI: 4.81 | |
| IEF 347 | GR78 | 78 KD GLUCOSE REGULATED PROT. PREC. (GRP 78) | P06761 |
| IEF 354 | Unknown | MWt: 70,400; pI: 4.30 | |
| IEF 382 | Unknown | MWt: 63,900; pI: 6.35 | |
| IEF 387 | TO64 | TURNED ON AFTER DIVISION, 64 KD PROT. (TOAD-64) | P47942 |
| IEF 387 | TCPG | T-COMPLEX PROTEIN 1, GAMMA SUBUNIT (Mouse/Human) | P80318 |
| IEF 387 | COPD | COATOMER DELTA SUBUNIT (DELTA-COAT PROTEIN) (Bovine/Human) | P53619 |

TABLE 1b-continued

ISLET CELL DIABETES MEDIATING PROTEINS WHICH INCREASE UPON IL-1S STIMULATION IDENTIFIED BY 2DGE

| Gel Spot No. | Gene | Protein | Database Accession |
|---|---|---|---|
| IEF 425 | HS7C | HEAT SHOCK COGNATE 71 kD PROTEIN | P08109 |
| IEF 471 | Unknown | MWt: 60,700; pI: 6.08 | |
| IEF 480 | Unknown | MWt: 62,000; pI: 5.91 | |
| IEF 483 | ER60 | PROTEIN DISULFIDE ISOMERASE ER-60 PRECURSOR (EC 5.3.4.1) (ERP60) | P11598 |
| IEF 505 | Unknown | MWt: 61,500; pI: 5.41 | |
| IEF 506 | TCPE | T-COMPLEX PROTEIN 1, EPSILON SUBUNIT (TCP-1-EPSILON) (Mouse) | P80316 |
| IEF 507 | P60 | MITOCHONDRIAL MATRIX PROTEIN P1 PRECURSOR (HSP-60) | P19227 |
| IEF 561 | ENOA | ALPHA ENOLASE (EC 4.2.1.11) | P04764 |
| IEF 563 | Unknown | MWt: 18,000; pI: 6.20 | |
| IEF 655 | LAMA | LAMIN A | S47890 |
| IEF 759 | HSU36764 | TGF-beta RECEPTOR INTERACTING PROTEIN 1 (HUMAN) | U36764 |
| IEF 1081 | Unknown | MWt: 53,800; pI: 5.43 | |
| IEF 1196 | Unknown | MWt: 243,100; pI: 5.41; Mass spec FIGS. 20-23 | |
| IEF 1342 | Unknown | MWt: 53,400; pI: 4.64 | |
| IEF 1356 | Unknown | MWt: 147,900; pI: 5.40 | |
| NEPHGE 017 | G3P | GLYCERALDEHYDE 3-PHOSPHATE DEHYDROGENASE (EC 1.2.1.12) (GAPDH) | P04797 |
| NEPHGE 156 | PTB | POLYPYRIXIDINE TRACT-BINDING PROTEIN (PTB) (HNRNP I) | Q00438 |
| NEPHGE 169 | F261 | 6-PHOSPHOFRUCTO-2-KINASE (EC 2.7.1.105) | P07953 |
| NEPHGE 203 | PGK2 | PHOSPHOGLYCERATE KINASE (EC 2.7.2.3), | P16617 |
| NEPHGE 269 | ANX2 | ANNEXIN II (LIPOCORTIN II) (CALPACTIN I HEAVY CHAIN) | Q07936 |
| NEPHGE 269 | G3P | GLYCERALDEHYDE 3-PHOSPHATE DEHYDROGENASE (EC 1.2.1.12) (GAPDH) | P04797 |
| NEPHGE 298 | LEG3 | GALECTIN-3 (GALACTOSE-SPECIFIC LECTIN 3) | P08699 |
| NEPHGE 298 | Unknown | MWt: 36,400; pI: 8.32 | |
| NEPHGE 668 | ALFA | FRUCTOSE-BISPHOSPHATE ALDOLASE (EC 4.1.2.13) A (MUSCLE) | P05065 |
| NEPHGE 670 | Unknown | MWt: 148,700; pI: 8.10 | |
| NEPHGE 672 | Unknown | MWt: 132,500; pI: 8.52 | |
| NEPHGE 673 | Unknown | MWt: 132,500; pI: 8.46 | |
| NEPHGE 674 | Unknown | MWt: 132,500; pI: 8.42 | |

TABLE 2

ISLET CELL DIABETES MEDIATING PROTEINS WHICH DECREASE UPON IL-18 STIMULATION IDENTIFIED BY 2DGE

| Gel Spot No. | Gene | Protein | Database Accession |
|---|---|---|---|
| IEF 015 | Unknown | MWt: 75,400; pI: 6.01 | |
| IEF 339 | GR78 | 78 KD GLUCOSE REGULATED PROTEIN PRECURSOR (GRP 78) | P06761 |
| IEF 340 | GR75 | MITOCHONDRIAL STRESS-70 PROTEIN PRECURSOR (GRP 75) | P48721 |
| IEF 344 | GR78 | 78 KD GLUCOSE REGULATED PROTEIN PRECURSOR (GRP 78) | P20029 |
| IEF 358 | Unknown | MWt: 77,000; pI: 4.11 | |
| IEF 436 | NEC2 | NEUROENDOCRINE CONVERTASE 2 PRECURSOR (EC 3.4.21.94) (NEC 2) | P28841 |
| IEF 441 | NEC2 | NEUROENDOCRINE CONVERTASE 2 PRECURSOR (EC 3.4.21.94) (NEC 2) | P28841 |
| IEF 442 | NEC2 | NEUROENDOCRINE CONVERTASE 2 PRECURSOR (EC 3.4.21.94) (NEC 2) | P28841 |
| IEF 484 | ER60 | PROTEIN DISULFIDE ISOMERASE ER60 PRECURSOR (EC 5.3.4.1) (ERP60) | P11598 |
| IEF 510 | Unknown | MWt: 54,400, pI: 5.27 | |
| IEF 614 | ERP5 | PROBABLE PROTEIN DISULFIDE ISOMERASE P5 PRECURSOR (EC 5.3.4.1) | Q63081 |
| IEF 614 | ATPB | ATP SYNTHASE BETA CHAIN, MITOCHONDRIAL PRECURSOR (EC 3.6.1.34) | P10719 |
| IEF 665 | MTA1 | METASTASIS-ASSOCIATED PROTEIN MTA1 | Q62599 |
| IEF 719 | Unknown | MWt: 39,600; pI: 6.55 | |
| IEF 825 | Unknown | MWt: 35,000; pI: 5.10 | |
| IEF 831 | Unknown | MWt: 34,600; pI: 4.76; Mass spec FIG. 41 | |
| IEF 882 | Unknown | MWt: 30,800; pI: 4.94 | |
| IEF 887 | Unknown | MWt: 30,800; pI: 4.76 | |
| IEF 895 | Unknown | MWt: 28,900; pI: 4.29 | |
| IEF 908 | ER31 | ENDOPLASMIC RETICULUM PROTEIN ERP31 PRECURSOR (ERP29) | P52555 |
| IEF 908 | PMGB | PHOSPHOGLYCERATE MUTASE, BRAIN FORM (EC 5.4.2.1) | P25113 |
| IEF 939 | Unknown | MWt: 25,900; pI: 5.09; Mass spec FIGS. 16 | |
| IEF 941 | PBP | PHOSPHATIDYLETHANOLAMINE-BINDING PROTEIN (P23K) | P31044 |
| IEF 949 | RNU53882 | 14-3-3 PROTEIN EPSILON ISOFORM | U53882 |
| IEF 949 | Unknown | MWt: 26,800; pI: 4.49 Mass spec FIGS. 42-43 | |
| IEF 950 | Unknown | MWt: 25,800; pI: 4.53; Mass spec FIGS. 19 | |
| NEPHGE 001 | KPY2 | PYRUVATE KINASE, M2 ISOZYME (EC 2.7.1.40) | P11981 |
| NEPHGE 007 | Unknown | MWt: 65,500; pI 7.28, Mass spec FIG. 24 | |
| NEPHGE 009 | Unknown | MWt: 115,700, pI 8.33; Mass spec FIG. 25 | |
| NEPHGE 018 | DHE3 | GLUTAMATE DEHYDROGENASE PRECURSOR (EC 1.4.1.3.) (GDH) | P10860 |
| NEPHGE 102 | TCPZ | T-COMPLEX PROTEIN 1, ZETA SUBUNIT | P80317 |
| NEPHGE 102 | RNPKKPS | PYRUVATE KINASE M | M24361 |
| NEPHGE 123 | KPY2 | PYRUVATE KINASE, M2 ISOZYME (EC 2.7.1.40). | P11981 |

TABLE 2-continued

ISLET CELL DIABETES MEDIATING PROTEINS WHICH DECREASE
UPON IL-18 STIMULATION IDENTIFIED BY 2DGE

Figure 44:
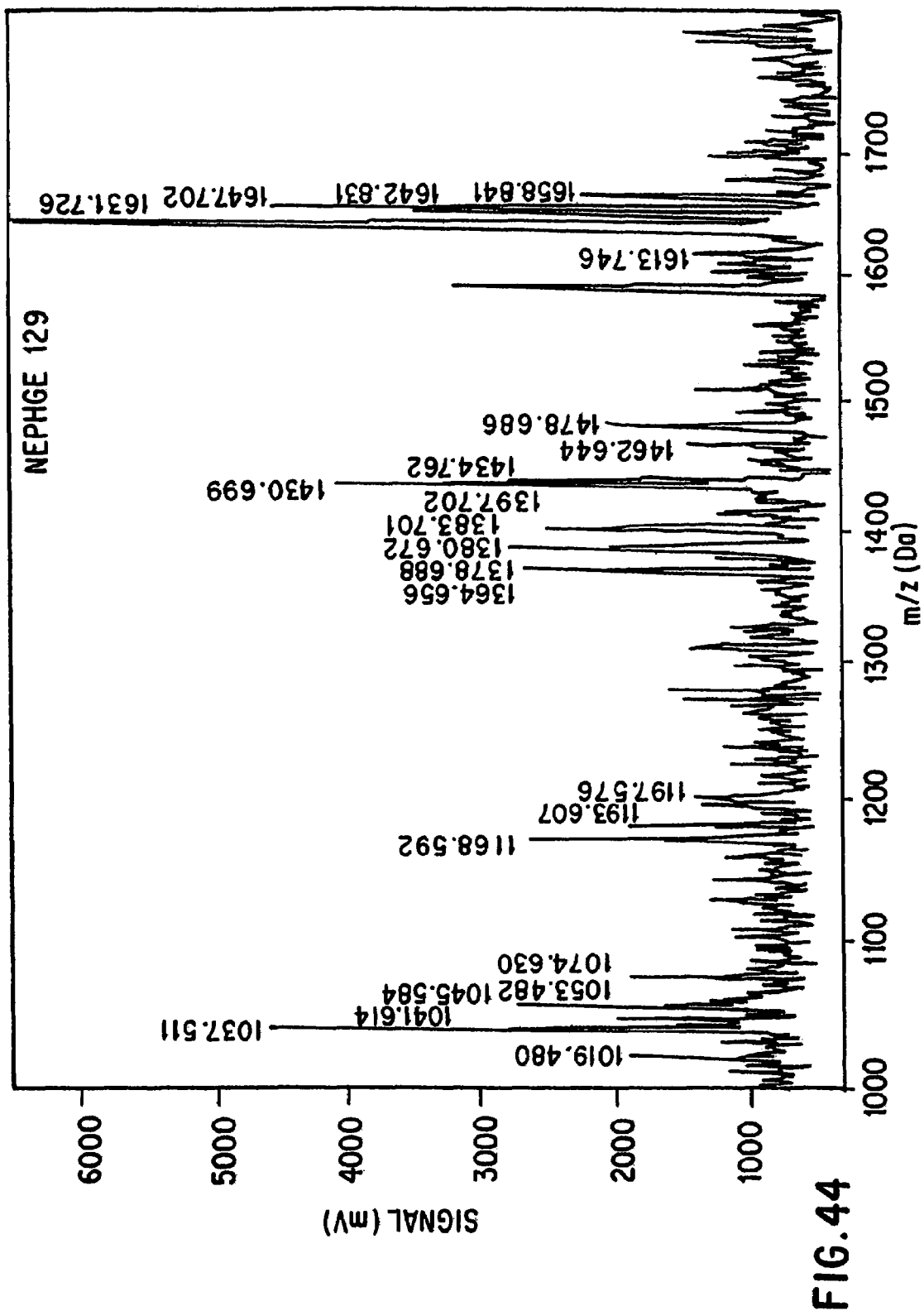
FIGS. 44-46 are the mass spectroscopy spectrum for a novel diabetes-mediating protein, termed "NEPHGE Spot No. 129," having a molecular weight of 57,600 daltons and a pI of 7.72, determined as indicated.
Figure 45:
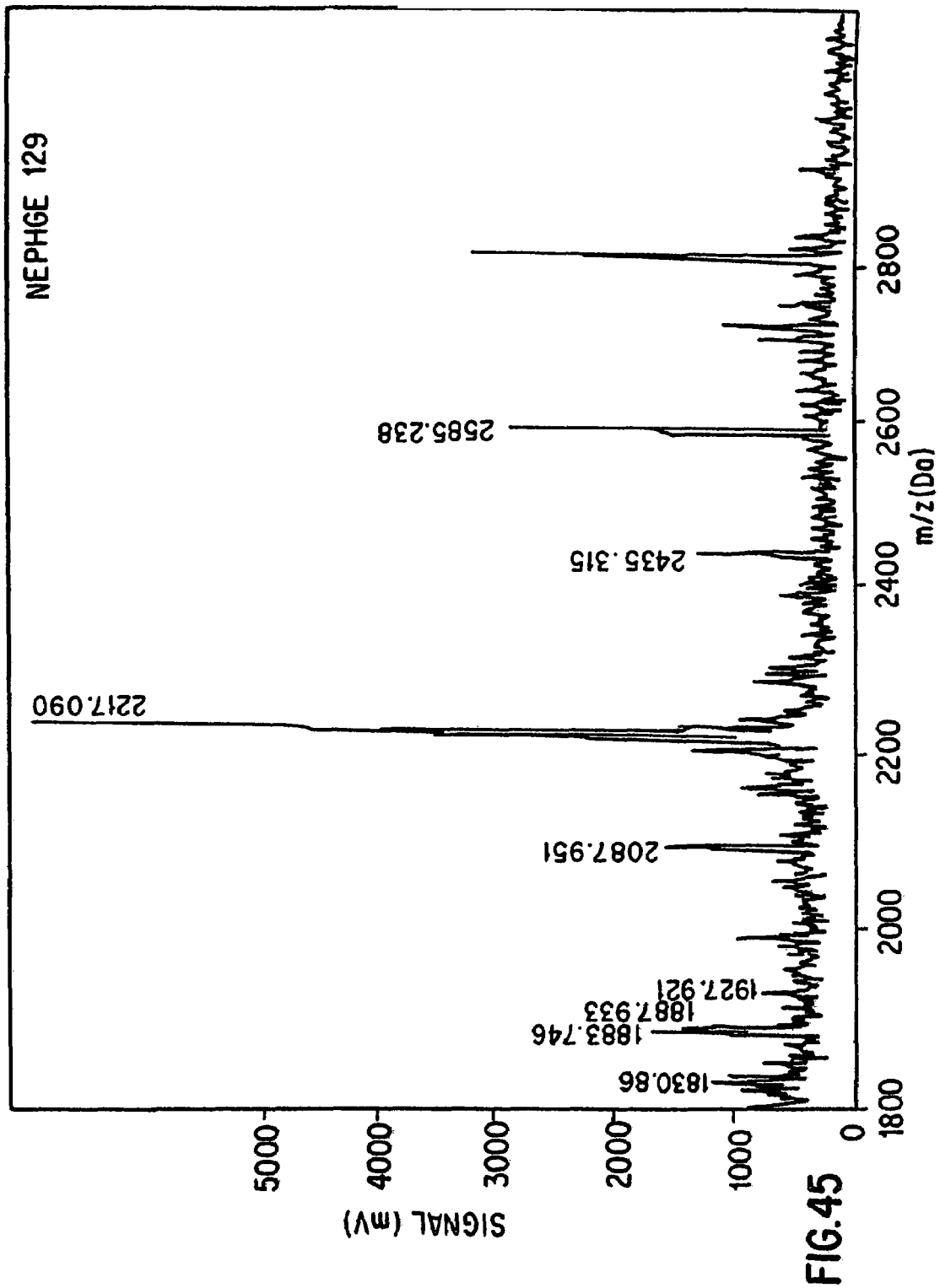
Figure 46:
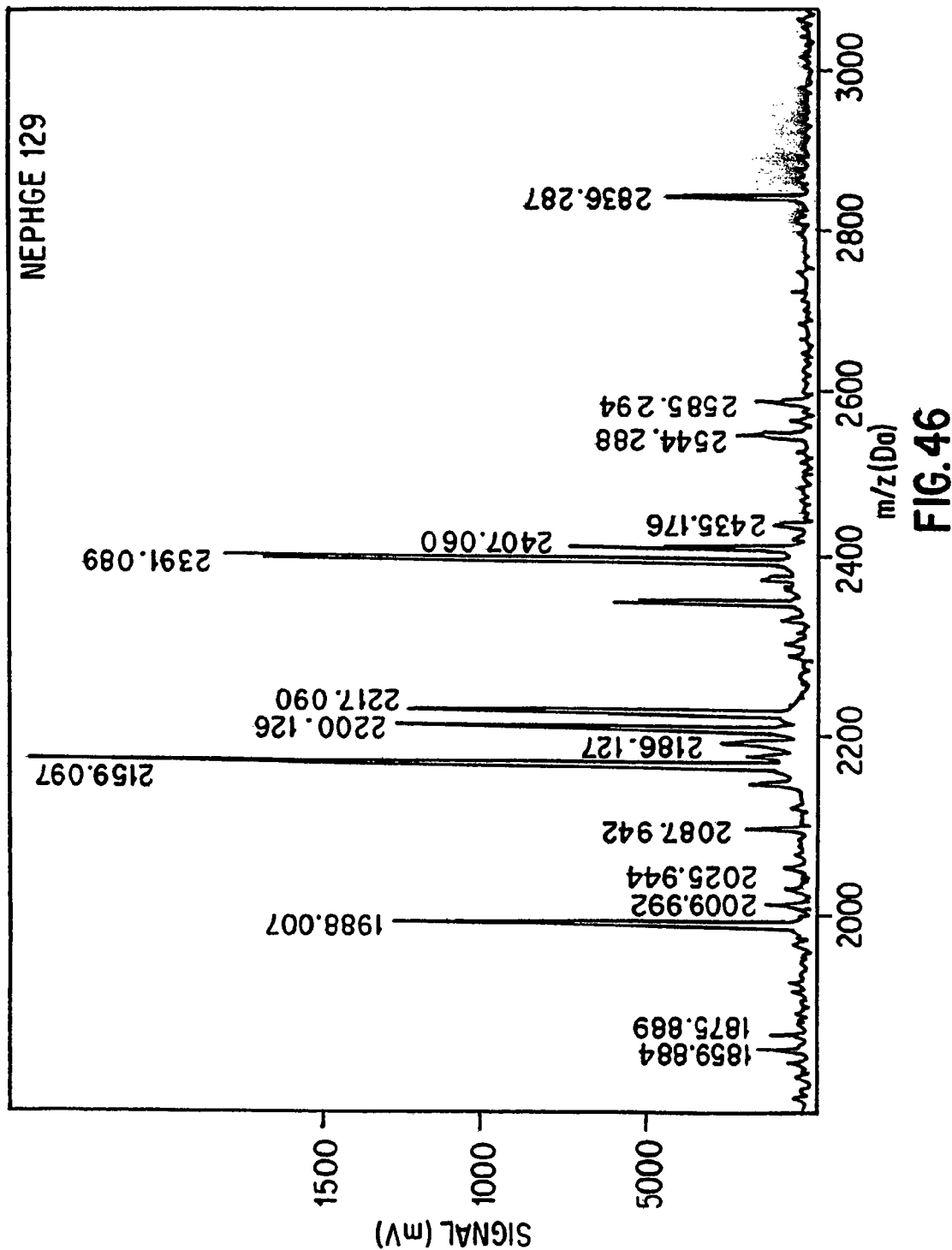
Figure 47:
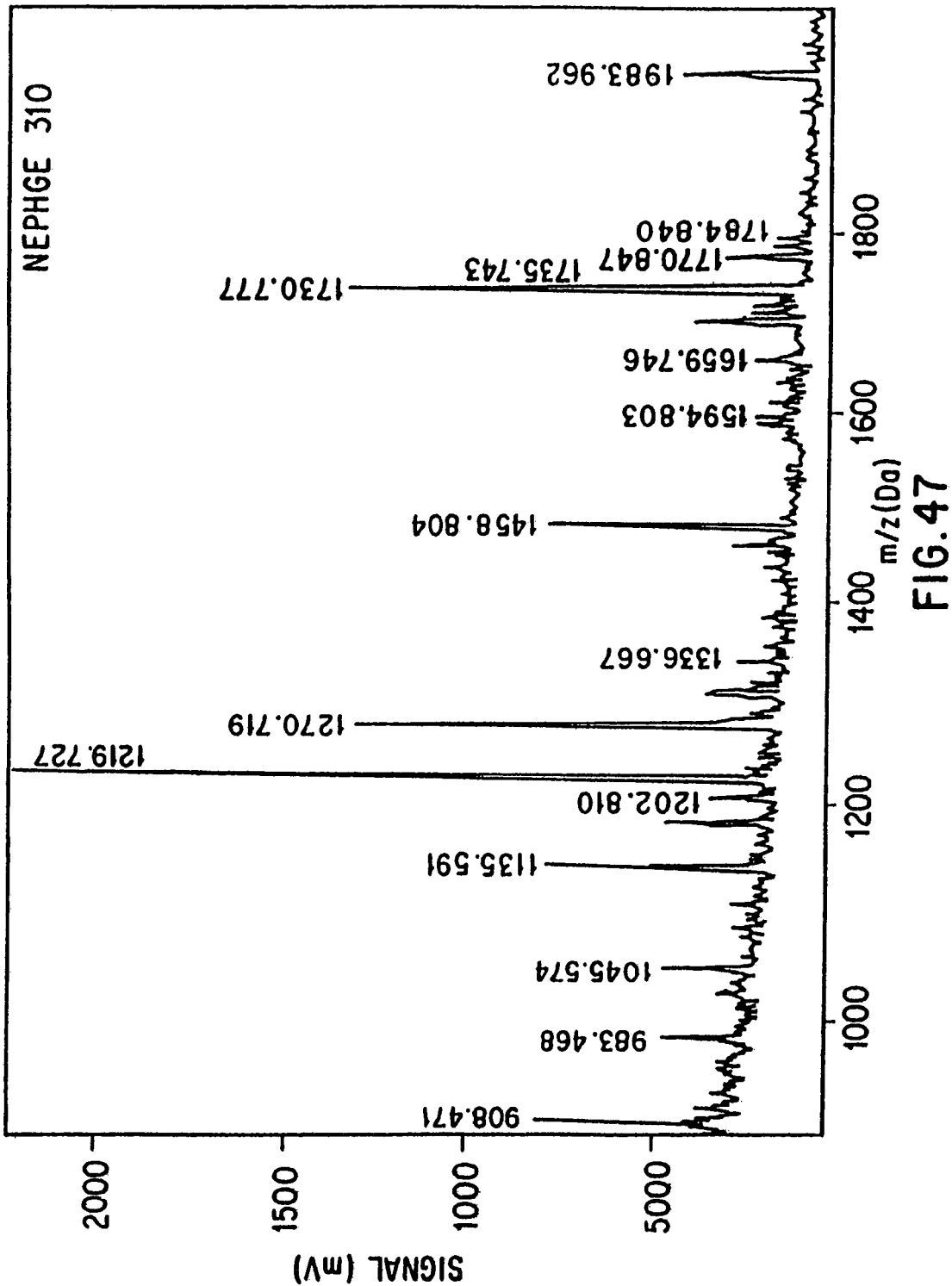
FIG. 47 is a mass spectroscopy spectrum for a novel diabetes-mediating protein, termed "NEPHGE Spot No. 310," having a molecular weight of 35,800 daltons and a pI of 7.57, determined as indicated.
Figure 48:
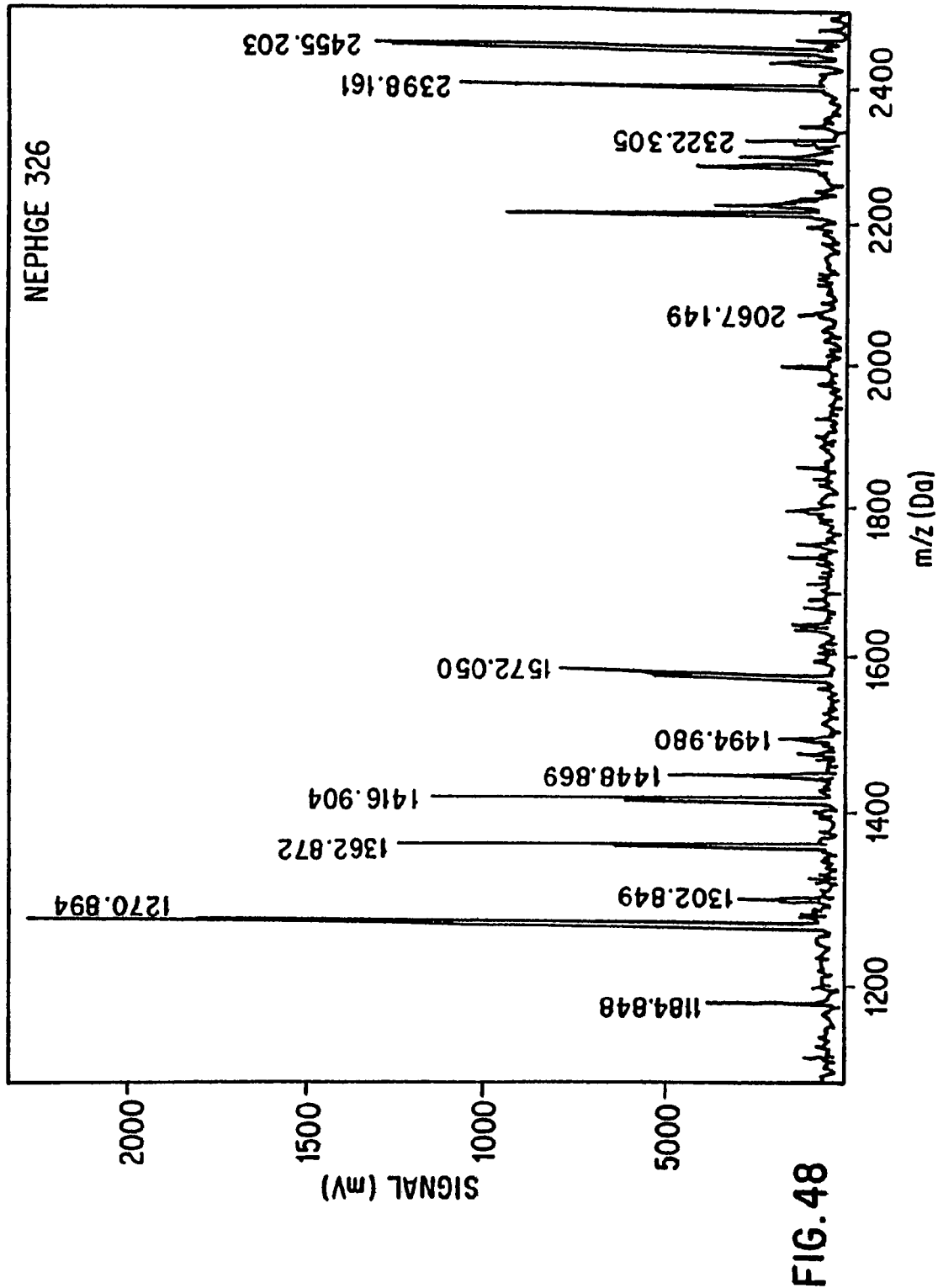
FIG. 48 is a mass spectroscopy spectrum for a novel diabetes-mediating protein, termed "NEPHGE Spot No. 326," having a molecular weight of 34,500 daltons and a pI of 8.62, determined as indicated.

| Gel Spot No. | Gene | Protein | Database Accession |
|---|---|---|---|
| NEPHGE 129 | KPY2 | PYRUVATE KINASE, M2 ISOZYME | P11981 |
| NEPHGE 129 | Unknown | MWt: 57,600 pI: 7.72 Mass spec FIGS. 44-46 | |
| NEPHGE 130 | MMSA | METHYLMALONATE-SEMIALDEHYDE DEHYDROGENASE PRECURSOR | Q02253 |
| NEPHGE 130 | RNPKMPS | PYRUVATE KINASE M INTRONLESS PROCESSED PSEUDOGENE | M24361 |
| NEPHGE 171 | ATPA | ATP SYNTHASE ALPHA CHAIN, MITOCHONDRIAL PRECURSOR (EC 3.6.1.34) | P15999 |
| NEPHGE 174 | DHE3 | GLUTAMATE DEHYDROGENASE PRECURSOR (EC 1.4.1.3) (GDH) | P10860 |
| NEPHGE 176 | ATPA | ATP SYNTHASE ALPHA CHAIN, MITOCHONDRAIL PRECURSOR (EC 3.6.1.34) | P15999 |
| NEPHGE 181 | Unknown | MWt: 49,400; pI 7.40; Mass spec FIGS. 32-33 | |
| NEPHGE 182 | DHE3 | GLUTAMATE DEHYDROGENASE PRECURSOR (EC 1.4.1.3.) (GDH) | P10860 |
| NEPHGE 211 | Unknown | MWt: 47, 900; pI 7.28; Mass spec FIG. 36 | |
| NEPHGE 227 | THIL | ACETYL-COA ACETYLTRANSFERASE PRECURSOR, MITOCHONDRIAL (EC 2.3.1.9) | P17764 |
| NEPHGE 231 | BKCRU | CREATINE KINASE, UBIQUITOUS MITOCHONDRIAL PRECURSOR (EC 2.7.3.2) | P25809 |
| NEPHGE 231 | BTHIL | ACETYL-COA ACETYLTRANSFERASE PRECURSOR, MITOCHONDRIAL (EC 2.3.1.9) | P17764 |
| NEPHGE 236 | Unknown | MWt: 43,200; pI 7.90; Mass spec FIG. 38 | |
| NEPHGE 253 | Unknown | MWt: 39,100; pI 9.05; Mass spec FIGS. 39-40 | |
| NEPHGE 296 | NC5R | NADH-CYTOCHROME B5 REDUCTASE (EC 1.6.2.2) | P20070 |
| NEPHGE 306 | KAD2 | ADENYLATE KINASE ISOENZYME 2, MITOCHONDRIAL (EC 2.7.4.3) | P29410 |
| NEPHGE 310 | Unknown | MWt: 35,800; pI: 7.57; Mass spec FIG. 47 | |
| NEPHGE 326 | Unknown | MWt: 34,500; pI: 8.62; Mass spec FIG. 48 | |
| NEPHGE 328 | Unknown | MWt: 30,900; pI: 8.48 | |
| NEPHGE 334 | TPIS | TRIOSEPHOSPHATE ISOMERASE (EC 5.3.1.1) (TIM) | P48500 |

Example 10

Interleukin-1DF Induced Changes in the Protein Expression of rat Islets: A Computerized Database Summary Two-dimensional (2-D) gel electrophoresis of pancreatic islet proteins can be an important tool facilitating studies of the molecular pathogenesis of insulin-dependent diabetes mellitus. Insulin-dependent diabetes mellitus is caused by an autoimmune destruction of the β-cells in the islets of Langerhans. The cytokine interleukin 1β inhibits insulin release and is selectively cytotoxic to β-cells in isolated pancreatic rat islets. The antigen(s) triggering the immune response as well as the intracellular mechanisms of action of interleukin 1β-mediated β-cell cytotoxicity are unknown. However, previous studies have found an association with alterations in protein synthesis. Thus, 2-D gel electrophoresis of islet proteins can lead to 1) the identification of primary antigen(s) initiating the immune destruction of the β-cells 2) the determination of qualitative and quantitative changes in specific islet proteins induced by cytokines and 3) the determination of the effects of agents modulating cytokine action. Therefore, the aim of this study was to create databases of all reproducibly detectable protein spots on 10% and 15% acrylamide 2-D gels of neonatal rat islets (10% & 15% DB), labelled under standardized culture conditions. 1792 spots were present in 5 of 5 gels in the 15% DB, whereas 1373 spots were present in 5 of 5 gels in the 10% DB, yielding a qualitative reproducibility between 75.2% and 91.7%. In both DBs, the average coefficient of variation of the percentage of integrated optical density (CV % of % IOD) for spots present in all gel was between 42.4% and 45.7%. When the same sample was analyzed in consecutive sets of gels on different days (interassay analysis), the average CV % of % IOD was 35.5%-36.1%. When the same sample was analyzed repeatedly in one set of gels (intraassay analysis), the average CV % of % IOD was 30.2% in the IEF gels, while the average CV % of % IOD was unchanged (45.7%) in the NEPHGE gels. Applying the 10% DB to distinguish proteins altered in expression by IL-1β, 105 currently unidentified protein spots were found to be up-/down-regulated or synthesized de novo by IL-1β. In conclusion, we present the first 10% and 15% acrylamide 2-D gel protein databases of neonatal rat islets of Langerhans and demonstrate its usage to identify proteins altered in expression by IL-1β.

Introduction

The cytokine interleukin 1β inhibits insulin release and is selectively cytotoxic to β-cells in isolated pancreatic rat islets (Mandrup-Poulsen, T, *Diabetologia*, in press (1996)). Active protein synthesis is a crucial part of β-cell destruction, defense and repair after insults such as cytokines. The free radical nitric oxide (NO) has been demonstrated to be an important mediator of the deleterious effects of cytokines on islet α-cells (Southern, et al., *FEBS. Lett.* 276:42-44 (1990); Welsh, et al., *Endocrinol.* 129:3167-3173 (1991); Corbett, et al., *J. Biol. Chem.* 266:21351-21354 (1991)). Thus, analogues of L-arginine, the substrate for NO production, prevent the deleterious effects of interleukin 1β (IL-1β) (Southern, et al., *FEBS. Lett.* 276:42-44 (1990); Welsh, et al., *Endocrinol.* 129:3167-3173 (1991); Corbett, et al., *J. Biol. Chem.* 266:21351-21354 (1991)) and mRNA for the cytokine-inducible isoform of NO synthase (iNOS) is induced by IL-1β in β-, but not α-cells (Corbett, et al., *J. Clin. Invest.* 90:2384-2391 (1992)). We have recently cloned iNOS from neonatal rat islets and have demonstrated the expression of the recombinant NOS as a series of spots on two-dimensional (2-D) gels, most likely as phosphorylated isoforms, with the expected molecular mass of 131 kDa and pI values in the range of 6.8 to 7.0 (Karlsen, et al., *Diabetes* 44:753-758 (1995)).

Further, inhibitors of protein synthesis block the inhibitory effect of IL-1β on islet function (Hughes, et al., *J. Clin. Invest.* 86:856-863 (1990)), indicating that de novo protein synthesis is necessary for the deleterious effect of IL-1β. IL-1β also induces the synthesis of the heat shock proteins (HSP) HSP32 (heme oxygenase) and HSP70 (Helqvist, et al., *Acta Endo-* crinol. (*Copenh.*) 121:136-140 (1989); Helqvist, et al., *Diabetologia* 34:150-156 (1991); Welsh, et al., *Autoimmunity* 9:33-40 (1991)), known to play a role in protection against cellular stress and in cell repair (Kaufmann, *Immunol. Today* 11:129-136 (1990)). Further, IL-1β inhibits the synthesis of a number of unknown proteins with molecular weights of 45, 50 (Hughes, et al., *J. Clin. Invest.* 86:856-863 (1990)), 75, 85, 95 and 120 kDa (Welsh, et al., *Autoimmunity* 9:33-40(1991)) in islets. Using 2-D gel electrophoresis, we recently demonstrated that IL-1β up- and downregulated 29 and 3 proteins, respectively, in neonatal rat islets.

Endocrine islet cells can play an important role in β-cell destruction and, possibly, survival. Dispersion and sorting of islet cells is a potentially harmful procedure that could influence the protein synthesis pattern. The disadvantage of the chosen islet cell material is that any change in protein expression in one cell type will appear smaller because it is diluted by synthesis from other cells.

Thus, the aims of this study were to determine the spot detection reproducibility and to calculate the coefficient of variation of the percentage of integrated optical density (CV % of % IOD) for all ($^{35}$S)-methionine-labelled islet protein database spots. Additionally, we wanted to investigate the contribution of the intra- and interassay variation of the gel preparation to the total CV % of % IOD of the spots. Finally, we wanted to define the number of IL-1β-induced changes in the islet protein pattern by computer analysis.

Materials and Methods

Reagents. DMEM, RPMI 1640 and Hanks' balanced salt solution (HBSS) were purchased from Gibco, Paisley, Scotland. RPMI 1640 was supplemented with 20 mM HEPES buffer, 100,000 IU/l penicillin and 100 mg/L streptomycin. Authentic recombinant human IL-1β was provided by Novo Nordisk Ltd. (Bagsvaerd, Denmark). The specific activity was 400 U/ng (Moelvig, et al., *Scand. J. Immunol.* 31:225-235 (1990). The following other reagents were used: 2-mercaptoethanol, bovine serum albumin (BSA), Tris HCI, Tris base, glycine, (Sigma, St. Louis, USA); trichloracetic acid (TCA), phosphoric acid, NaOH, glycerol, n-butanol, bromophenol blue (Merck, Darmstadt, Germany); ($^{35}$S)-methionine (SJ 204, specific activity: >1.000 Ci/mmol, containing 0.1% 2-mercaptoethanol), Amplify® (Amersham International, Amersham, UK); filters (HAWP 0.25 µm pore size) (Millipore, Boston, USA); RNA'se A, DNA'se I (Worthington, Freehold, N.J., USA); urea (ultra pure) (Schwarz/Mann, Cambridge, Mass., USA); acrylamide, bisacrylamide, TEMED, ammonium persulphate (BioRad, Richmond, Calif., USA); ampholytes: pH 5-7, pH 3.5-10, pH 7-9, pH 8-9.5 (Pharmacia, Uppsala, Sweden); Nonidet P-40 (BDH, Poole, UK); ampholytes: pH 5-7 and sodium dodecyl sulphate (Serva, Heidelberg, Germany); agarose (Litex, Copenhagen, Denmark); ethanol (absolute 96%) (Danish Distillers, Aalborg, Denmark); methanol (Prolabo, Brione Le Blanc, France); acetic acid (technical quality, 99% glacial) (Bie & Berntsen, Århus, Denmark) and X-ray film (Curix RP-2) (AGFA).

Islet isolation and culture. For the database and assay variation experiments, 12 different islet isolations were performed, 10 for the databases, 1 for intraassay and 1 for interassay analysis. For the studies involving IL-1β, 3 additional islet isolations were performed.

Islets from pancreata of 4 day old inbred Wistar Furth rats (Mollegard, Lille Skensved, Denmark) were isolated after collagenase digestion (Brunstedt, In: Larner, J., Polh, S. L. (Eds.), *Methods In Diabetes Research, Vol. 1* (*Laboratory methods, Part C*). Wiley & Sons, New York, pp. 254-288 (1984)). After a preculture period of 4 days in RPMI 1640+ 10% fetal calf serum, 150 islets were incubated for 24 h in 300 µl RPMI 1640+0.5% normal human serum (NHS). In a separate series of experiments, 150 islets were incubated for 24 h in 300 µl RPMI 1640+0.5% NHS with or without the addition of 150 pg/ml IL-1β.

Islet labelling. After 24 h in culture, the 150 islets were harvested, washed twice in HBSS and labelled for 4 h in 200 µl methionine-free Dulbecco's modified Eagle's's medium (DMEM) with 10% NHS dialysed for amino acids, and 200 µCi ($^{35}$S)-methionine. To eliminate 2-mercaptoethanol ($^{35}$S)-methionine was freeze-dried for at least 4 h before labelling. After labelling, islets were washed thrice in HBSS, pelleted and frozen at −80° C.

Sample preparation. The frozen islets were resuspended in 100 µl DNAse I/RNAse A solution and lysed by freeze-thawing twice. After the second thawing they were left on ice for 30 min for the digestion of nucleic acids. The lysed sample was then freeze dried overnight. The samples wee dissolved by shaking in 120 µl lysis buffer (8.5 M urea, 2% Nonidet P-40, 5% 2-mercaptoethanol and 2% ampholytes pH range 7-9) for a minimum of 4 h.

Determination of ($^{35}$S)-methionine incorporation. The amount of ($^{35}$S)-methionine incorporation was quantitated in duplicate by adding 10 µg BSA (0.2 µg/ml H$_2$0) as a carrier to 5 µl of a 1:10 dilution of each sample, followed by 0.5 ml of 10% TCA. This was left to precipitate for 30 min at 40° C. before being filtered through 0.25 µm filters. The HAWP filters were dried and placed into scintillation liquid for counting.

2-D gel electrophoresis. The procedure was essentially as described by O'Farrell et al., *Cell* 12:1133-1142 (1977) and Fey, S. J. et al., *The protein variation in basal cells and certain basal cell related benign and malignant diseases*, Faculty of Natural Science, University of Aarhus, Denmark (1984). Briefly, first dimension gels contained 4% acrylamide, 0.25% bisacrylamide and ampholytes (the actual ratio depending upon the batch) and were 175 mm long and 1.55 mm in diameter. Equal numbers of counts (10$^6$ cpm) of each sample were applied to the gels. In case of lower amounts of radioactivity it was necessary to regulate the exposure time of the gel so that comparable total optical densities were obtained. The samples were analyzed on both isoelectric focusing (IEF; pH 3.5-7) and non equilibrium pH-gradient electrophoresis (NEPHGE; pH 6.5-10.5) gels. IEF gels were prefocused for approximately 4 h at 140 µA/gel (limiting current), the sample was then applied and focused for 18 h at 1200 V (limiting voltage). NEPHGE gels were focused for approximately 6.5 h using 140 µA/gel and 1200 V as the limiting parameters.

Second dimension gels, 1 mm thick, 200 mm long and 185 mm wide contained either 15% acrylamide and 0.075% bisacrylamide or 10% acrylamide and 0.05% bisacrylamide and were run overnight. After electrophoresis, the gels were fixed in 45% methanol and 7.5% acetic acid for 45 min and treated for fluorography with Amplify® for 45 min before being dried. The gels were placed in contact with X-ray films and exposed at −70° C. for 1 to 40 days. Each gel was exposed for at least 3 time periods to compensate for the lack of dynamic range of X-ray films.

Determination of MW and pI. Molecular weights of the proteins were determined by comparison with standard gels (Fey, S. J. et al., *The protein variation in basal cells and certain basal cell related benign and malignant diseases*, Faculty of Natural Science, University of Aarhus, Denmark (1984)). pI for the individual proteins on the gels was determined by the use of pI calibration kits. Landmark proteins were identified on gels by one or several of the following techniques: immunoblotting, immunoprecipitation, microsequencing or peptide mapping.

Experimental design. The study comprised three different series of analyses: database, intra- and interassay analysis. For each analysis, IEF and NEPHGE gels were run using 10% and 15% acrylamide in the second dimension. This gave us four subgroups: 10% IEF; 15% IEF; 10% NEPHGE; 15% NEPHGE. On 10% acrylamide gels, the approximate MW range of detection were between 20 and 250 kDa, while the approximate range of detection was between 6 and 125 kDa on 15% acrylamide gels. Consequently, proteins with a MW between 20 and 125 kDa were included in both databases, whereas proteins with lower and higher MW were particular to 15% and 10% DBs, respectively. Comparison of 10% and 15% DBs revealed a lower number of detectable spots in both 10% IEF and NEPHGE subgroups (see Results). Consequently, intra- and interassay analysis (see below) were only performed on 15% IEF and NEPHGE gels.

The databases were based on 10 different isolates analyzed in one set of gels. After 2-D gel electrophoresis, 5 gels with the best technical quality and with comparable optical densities were chosen for computer analysis. Before computer analysis, one gel in each subgroup was arbitrarily selected to be the "master gel" used for comparison with the other 4 database gels, the 5 intraassay gels and the 5 interassay gels. The database "master gel" was used as a master for intra- and interassay analysis to ensure that a given spot had the same match number in the three series of analyses. Data from the "master gel" are only included in the database analysis. The "master gel" was from the same isolate in all 4 subgroups, whereas the identity of the isolates producing the 4 other database gels varied slightly from subgroup to subgroup (Table 3).

For intraassay analysis, 10 gels of the same sample were analyzed in one set of gels. After 2-D gel electrophoresis, 5 gels with the best technical quality and with comparable optical densities were chosen for computer analysis (Table 3).

For interassay analysis, the same sample was analyzed in 10 consecutive sets of gels on different days. After 2-D gel electrophoresis, 5 gels with the best technical quality and with comparable optical densities were chosen for computer analysis (Table 3).

For identification of proteins altered in expression by IL-1$\beta$, 10% IEF and NEPHGE gels of IL-1$\beta$ exposed islets, previously analyzed visually (Andersen, et al., *Diabetes* 44:400-407 (1995)), were matched to the 10% IEF and NEPHGE DBs.

Computer analysis of fluorographs. Computer analysis was performed using the BioImage® program (version 4.6 M) on a Sunsparc workstation. First, the fluorographs were scanned and spots were identified and quantitated by the BioImage® program BioImage, Ann Arbor, Mass., USA. Next, each non-master gel was compared to the "master gel" and manually edited to ensure identification and quantitation of spots not found initially by the computer program. This comparison was performed by the same observer (H.U.A.) using the BioImage® program. Following this, the gels were matched by the BioImage® program and the accuracy of the match inspected and corrected by the same observer. Finally, data were extracted for calculations in the Quattro Pro® spreadsheet (Borland version 4.0).

To avoid the presence of duplicate spots in the IEF and NEPHGE subgroups, overlapping spots in either the basic part of IEF gels or in the acidic part of NEPHGE gels were omitted from analysis in the databases and the assay analyses.

Statistical analysis. Two different analyses were applied to distinguish the proteins altered in expression by IL-1$\beta$. In the first analysis, an alteration was considered significant if the average % IOD of a spot in IL-1$\beta$-exposed gels was higher or lower than the average % IOD$\pm$2 SD of the same spot in the DB. In the second comparison between the two groups, Student's t test was applied and P<0.01 was chosen as level of significance.

Qualitative reproducibility of the neonatal rat islet protein databases and assay analyses. 1293 to 1411 (IEF) and 605 to 764 (NEPHGE) spots were found in the individual gels used to construct the 15% DB, whereas 1101 to 1200 (IEF) and 462 to 577 (NEPHGE) spots were found in the gels used for the 10% DB (Tables 4 and 5). "Master gels" were made for the 10% EF and NEPHGE DB. In total, 1792 spots were present in 5 of 5 gels in the 15% DB, whereas 1373 spots were present in 5 of 5 gels in the 10% DB, yielding a qualitative reproducibility (the average of the percentage of spots found in 5 of 5 gels) in the subgroups between 75.2% (NEPHGE 10%) and 91.7% (IEF 15%) (Tables 4 and 5) (For each spot present in 5 of 5 gels, the databases consist of spot match number, % IOD for the 5 individual spots, average % IOD, standard deviation of % IOD, CV % of % IOD, MW and pI.).

As demonstrated in Tables 4 and 5, the total number of spots in the individual gels as well as the number and percentage of spots present in 5 of 5 gels were fewer in the 10% DB than in the 15% DB. However, if the databases were extended to include spots present in at least 3 of 5 gels, no differences in the percentage of spots present were found between the two databases (IEF: 15%: 98.8$\pm$1.2; 10%: 97.4$\pm$1.5; NEPHGE: 15%: 94.8$\pm$5.7; 10%: 94.1$\pm$3.5, Tables 4 and 5). In both databases, the percentage of spots present in 5, 4, 3 or 2 of 5 gels were lower in NEPHGE gels than in IEF gels (Tables 4 and 5). The spatial location of the spots present in less than 5 gels was investigated, demonstrating that the spots were not grouped in specific areas of the gels depending on whether the spot was present in 1, 2, 3 or 4 gels.

Intra- and interassay analyses were only performed on 15% gels, since the number of detectable spots was higher in this database. In both analyses, the number of spots in the individual gels as well as the number and percentage of spots present in 5 of 5 gels were slightly (9%-19%) reduced compared to the 15% DB (compare Tables 4 and 6).

Quantitative reproducibility of the neonatal rat islet protein databases and assay analyses. The quantitative reproducibility was defined as the average of the CV % of % IOD for each spot present in 5 of 5 gels. For the databases, the average CV % was at a comparable level (42.4%-45.7%) in both 10% and 15% IEF and NEPHGE subgroups of gels (Table 7). For all DB subgroups the CV % ranged between 3.0% and 167.9% (Table 7). For interassay analyses, the average CV % were 35.5%-36.1% for both IEF and NEPHGE gels, whereas the average CV % was 30.2% for the intraassay analysis of IEF gels and 45.7% for NEPHGE gels.

Subsequently, the database spots present in all gels were ranked in increasing order of CV % of % IOD, resulting in similar sigmoid-shaped curves for spots in all four database subgroups. Thus, 30% of the spots had a CV % that was lower than 29.7%-32.5%, 50% of the spots had a CV % that was lower than 37.8%-42.8%, 90% of the spots had a CV % that was lower than 68.4%-80.6%. The slopes of the curves indicate that the 5%-10% spots with the highest CV % contribute significantly to the average CV % of % IOD. This is supported by the fact that the median values of the database subgroups are 2.3% to 5.5% lower than the mean values of the subgroups (Table 7).

Regression analyses between the average % IOD and CV % of % IOD for each spot in the database subgroups. In the NEPHGE 10% and 15% DB subgroups, 2 and 6, respectively, of the 10 spots with the highest average IOD % were found in the percentile with the lowest CV % (see above). Although none of the 10 spots with the highest average IOD % were found in this percentile in the IEF DB subgroups, regression analyses were performed to investigate whether a correlation existed between spot average % IOD and CV %. Regression analyses demonstrated that a significant negative correlation existed between these two parameters (range: p=O (IEF 10%)-p=0.00288 (IEF 15%)). However, since the $R^2$-values were very low for all subgroups (range: $R^2$=0.0072 IEF 15%) $R^2$=0.0317 (IEF 10%)), the majority of the variability-of CV % is not explained by variation in average % IOD.

Application of the 10% IEF and NEPHGE DB to distinguish proteins altered in expression by IL-1β. In a recent paper, we demonstrated that IL-1βB up and downregulated 29 and 4 proteins, respectively in 2-D gels of neonatal rat islet proteins (Andersen, et al., *Diabetes* 44:400-407 (1991)). 10% gels were prepared from (35S)-methionine labelled Wistar Furth neonatal rat islets cultured under similar conditions as the present study. Consequently, the rat islet 10% IEF and NEPHGE DB was used for comparison with the computer analyzed gels of IL-1β-exposed islets, analyzed visually in the previous paper (Andersen, et al., *Diabetes* 44:400-407 (1991)). Using ±2 SD of IOD % of each DB spot as a cutoff level (comparable to the criterion for significant up- or down regulation in the visual analysis), comparison with the 10% DB confirmed 32 of these alterations and as expected identified several new protein changes. Thus, a total of 183 spots were upregulated, 113 downregulated and 34 synthesized de novo by IL-1β (results not shown). When using p<0.01 as a cutoff level in a Student's t test, the final analysis showed that 52 spots were upregulated, 47 downregulated- and 6 synthesized de novo by IL-1β, 13 of these included in the 33 spots selected by visual analysis.

Discussion

In this study, we present a 10% and 15% acrylamide 2-D gel protein DB of neonatal rat islets of Langerhans, comprising the first protein databases of islets or insulin secreting cells in any species. 1792 spots were present in 5 of 5 gels in the 15% DB, whereas 1373 spots were present in 5 of 5 gels in the 10% DB, yielding a qualitative reproducibility between 75.2% and 91.7%. In both databases, the average CV % of % IOD was between 42.4% and 45.7%. Applying the 10% DB to distinguish proteins altered in expression by IL-1β, 105 currently unidentified protein spots were found to be up-/downregulated or synthesized de novo by IL-1β.

Characteristics of neonatal Wistar Furth rat islets. To reduce variability, the inbred Wistar Furth strain of rats was chosen as an islet donor for our databases. This strain is the inbred variant of the outbred Wistar routinely used for islet experiments in our lab (Andersen, et al., *Diabetes* 43:770-777 (1994)). We have previously determined that the function of Wistar Furth neonatal rat islets cultured with or without IL-1β is comparable to that of Wistar neonatal rat islets (Andersen, et al. *Diabetes* 44:400-407 (1995); Andersen, et al., *Acta Endocrinol*. 120:92-98 (1989)) and have determined the effects of IL-1β on the 2-D gel protein pattern of Wistar Furth islets (Andersen, et al. *Diabetes* 44:400-407 (1995)). Since the present databases are based on neonatal, and not adult rat islets, we can not exclude that the protein pattern of adult islets will be different. However, adult and neonatal islets from outbred Wistar rats are equally sensitive to the deleterious effect of IL-1. (Mandrup-Poulsen, et al., *Diabetes* 36:641-647 (1987)).

Each litter of newborn rats used for islet isolation typically consists of 8-12 pups with a varying frequency of males and females. Since comparison of Coomassie Blue-stained gels of liver proteins from male and female outbred Wistar rats revealed quantitative differences in 7 of 250 analyzed spots and since six proteins were found exclusively in males and one protein exclusively in females (Steiner, et al., *Electrophoresis* 16:1969-1976 (1995)), it is likely that some of the proteins in our database are gender-specific or gender-regulated. Consequently, it is possible that the high variation of some of the spots in our databases could be reduced if we had chosen to construct separate databases of islets from male and female rats. However, the gels of liver proteins were performed on non-cultured cells which could mean that the sex-determined protein variability could be induced by circulating sex steroids and not an inherent trait of the liver cells per se. Circulating hormones are not likely to interfere in our protein pattern since I) we preculture our islets for 4 days before experiments and II) no differences in serum concentrations of sex steroids are found before puberty. Further, we have previously demonstrated that islets from male and female outbred Wistar rats are equally sensitive to the deleterious effect of IL-1 (Steiner, et al., *Electrophoresis* 16:1969-1976 (1995)).

Detection of islet proteins. Not all spots detected in our databases will represent different protein entities, since some spots can represent modifications (e.g. acetylation, methylation, phosphorylation or carbamylation) of other proteins. However, the detected number of spots is an underestimation of the total number of islet proteins, since the protein database does not include proteins below the limit of sensitivity, proteins not containing methionine, proteins with a molecular weight below 6 kDa or above 250 kDa or proteins with a pH below 3.5 or above 10.5. Further, about 40% of the spots with IODs above limits of detection have previously been estimated to be missed because they are obscured by other spots (Garrels, *J. Biol. Chem*. 264:5269-5282 (1989)). Finally, the 4 h labelling period favours the labelling of proteins with high synthesis rates, whereas longer labelling periods could be required to produce databases where all proteins are in steady-state.

Qualitative reproducibility. Previous reports of the qualitative reproducibility of 2-D gel protein databases are few and the results variable: In a mouse liver protein database of Coomassie Blue-stained 2-D gels, 826 spots were present in the master image and on the average 500 spots were matched in 85% of the other mouse liver patterns (Giometti, et al., *Electrophoresis* 13:970-991 (1992)). In protein databases of ($^{35}$S)-methionine labelled mouse embryos over 80% of spots in each of the four gel images were automatically matched to the standard image (Shi, et al., *Molec. Reprod. Develop.* 37:34-47 (1994)). In our study, 1792 spots (75.2%-91.7%) were present in 5 of 5 gels in the 15% DB, whereas the average percentage of spots present in 5 of 5 gels was 5-10% lower in the 10% DB. This is presumably due to the fact that fewer proteins exist in the high molecular weight region only analyzable on the 10% gels than in the low molecular weight region only analyzable on the 15% gels. In all groups analyzed, the qualitative reproducibility of NEPHGE gels was lower than EF gels. Since NEPHGE gels, contrary to EF gels, are non-equilibrium gels the risk that identical spots have a slightly different horizontal location is increased. However, our manual editing have ascertained that this problem has been eliminated as much as possible.

Quantitative reproducibility. Regarding the quantitative reproducibility, comparisons with other studies are difficult, since the methods used for spot identification are not identical. Further, the spots included in calculations of CV % of % IOD in most of the previously published databases are selected from the total number of matched spots according to varying criteria. In ten Coomassie Blue-stained gels of male and female Wistar rat liver proteins, 250 of more than 1,000 spots present in the "master gel" were selected according to good shape, size and resolution and the presence and good quality in previous experiments (Steiner, et al., *Electrophoresis* 16:1969-1976 (1995)). Using these criteria, one third of the spots had a CV % below 20%, more than half had a CV % below 30% and three quarters had a CV % below 40% (Steiner, et al., *Electrophoresis* 16:1969-1976 (1995)). In ($^{35}$S)-methionine labelled protein databases consisting of 5 gels of compacted eight-cell (CEC) mouse embryos and 4 gels of blastocyst-stage (BS) mouse embryos, 1,674 and 1,653 spots, respectively, were matched in all gels (Shi, et al., *Molec. Reprod. Develop.* 37:34-47(1994)). Calculated on the basis of all matched spots, the percentage error (defined as SEM×100/average) of 74% (CEC) or 79% (BS) of these spots was below 50%, and 45% (CEC) or 47% (BS) of the spots had a percentage error below 30% (Shi, et al., *Molec. Reprod. Develop.* 37:34-47 (1994)). For comparison, conversion of SD's to SEM's (SEM=SD/$\sqrt{n}$) would give an average CV % of 20.3% in the islet IEF 15% DB, and 97.7% and 83.2% of the spots would have a percentage error below 50% and 30%, respectively.

Although the quantitative reproducibility of our study. is comparable to or even better than the study in mouse embryos (Shi, et al., *Molec. Reprod. Develop.* 37:34-47 (1994)), the average CV % of % IOD in our databases are still relatively high. As previously mentioned, the heterogeneous cell population of islets and the different male/female ratio of the islet isolations could contribute to gel variability. Although we have attempted to use gels with comparable total optical densities (the largest difference within each subgroup was by a factor of 3.5 (gel DB10 vs. gel DB3, IEF 15% DB, Table 3)), the non-linear saturation of X-ray film will contribute to the size of the CV % for all database spots. The application of phosphoimaging, a technique not available in our laboratory when this study was initiated, would reduce the contribution of this phenomenon to the magnitude of the CV %. Finally, electronic noise and differences in spot boundary definition in the computer analysis can contribute to the magnitude of the CV %. Contrary to some other gel analysis programs, the BioImage® program uses the local, and not the total background for boundary definition, reducing the contribution of the latter factor to the CV %.

Studies of replicate gels. In a study of 10 replicate gels of ($^{35}$S)-methionine labeled REF 52 cells, Garrels selected 1109 of the most prominent spots out of a total of approximately 2,000 spots and found an average CV % of 26.5%, with a range between <5% and >100% and a modal value between 10% and 15% (Garrels, *J. Biol. Chem.* 264:5269-5282 (1989)). It is unclear whether the samples were analyzed in consecutive or the same set of gels. When grouping the spots according to spot quality (fitting to Gaussian shapes, overlapping of neighboring spots) and omitting spots with low density in all gels, the 19.1% spots of the highest quality had an average CV % of 13.0% (Garrels, *J. Biol. Chem.* 264:5269-5282 (1989)). As expected, the average CV % of % IOD was reduced when the 15% IEF and NEPHGE interassay analyses were compared to the 15% IEF DB, the reduction being by approximately 9%. Since the day-to-day variation of gel preparation was eliminated in the intraassay analyses, the average CV % was expected to decrease even more. In the 15% IEF subgroup, CV % was decreased by ≈15% compared to the database, whereas no decrease was found in the 15% NEPHGE subgroup. The reason for the high average CV % in the 15% NEPHGE intraassay subgroup, which also has the lowest qualitative reproducibility of all subgroups (Tables 4-6), is unknown. As the database gels were also analyzed in one set of gels, the fraction of the CV % that is attributable to biological variation should be given by the difference in CV % between database and intraassay analysis for a given spot. Thus, if the result of the 15% NEPHGE intraassay analysis is disregarded, approximately one third of the average CV % of % IOD is due to biological variation.

Effects of IL-1β on islet protein expression. IL-1β altered the expression of 105 so far unidentified proteins. IL-1β mechanism of action on islet cells is not fully clarified, but three distinct groups of proteins might play important roles: proteins participating in signal-transduction and proteins encoded by so-called early response and late response genes (Eizirik, et al., *Diabetologia* 39:875-890 (1996)). IL-1β-induced signal transduction in target cells is thought to involve four major signalling pathways: nuclear factor-κb, the stress-activated protein kinases (SAPK/JNK), protein kinase C and tyrosine kinase (Mandrup-Poulsen, T., *Diabetologia* 39:1005-1029 (1996); Eizirik, et al., *Diabetologia* 39:875-890 (1996)). The three pathways lead to a rapid and transient induction of the early response genes of which c-fos, c-jun and interferon response factor-1 have been implicated in cytokine action on islet cells. The early response genes activate specific genes with possible deleterious (iNOS, cycloxygenase-2 and lipoxygenase) and protective (HSP72, haem oxygenase, Mn superoxide dismustase) action on islets (Mandrup-Poulsen, T., *Diabetologia,* 39:1005-1029 (1996); Eizirik, et al., *Diabetologia* 39:875-890 (1996)). Thus, the information about IL-1β mechanism of action in islet cells is still limited and the identification of the 105 proteins altered in expression by IL-1β might lead to new knowledge about signal transduction and proteins with protective and deleterious actions.

CONCLUSION

We have established a protein database of neonatal rat islets of Langerhans with a high qualitative reproducibility and a quantitative reproducibility that improves on previously published databases on other cells and tissues. Further, we have determined intra- and interassay variations of the neonatal rat islet protein database. The database has further been applied to identify proteins altered in expression by IL-1β, which might have important roles in an IL-1β mechanism of action. Since IL-1β is cytotoxic to the insulin producing rat B cells, identification of these proteins, currently being performed by mass spectrometry and microsequencing, is expected to result in significant knowledge about the pathogenesis of insulin dependent diabetes mellitus.

TABLE 3

Correction factors between the total optical densities of master and non-master gels in DB, intra- and interassay analyses of 2-D gels of neonatal rat islet proteins.

15% gels

| DB | | Interassay | | Intraassay | |
|---|---|---|---|---|---|
| IEF | | | | | |
| gel DB10 (master): | 1 | gel IE3: | 1 | gel IA2: | 1 |
| gel DB3: | 0.293 | gel IE4: | 1.096 | gel IA3: | 0.620 |
| gel DB6: | 0.303 | gel IE8: | 1.129 | gel IA4: | 0.738 |
| gel DB8: | 0.840 | gel IE9: | 0.784 | gel IA6: | 1.014 |
| gel DB9: | 0.284 | gel IE10: | 0.804 | gel IA10: | 0.747 |
| NEPHGE | | | | | |
| gel DB10 (master): | 1 | gel IE3: | 1 | gel IA1: | 1 |
| gel DB3: | 0.542 | gel IE4: | 1.901 | gel IA2: | 1.599 |
| gel DB6: | 1.067 | gel IE8: | 1.761 | gel IA3: | 0.841 |
| gel DB8: | 0.986 | gel IE9: | 1.408 | gel IA4: | 0.908 |
| gel DB9: | 0.831 | gel IE10: | 1.599 | gel IA5: | 1.135 |

TABLE 3-continued

Correction factors between the total optical densities of master and non-master gels in DB, intra- and interassay analyses of 2-D gels of neonatal rat islet proteins.

10% gels

| IEF | | NEPHGE | |
|---|---|---|---|
| DB | | DB | |
| gel DB10 (master): | 1 | gel DB10 (master): | 1 |
| gel DB1: | 0.947 | gel DB1: | 1.660 |
| gel DB4: | 0.358 | gel DB7: | 3.215 |
| gel DB6: | 1.167 | gel DB8: | 2.959 |
| gel DB8: | 1.145 | gel DB9: | 1.197 |

The databases were based on 10 different isolates analyzed in one set of gels, while interassay analysis consisted of 10 gels of the same sample analyzed in one set of gels and interassay analysis was based on the analysis of the same sample run in 10 consecutive sets of gels on different days. Before computer analysis, one gel in each database subgroup was arbitrarily selected to be the "master gel" used for comparison with the other 4 database gels, the 5 intraassay gels and the 5 interassay gels. The numbers (1-10) of the isolates/replicates chosen are indicated in the Table. The correction factors between the total optical densities of the master and non-master gels were calculated in the BioImage ® program following analysis. Gels with a correction factor <1 have a higher total optical density than the "master gel", e.g., in the 15% IEF DB, the DB10 = 0.293 × gel DB3. For the intra- and interassay analyses, correction factors were calculated between an arbitrarily selected gel and the 4 other gels. Comparison cannot be made between subgroups because gels with a correction factor of 1 not necessarily have the same intensity.

TABLE 4

Reproducibility of spot detection in 15% IEF and NEPHGE 2-DGE DB of neonatal rat islet proteins.

| | total no. of spots | spots in 5 of 5 gels | | spots in 4-5 of 5 gels | | spots in 3-5 of 5 gels | | spots in 2-5 of 5 gels | |
|---|---|---|---|---|---|---|---|---|---|
| | | no. | % | no. | % | no. | % | no. | % |
| IEF | | | | | | | | | |
| gel DB3 | 1325 | 1235 | 93.2 | 1299 | 98.0 | 1320 | 99.6 | 1325 | 100 |
| gel DB6 | 1352 | 1235 | 91.3 | 1322 | 97.8 | 1346 | 99.6 | 1352 | 100 |
| gel DB8 | 1293 | 1235 | 95.5 | 1276 | 98.7 | 1287 | 99.5 | 1292 | 99.9 |
| gel DB9 | 1355 | 1235 | 91.1 | 1319 | 97.3 | 1339 | 98.8 | 1355 | 100 |
| gel DB10 | 1411 | 1235 | 87.5 | 1327 | 94.0 | 1365 | 96.7 | 1398 | 99.1 |
| avg ± SD | | | 91.7 ± 3.0 | | 97.2 ± 1.8 | | 98.8 ± 1.2 | | 99.8 ± 0.4 |
| NEPHGE | | | | | | | | | |
| gel DB3 | 663 | 557 | 84.0 | 604 | 91.1 | 633 | 95.5 | 658 | 99.2 |
| gel DB6 | 605 | 557 | 92.1 | 584 | 96.5 | 598 | 98.8 | 604 | 99.8 |
| gel DB8 | 629 | 557 | 88.6 | 597 | 94.9 | 614 | 97.6 | 623 | 99.0 |
| gel DB9 | 634 | 557 | 87.9 | 601 | 94.8 | 617 | 97.3 | 630 | 99.4 |
| gel DB10 | 764 | 557 | 72.9 | 610 | 79.8 | 648 | 84.4 | 701 | 91.8 |
| avg ± SD | | | 85.1 ± 7.4 | | 91.4 ± 6.8 | | 94.8 ± 5.7 | | 97.8 ± 3.4 |

Construction of the 2-D gel database: neonatal rat islets from 5 different isolates were cultured for 24 h in RPMI 1640 + 0.5% HS, washed twice and labelled for 4 h with ($^{35}$S)-methionine. Following 2-DGE (see Materials and Methods) in one set of gels, the fluorographs were scanned and spots were identified and quantitated by the BioImage ® program. Each gel was compared and matched to the arbitrarily selected "master gel" (gel DB10). For each gel, the table indicates the number and percentage of spots present in (from left to right) all gels, at least 4 of 5 gels, at least 3 of 5 gels and at least 2 of 5 gels.

TABLE 5

Reproducibility of spot detection in 10% IEF and NEPHGE 2-DGE DB of neonatal rat islet proteins.

| | total no. of spots | spots in 5 of 5 gels | | spots in 4-5 of 5 gels | | spots in 3-5 of 5 gels | | spots in 2-5 of 5 gels | |
|---|---|---|---|---|---|---|---|---|---|
| | | no. | % | no. | % | no. | % | no. | % |
| IEF | | | | | | | | | |
| gel DB1 | 1101 | 995 | 90.4 | 1060 | 96.3 | 1070 | 97.2 | 1072 | 97.4 |
| gel DB4 | 1200 | 995 | 82.9 | 1094 | 91.2 | 1143 | 95.3 | 1163 | 96.9 |
| gel DB6 | 1120 | 995 | 88.8 | 1075 | 96.0 | 1106 | 98.8 | 1108 | 98.9 |
| gel DB8 | 1119 | 995 | 88.9 | 1084 | 96.9 | 1106 | 98.8 | 1113 | 99.5 |
| gel DB10 | 1198 | 995 | 83.1 | 1106 | 92.3 | 1162 | 97.0 | 1193 | 99.6 |
| avg ± SD | | | 86.8 ± 3.5 | | 94.5 ± 2.6 | | 97.4 ± 1.5 | | 98.5 ± 1.2 |
| NEPHGE | | | | | | | | | |
| gel DB1 | 516 | 378 | 73.3 | 438 | 84.9 | 475 | 92.1 | 489 | 94.8 |
| gel DB7 | 462 | 378 | 81.8 | 424 | 91.8 | 442 | 95.7 | 445 | 96.3 |
| gel DB8 | 480 | 378 | 78.8 | 440 | 91.7 | 468 | 97.5 | 472 | 98.3 |
| gel DB9 | 492 | 378 | 76.8 | 441 | 89.6 | 474 | 96.3 | 482 | 98.0 |
| gel DB10 | 577 | 378 | 65.5 | 455 | 78.9 | 513 | 88.9 | 539 | 93.4 |
| avg ± SD | | | 75.2 ± 6.3 | | 87.4 ± 5.5 | | 94.1 ± 3.5 | | 96.2 ± 2.1 |

Construction of the 2-D gel database: neonatal rat islets from 5 different isolates were cultured for 24 h in RPMI 1640 + 0.5% HS, washed twice and labelled for 4 h with ($^{35}$S)-methionine. Following 2-DGE (see Materials and Methods) in one set of gels, the fluorographs were scanned and spots were identified and quantitated by the BioImage ® program. Each gel was compared and matched to the arbitrarily selected "master gel" (gel DB10). For each gel, the table indicates the number and percentage of spots present in (from left to right) all gels, at least 4 of 5 gels, at least 3 of 5 gels and at least 2 of 5 gels.

TABLE 6

Reproducibility of spot detection in replicate 15% IEF and NEPHGE 2-D gels of neonatal rat islet proteins.

| Intraassay analysis | total no. of spots | spots in 5 of 5 gels | | Interassay analysis | IEF | total no. of spots | spots in 5 of 5 gels | |
|---|---|---|---|---|---|---|---|---|
| | | no. | % | | | | no. | % |
| IEF | | | | | | | | |
| gel IA2 | 1289 | 1085 | 84.2 | | gel IE3 | 1319 | 1082 | 82.0 |
| gel IA3 | 1337 | 1085 | 81.2 | | gel IE4 | 1348 | 1082 | 80.3 |
| gel IA4 | 1289 | 1085 | 84.2 | | gel IE8 | 1333 | 1082 | 81.2 |
| gel IA6 | 1303 | 1085 | 83.3 | | gel IE9 | 1342 | 1082 | 83.2 |
| gel IA10 | 1326 | 1085 | 81.8 | | gel IE10 | 1300 | 1082 | 80.6 |
| avg ± SD | | | 82.9 ± 1.4 | | avg ± SD | | | 81.5 ± 1.2 |
| NEPHGE | | | | | | | | |
| gel IA1 | 526 | 345 | 65.6 | | gel IE3 | 574 | 421 | 75.0 |
| gel IA2 | 542 | 345 | 63.7 | | gel IE4 | 589 | 421 | 73.3 |
| gel IA3 | 538 | 345 | 64.1 | | gel IE8 | 566 | 421 | 71.5 |
| gel IA4 | 565 | 345 | 61.1 | | gel IE9 | 590 | 421 | 74.4 |
| gel IA5 | 450 | 345 | 76.7 | | gel IE10 | 561 | 421 | 71.4 |
| avg ± SD | | | 66.2 ± 6.1 | | avg ± SD | | | 73.1 ± 1.6 |

For intraassay analysis, 5 independent gels of the same islet cell lysate were analyzed in one set of gels.
For interassay analysis, 5 independent gels of the same islet cell lysate were analyzed in consecutive sets of gels on different days.
Different islet isolates were used for database, intra- and interassay analysis. When analyzed in the BioImage ® program, the fluorographs were compared and matched to the 15% IEF of the NEPHGE "master gel" of Table 2.

TABLE 7

Average coefficients of variance of % integrated optical density of spots detectable in 5 of 5 gels in databases and replicate 2-D gels of neonatal rat islet proteins.

| Analysis | Average CV % | Median (Range) CV % |
|---|---|---|
| IEF 15% DB | 45.4 ± 25.0 | 39.9 (5.0-165.3) |
| IEF 15% Interassay | 36.1 ± 19.8 | 32.6 (2.7-190.6) |
| IEF 15% Intraassay | 30.2 ± 17.1 | 27.3 (0.0-130.4) |
| NEPHGE 15% DB | 44.3 ± 22.5 | 42.0 (3.9-155.1) |
| NEPHGE 15% Interassay | 35.5 ± 19.7 | 33.1 (2.2-118.5) |
| NEPHGE 15% Intraassay | 45.7 ± 22.8 | 43.9 (4.3-130.9) |
| IEF 10% DB | 45.7 ± 21.3 | 42.7 (3.0-133.4) |
| NEPHGE 10% DB | 42.4 ± 22.4 | 37.7 (7.3-167.9) |

The average coefficient of variance (CV %) was calculated from the CV % of % IOD of all spots present in 5 of 5 gels in each subgroup of analysis. Results are presented as means ± SD (left column) and as medians (ranges). The number of spots in 5 of 5 gels in each subgroup is shown in Tables 2-4. For details of design databases and replicate analyses, please see Materials and Methods.

TABLE 8

Proteins Present in Unaffected or Normal Rat Islet Cells

| | IEF 10% gels | | | | NEPHGE 10% gels | | |
|---|---|---|---|---|---|---|---|
| match no. | % IOD ratio | mw | pI | match no. | % IOD ratio | mw | pI |
| 11 | 2.34 | 118,652 | 6.44 | 7 | 0.38 | 65,522 | 7.28 |
| 15 | 0.29 | 75,443 | 6.01 | | | | |
| 25 | 1.79 | 54,244 | 5.53 | 17 | 5.09 | 39,973 | 8.29 |
| 28 | 2.65 | 65,798 | 5.06 | | | | |
| 83 | 2.56 | 164,145 | 6.34 | 102 | 0.45 | 63,560 | 7.26 |
| 85 | 4.21 | 164,145 | 6.28 | | | | |
| 115 | 2.56 | 175,154 | 5.23 | 129 | 0.32 | 57,609 | 7.72 |
| 145 | 8.51 | 133,052 | 6.29 | 130 | 0.45 | 55,734 | 8.07 |
| | | | | 156 | 3.22 | 55,550 | 8.71 |
| 186 | 22.00 | 152,077 | 5.01 | 169 | 2.16 | 55,642 | 8.23 |
| 187 | 6.19 | 152,077 | 4.95 | 171 | 0.21 | 52,860 | 8.20 |
| 189 | 1.88 | 135,100 | 4.96 | 174 | 0.43 | 53,830 | 7.92 |
| 194 | 3.31 | 139,291 | 4.65 | 176 | 0.21 | 52,598 | 7.96 |
| 201 | 2.48 | 143,611 | 4.10 | 181 | 0.20 | 49,422 | 7.40 |
| 210 | 3.19 | 114,519 | 6.40 | 182 | 0.55 | 54,098 | 7.61 |
| | | | | 203 | 1.51 | 44,362 | 8.19 |
| 225 | 4.06 | 83,281 | 5.89 | 211 | 0.28 | 47,925 | 7.28 |
| 265 | 3.31 | 120,019 | 4.99 | 227 | 0.29 | 43,939 | 8.43 |
| 267 | 2.12 | 92,500 | 4.78 | 231 | 0.41 | 44,362 | 8.34 |
| 276 | 2.52 | 107,498 | 4.34 | 236 | 0.16 | 43,162 | 7.90 |
| 279 | 6.78 | 121,401 | 4.20 | 253 | 0.25 | 39,106 | 9.05 |
| | | | | 269 | 9.04 | 39,863 | 8.01 |
| 289 | 1.95 | 73,880 | 6.44 | 296 | 2.96 | 36,169 | 8.29 |
| 306 | 2.65 | 75,706 | 6.20 | 298 | 0.07 | 36,382 | 8.32 |
| 310 | 1.88 | 69,383 | 5.70 | 306 | 0.09 | 35,666 | 8.14 |
| 329 | 2.23 | 72,856 | 5.27 | 310 | 0.27 | 35,827 | 7.57 |
| 330 | 2.74 | 68,809 | 5.35 | 326 | 0.17 | 34,521 | 8.62 |
| | | | | 328 | 0.03 | 30,920 | 8.48 |
| | | | | 334 | 0.11 | 30,920 | 8.17 |
| 342 | 2.80 | 83,281 | 4.81 | | | | |
| 354 | 6.23 | 70,358 | 4.30 | | | | |
| 358 | 0.19 | 76,975 | 4.11 | | | | |
| 382 | 2.55 | 63,920 | 6.35 | | | | |
| 387 | 2.41 | 64,342 | 6.14 | | | | |
| 425 | 2.09 | 67,198 | 5.18 | | | | |
| 436 | 0.38 | 66,407 | 4.76 | | | | |
| 441 | 0.22 | 66,758 | 4.62 | | | | |
| 442 | 0.16 | 66,934 | 4.53 | | | | |
| 471 | 2.81 | 60,722 | 6.08 | | | | |
| 483 | 1.72 | 61,204 | 5.71 | | | | |
| 484 | 0.27 | 59,247 | 5.88 | | | | |
| 505 | 2.30 | 61,526 | 5.41 | | | | |
| 506 | 2.34 | 60,007 | 5.42 | | | | |
| 507 | 2.72 | 59,928 | 5.33 | | | | |
| 510 | 0.26 | 54,485 | 5.27 | | | | |
| 561 | 2.52 | 49,312 | 6.00 | | | | |
| 563 | 3.04 | 48,018 | 6.20 | | | | |
| 655 | 1.85 | 41,355 | 6.15 | | | | |
| 665 | 0.33 | 42,243 | 5.82 | | | | |
| 719 | 0.69 | 39,558 | 6.55 | | | | |
| 759 | 2.40 | 37,116 | 5.34 | | | | |
| 825 | 0.13 | 35,027 | 5.10 | | | | |
| 831 | 0.53 | 34,623 | 4.76 | | | | |
| 882 | 0.10 | 30,920 | 4.94 | | | | |
| 887 | 0.24 | 30,837 | 4.76 | | | | |
| 895 | 0.69 | 28,893 | 4.29 | | | | |
| 908 | 0.27 | 25,753 | 6.28 | | | | |
| 939 | 0.37 | 25,851 | 5.09 | | | | |
| 941 | 0.08 | 22,704 | 5.15 | | | | |
| 949 | 0.21 | 26,803 | 4.49 | | | | |
| 1,081 | 2.68 | 63,836 | 5.43 | | | | |
| 1,342 | 3.74 | 53,379 | 4.64 | | | | |

The match numbers of the table correspond to the match numbers of the 10% IEF and NEPHGE DBs.
The spot numbers given in a previous paper (i2) to spots aftered in expression by IL-1 B are indicated in parenthesis.
* indicates that the spot was not previously found to be aftered in expression by IL-1 B alone but by other experimental conditions (12).
For I EF and N EPHG E gels, the analysis was based on 5 DB gels and 3 IL-LB gels and P < 0.01 was chosen. level of signfficance.
The % IOD ratio expresses the average % IOD of IL-1 B gels/average % IOD of DB gels. Thus, a ratio above 1 indicates that the spot is upregulated. DN indicates that the spot is synthesized de novo by IL-1 B.

TABLE 9

Affected Proteins up-/down-regulated or synthesized de novo by IL-l B Treatment or Expected to be up-/down-regulated or synthesized de novo in Islet Cells when Immunologically Affected in IDDM.

| | IEF 10% gels | | | | NEPHGE 10% gels | | |
|---|---|---|---|---|---|---|---|
| match no. | % IOD ratio | mw | pI | match no. | % IOD ratio | mw | pI |
| | | | | 1 | 0.17 | 58,801 | 8.27 |
| 11 | 2.34 | 118,652 | 6.44 | 7 | 0.38 | 65,522 | 7.28 |
| 15 | 0.29 | 75,443 | 6.01 | | | | |
| 25 | 1.79 | 54,244 | 5.53 | 17 | 5.09 | 39,973 | 8.29 |
| 28 | 2.65 | 65,798 | 5.06 | | | | |
| 83 | 2.56 | 164,145 | 6.34 | 102 | 0.45 | 63,560 | 7.26 |
| 85 | 4.21 | 164,145 | 6.28 | | | | |
| 115 | 2.56 | 175,154 | 5.23 | 129 | 0.32 | 57,609 | 7.72 |
| 145 | 8.51 | 133,052 | 6.29 | 130 | 0.45 | 55,734 | 8.07 |
| | | | | 156 | 3.22 | 55,550 | 8.71 |
| 186 | 22.00 | 152,077 | 5.01 | 169 | 2.16 | 55,642 | 8.23 |
| 187 | 6.19 | 152,077 | 4.95 | 171 | 0.21 | 52,860 | 8.20 |
| 189 | 1.88 | 135,100 | 4.96 | 174 | 0.43 | 53,830 | 7.92 |
| 194 | 3.31 | 139,291 | 4.65 | 176 | 0.21 | 52,598 | 7.96 |
| 201 | 2.48 | 143,611 | 4.10 | 181 | 0.20 | 49,422 | 7.40 |
| 210 | 3.19 | 114,519 | 6.40 | 182 | 0.55 | 54,098 | 7.61 |
| | | | | 203 | 1.51 | 44,362 | 8.19 |
| 225 | 4.06 | 83,281 | 5.89 | 211 | 0.28 | 47,925 | 7.28 |
| 265 | 3.31 | 120,019 | 4.99 | 227 | 0.29 | 43,939 | 8.43 |
| 267 | 2.12 | 92,500 | 4.78 | 231 | 0.41 | 44,362 | 8.34 |
| 276 | 2.52 | 107,498 | 4.34 | 236 | 0.16 | 43,162 | 7.90 |
| 279 | 6.78 | 121,401 | 4.20 | 253 | 0.25 | 39,106 | 9.05 |
| | | | | 269 | 9.04 | 39,863 | 8.01 |
| 289 | 1.95 | 73,880 | 6.44 | 296 | 2.96 | 36,169 | 8.29 |
| 306 | 2.65 | 75,706 | 6.20 | 298 | 0.07 | 36,382 | 8.32 |
| 310 | 1.88 | 69,383 | 5.70 | 306 | 0.09 | 35,666 | 8.14 |
| 329 | 2.23 | 72,856 | 5.27 | 310 | 0.27 | 35,827 | 7.57 |
| 330 | 2.74 | 68,809 | 5.35 | 326 | 0.17 | 34,521 | 8.62 |
| | | | | 328 | 0.03 | 30,920 | 8.48 |
| | | | | 334 | 0.11 | 30,920 | 8.17 |

TABLE 9-continued

Affected Proteins up-/down-regulated or synthesized de novo by IL-1 B Treatment or Expected to be up-/down-regulated or synthesized de novo in Islet Cells when Immunologically Affected in IDDM.

| IEF 10% gels | | | | NEPHGE 10% gels | | | |
|---|---|---|---|---|---|---|---|
| match no. | % IOD ratio | mw | pI | match no. | % IOD ratio | mw | pI |
| 342 | 2.80 | 83,281 | 4.81 | | | | |
| | | | | 668 | DN | 42,809 | 8.46 |
| 354 | 6.23 | 70,358 | 4.30 | | | | |
| 358 | 0.19 | 76,975 | 4.11 | | | | |
| 382 | 2.55 | 63,920 | 6.35 | | | | |
| 387 | 2.41 | 64,342 | 6.14 | | | | |
| 425 | 2.09 | 67,198 | 5.18 | | | | |
| 436 | 0.38 | 66,407 | 4.76 | | | | |
| 441 | 0.22 | 66,758 | 4.62 | | | | |
| 442 | 0.16 | 66,934 | 4.53 | | | | |
| 471 | 2.81 | 60,722 | 6.08 | | | | |
| 483 | 1.72 | 61,204 | 5.71 | | | | |
| 484 | 0.27 | 59,247 | 5.88 | | | | |
| 505 | 2.30 | 61,526 | 5.41 | | | | |
| 506 | 2.34 | 60,007 | 5.42 | | | | |
| 507 | 2.72 | 59,928 | 5.33 | | | | |
| 510 | 0.26 | 54,485 | 5.27 | | | | |
| 561 | 2.52 | 49,312 | 6.00 | | | | |
| 563 | 3.04 | 48,018 | 6.20 | | | | |
| 655 | 1.85 | 41,355 | 6.15 | | | | |
| 665 | 0.33 | 42,243 | 5.82 | | | | |
| 719 | 0.69 | 39,558 | 6.55 | | | | |
| 759 | 2.40 | 37,116 | 5.34 | | | | |
| 825 | 0.13 | 35,027 | 5.10 | | | | |
| 831 | 0.53 | 34,623 | 4.76 | | | | |
| 882 | 0.10 | 30,920 | 4.94 | | | | |
| 887 | 0.24 | 30,837 | 4.76 | | | | |
| 895 | 0.69 | 28,893 | 4.29 | | | | |
| 908 | 0.27 | 25,753 | 6.28 | | | | |
| 939 | 0.37 | 25,851 | 5.09 | | | | |
| 941 | 0.08 | 22,704 | 5.15 | | | | |
| 949 | 0.21 | 26,803 | 4.49 | | | | |
| 1,081 | 2.68 | 63,836 | 5.43 | | | | |
| 1,342 | 3.74 | 53,379 | 4.64 | | | | |
| 1,356 | DN | 147,898 | 5.40 | | | | |

The match numbers of the table correspond to the match numbers of the 10% IEF and NEPHGE DBs.
The spot numbers given in a previous paper (i2) to spots aftered in expression by IL-1B are indicated in parenthesis.
* indicates that the spot was not previously found to be aftered in expression by IL-1B alone but by other experimental conditions (12).
For IEF and NEPHGE gels, the analysis was based on 5 DB gels and 3 IL-LB gels and P < 0.01 was chosen as level of signfficance.
The % IOD ratio expresses the average % IOD of IL-1B gels/average % IOD of DB gels. Thus, a ratio above 1 indicates that the spot is upregulated.
DN indicates that the spot is synthesized de novo by IL-1B.

TABLE 10

Marker Proteins In Islet Cells

| IEF 10% gels | | | | NEPHGE 10% gels | | | |
|---|---|---|---|---|---|---|---|
| match no. | % IOD ratio | mw | pI | match no. | % IOD ratio | mw | pI |
| 11 | 2.34 | 118,652 | 6.64 | 7 | 0.38 | 65,522 | 7.28 |
| 15 | 0.29 | 75,443 | 6.01 | | | | |
| 25 | 1.79 | 54,244 | 5.53 | 17 | 5.09 | 39,973 | 8.29 |
| 28 | 2.65 | 65,798 | 5.06 | | | | |
| 83 | 2.56 | 164,145 | 6.34 | 102 | 0.45 | 63,560 | 7.26 |
| 85 | 4.21 | 164,145 | 6.28 | | | | |
| 115 | 2.56 | 175,154 | 5.23 | 129 | 0.32 | 57,609 | 7.72 |
| 145 | 8.51 | 133,052 | 6.29 | 130 | 0.45 | 55,734 | 8.07 |
| | | | | 156 | 3.22 | 55,550 | 8.71 |
| 186 | 22.00 | 152,077 | 5.01 | 169 | 2.16 | 55,642 | 8.23 |
| 187 | 6.19 | 152,077 | 4.95 | 171 | 0.21 | 52,860 | 8.20 |
| 189 | 1.88 | 135,100 | 4.96 | 174 | 0.43 | 53,830 | 7.92 |
| 194 | 3.31 | 139,291 | 4.65 | 176 | 0.21 | 52,598 | 7.96 |
| 201 | 2.48 | 143,611 | 4.10 | 181 | 0.20 | 49,422 | 7.40 |
| 210 | 3.19 | 114,519 | 6.40 | 182 | 0.55 | 54,098 | 7.61 |
| | | | | 203 | 1.51 | 44,362 | 8.19 |
| 225 | 4.06 | 83,281 | 5.89 | 211 | 0.28 | 47,925 | 7.28 |
| 265 | 3.31 | 120,019 | 4.99 | 227 | 0.29 | 43,939 | 8.43 |
| 267 | 2.12 | 92,500 | 4.78 | 231 | 0.41 | 44,362 | 8.34 |
| 276 | 2.52 | 107,498 | 4.34 | 236 | 0.16 | 43,162 | 7.90 |
| 279 | 6.78 | 121,401 | 4.20 | 253 | 0.25 | 39,106 | 9.05 |
| | | | | 269 | 9.04 | 39,863 | 8.01 |
| 289 | 1.95 | 73,880 | 6.44 | 296 | 2.96 | 36,169 | 8.29 |
| 306 | 2.65 | 75,706 | 6.20 | 298 | 0.07 | 36,382 | 8.32 |
| 310 | 1.88 | 69,383 | 5.70 | 306 | 0.09 | 35,666 | 8.14 |
| 329 | 2.23 | 72,856 | 5.27 | 310 | 0.27 | 35,827 | 7.57 |
| 330 | 2.74 | 68,809 | 5.35 | 326 | 0.17 | 34,521 | 8.62 |
| | | | | 328 | 0.03 | 30,920 | 8.48 |
| | | | | 334 | 0.11 | 30,920 | 8.17 |
| 342 | 2.80 | 83,281 | 4.81 | | | | |
| 354 | 6.23 | 70,358 | 4.30 | | | | |
| 358 | 0.19 | 76,975 | 4.11 | | | | |
| 382 | 2.55 | 63,920 | 6.35 | | | | |
| 387 | 2.41 | 64,342 | 6.14 | | | | |
| 425 | 2.09 | 67,198 | 5.18 | | | | |
| 436 | 0.38 | 66,407 | 4.76 | | | | |
| 441 | 0.22 | 66,758 | 4.62 | | | | |
| 442 | 0.16 | 66,934 | 4.53 | | | | |
| 471 | 2.81 | 60,722 | 6.08 | | | | |
| 483 | 1.72 | 61,204 | 5.71 | | | | |
| 484 | 0.27 | 59,247 | 5.88 | | | | |
| 505 | 2.30 | 61,526 | 5.41 | | | | |
| 506 | 2.34 | 60,007 | 5.42 | | | | |
| 507 | 2.72 | 59,928 | 5.33 | | | | |
| 510 | 0.26 | 54,485 | 5.27 | | | | |
| 561 | 2.52 | 49,312 | 6.00 | | | | |
| 563 | 3.04 | 48,018 | 6.20 | | | | |
| 655 | 1.85 | 41,355 | 6.15 | | | | |
| 665 | 0.33 | 42,243 | 5.82 | | | | |
| 719 | 0.69 | 39,558 | 6.55 | | | | |
| 759 | 2.40 | 37,116 | 5.34 | | | | |
| 825 | 0.13 | 35,027 | 5.10 | | | | |
| 831 | 0.53 | 34,623 | 4.76 | | | | |
| 882 | 0.10 | 30,920 | 4.94 | | | | |
| 887 | 0.24 | 30,837 | 4.76 | | | | |
| 895 | 0.69 | 28,893 | 4.29 | | | | |
| 908 | 0.27 | 25,753 | 6.28 | | | | |
| 939 | 0.37 | 25,851 | 5.09 | | | | |
| 941 | 0.08 | 22,704 | 5.15 | | | | |
| 949 | 0.21 | 26,803 | 4.49 | | | | |
| 1,081 | 2.68 | 63,836 | 5.43 | | | | |
| 1,342 | 3.74 | 53,379 | 4.64 | | | | |

The match numbers of the table correspond to the match numbers of the 10% IEF and NEPHGE DBs.
The spot numbers given in a previous paper (i2) to spots aftered in expression by IL-1B are indicated in parenthesis.
* indicates that the spot was not previously found to be aftered in expression by IL-1B alone but by other experimental conditions (12).
For IEF and NEPHGE gels, the analysis was based on 5 DB gels and 3 IL-LB gels and P < 0.01 was chosen as level of signfficance.
The % IOD ratio expresses the average % IOD of IL-1B gels/average % IOD of DB gels. Thus, a ratio above 1 indicates that the spot is upregulated.
DN indicates that the spot is synthesized de novo by IL-1B.

TABLE 11

Optional Proteins Present in Unaffected or Normal Islet Cells

| match no. | IEF 10% gels | | | match no. | NEPHGE 10% gels | | |
| --- | --- | --- | --- | --- | --- | --- | --- |
| | % IOD ratio | mw | pI | | % IOD ratio | mw | pI |
| 10(7-) | 11.57 | 120,478 | 7.27 | 9(3) | 0.12 | 115,709 | 8.33 |
| | | | | 18(18) | 0.27 | 36,415 | 8.44 |
| | | | | 123(8) | 0.29 | 57,040 | 8.17 |
| 173(3) | 2.47 | 136,657 | 5.38 | | | | |
| 217(8) | 4.73 | 91,294 | 6.12 | | | | |
| 285(10) | 6.01 | 78,333 | 6.66 | | | | |
| 339(12) | 0.16 | 72,602 | 5.12 | | | | |
| 340(13) | 0.32 | 71,346 | 5.20 | | | | |
| 344(11-) | 0.44 | 73,622 | 4.95 | | | | |
| 347(14) | 4.05 | 77,651 | 4.62 | | | | |
| 480(18) | 4.20 | 62,014 | 5.91 | | | | |
| 614(21) | 0.27 | 52,937 | 4.76 | | | | |
| 950(26) | 0.19 | 25,753 | 4.53 | | | | |
| 1,196(2) | 9.55 | 143,064 | 5.41 | | | | |

The match numbers of the table correspond to the match numbers of the 10% IEF and NEPHGE DBs.
The spot numbers given in a previous paper (i2) to spots aftered in expression by IL-1B are indicated in parenthesis.
* indicates that the spot was not previously found to be aftered in expression by IL-1B alone but by other experimental conditions (12).
For IEF and NEPHGE gels, the analysis was based on 5 DB gels and 3 IL-LB gels and P < 0.01 was chosen as level of signfficance.
The % IOD ratio expresses the average % IOD of IL-1B gels/average % IOD of DB gels. Thus, a ratio above 1 indicates that the spot is upregulated.
DN indicates that the spot is synthesized de novo by IL-1B.

TABLE 12

Optionally Affected Proteins up-/down-regulated or synthesized de novo by IL-1B Treatment or Expected to be up-/down-regulated or synthesized de novo in Islet Cells when Immunologically Affected in IDDM

| match no. | IEF 10% gels | | | match no. | NEPHGE 10% gels | | |
| --- | --- | --- | --- | --- | --- | --- | --- |
| | % IOD ratio | mw | pI | | % IOD ratio | mw | pI |
| 10(7-) | 11.57 | 120,478 | 7.27 | 9(3) | 0.12 | 115,709 | 8.33 |
| | | | | 18(18) | 0.27 | 36,415 | 8.44 |
| | | | | 123(8) | 0.29 | 57,040 | 8.17 |
| 173(3) | 2.47 | 136,657 | 5.38 | | | | |
| 217(8) | 4.73 | 91,294 | 6.12 | | | | |
| 285(10) | 6.01 | 78,333 | 6.66 | | | | |
| 339(12) | 0.16 | 72,602 | 5.12 | | | | |
| 340(13) | 0.32 | 71,346 | 5.20 | | | | |
| 344(11-) | 0.44 | 73,622 | 4.95 | | | | |
| 347(14) | 4.05 | 77,651 | 4.62 | 670(1) | DN | 148,745 | 8.10 |
| | | | | 672(2) | DN | 132,543 | 8.52 |
| | | | | 673(2) | DN | 132,204 | 8.46 |
| | | | | 674(2) | DN | 132,543 | 8.42 |
| 480(18) | 4.20 | 62,014 | 5.91 | | | | |
| 614(21) | 0.27 | 52,937 | 4.76 | | | | |
| 950(26) | 0.19 | 25,753 | 4.53 | | | | |
| 1,196(2) | 9.55 | 143,064 | 5.41 | | | | |

The match numbers of the table correspond to the match numbers of the 10% IEF and NEPHGE DBs.
The spot numbers given in a previous paper (i2) to spots aftered in expression by IL-1B are indicated in parenthesis.
* indicates that the spot was not previously found to be aftered in expression by IL-1B alone but by other experimental conditions (12).
For IEF and NEPHGE gels, the analysis was based on 5 DB gels and 3 IL-LB gels and P < 0.01 was chosen as level of signfficance.
The % IOD ratio expresses the average % IOD of IL-1B gels/average % IOD of DB gels. Thus, a ratio above 1 indicates that the spot is upregulated.
DN indicates that the spot is synthesized de novo by IL-1B.

TABLE 13

Optional Marker Proteins in Islet Cells

| match no. | IEF 10% gels | | | match no. | NEPHGE 10% gels | | |
|---|---|---|---|---|---|---|---|
| | % IOD ratio | mw | pI | | % IOD ratio | mw | pI |
| 10(7-) | 11.57 | 120,478 | 7.27 | 9(3) | 0.12 | 115,709 | 8.33 |
| | | | | 18(18) | 0.27 | 36,415 | 8.44 |
| | | | | 123(8) | 0.29 | 57,040 | 8.17 |
| 173(3) | 2.47 | 136,657 | 5.38 | | | | |
| 217(8) | 4.73 | 91,294 | 6.12 | | | | |
| 285(10) | 6.01 | 78,333 | 6.66 | | | | |
| 339(12) | 0.16 | 72,602 | 5.12 | | | | |
| 340(13) | 0.32 | 71,346 | 5.20 | | | | |
| 344(11-) | 0.44 | 73,622 | 4.95 | | | | |
| 347(14) | 4.05 | 77,651 | 4.62 | | | | |
| 480(18) | 4.20 | 62,014 | 5.91 | | | | |
| 614(21) | 0.27 | 52,937 | 4.76 | | | | |
| 950(26) | 0.19 | 25,753 | 4.53 | | | | |
| 1,196(2) | 9.55 | 143,064 | 5.41 | | | | |

The match numbers of the table correspond to the match numbers of the 10% IEF and NEPHGE DBs.
The spot numbers given in a previous paper (i2) to spots aftered in expression by IL-1B are indicated in parenthesis.
* indicates that the spot was not previously found to be aftered in expression by IL-1B alone but by other experimental conditions (12).
For IEF and NEPHGE gels, the analysis was based on 5 DB gels and 3 IL-LB gels and P < 0.01 was chosen as level of signfficance.
The % IOD ratio expresses the average % IOD of IL-1B gels/average % IOD of DB gels. Thus, a ratio above 1 indicates that the spot is upregulated.
DN indicates that the spot is synthesized de novo by IL-1B.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for indicating the development of diabetes, comprising: measuring an increase in protein expression of one or more proteins in a blood, urine, or cerebrospinal fluid sample obtained from a test subject relative to protein expression in a control sample, said proteins selected from the group consisting of ELONGATION FACTOR 2 (EF-2); VACUOLAR ATP SYNTHASE SUBUNIT B, BRAIN ISOFORM (EC 3.6.1.34); LAMIN B 1 (mouse); PYRUVATE CARBOXYLASE PRECURSOR (EC 6.4.1.1); MAJOR VAULT PROTEIN; HEAT SHOCK 70 KD PROTEIN AGP-2 (mouse); UBIQUITIN CARBOXYL-TERMINAL HYDROLASE T (EC 3.1.2.15); CALNEXIN PRECURSOR; TRANSITIONAL ENDOPLASMIC RETICULUM ATPASE (TER ATPASE); HEAT SHOCK PROTEIN HSP 90-BETA (HSP 84); GLYCYL-TENA SYNTHETASE (EC 6.1.1.14); 78 KD GLUCOSE REGULATED PROTEIN PRECURSOR (GRP 78); NADPH-CYTOCHROME P450 REDUCTASE (EC 1.6.2.4); MITOCHONDRIAL STRESS-70 PROTEIN PRECURSOR (MORTALIN); TURNED ON AFTER DIVISION, 64 KD PROTEIN (TOAD-64); T-COMPLEX PROTEIN 1, GAMMA SUBUNIT (Mouse/Human); COATOMER DELTA SUBUNIT (DELTA-COAT PROTEIN); HEAT SHOCK COGNATE 71 kD PROTEIN; PROTEIN DISULFIDE ISOMERASE ER-60 PRECURSOR (EC 5.3.4.1) (ERP60); T-COMPLEX PROTEIN 1, EPSILON SUBUNIT (TCP-1-EPSILON) (Mouse); MITOCHONDRIAL MATRIXPROTEIN P1 PRECURSOR (GSP-60); ALPHA ENOLASE (EC 4.2.1.11); LAMIN A; TGF-beta RECEPTOR INTERACTING PROTEIN 1 (HUMAN); GLYCERALDEHYDE 3-PHOSPHATE DEHYDROGENASE (EC 1.2.1.12) (GAPDH); POLYPYRIXIDINE TRACT-BINDING PROTEIN (PTB) (HNRNP I); 6-PHOSPHOFRUCTO-2 KINASE (EC 2.7.1.105); PHOSPHOGLYCERATE KINASE (EC 2.7.2.3); ANNEXIN II (LIPOCORTIN II) (CALPACTIN I HEAVY CHAIN); GLYCERALDEHYDE 3-PHOSPHATE DEHYDROGENASE (EC 1.2.1.12) (GAPDH); GALECTIN-3 (GALACTOSE SPECIFIC LECTIN 3); and FRUCTOSE-BISPHOSPHATE ALDOLASE (EC 4.1.2.13) A (MUSCLE).

2. The method for indicating the development of diabetes according to claim 1, wherein said protein is selected from the group consisting of: HEAT SHOCK 70 KD PROTEIN AGP-2 (mouse); MITOCHONDRIAL STRESS-70 PROTEIN PRECURSOR (MORTALIN); and GALECTIN-3 (GALACTOSE-SPECIFIC LECTIN 3).

* * * * *

SEQUENCE LISTING

<160> NUMBER OF SEQ ID NOS: 10

<210> SEQ ID NO 1
<211> LENGTH: 668
<212> TYPE: PRT
<213> ORGANISM: Mus sp.

<400> SEQUENCE: 1

Met Ile Ser Ala Ser Arg Ala Ala Ala Arg Leu Val Gly Thr Ala
1               5                   10                  15

Ala Ser Arg Ser Pro Ala Ala Ala Arg Pro Gln Asp Gly Trp Asn Gly
            20                  25                  30

Leu Ser His Glu Ala Phe Arg Phe Val Ser Arg Asp Tyr Ala Ser Glu
        35                  40                  45

Ala Ile Lys Gly Ala Val Val Gly Ile Asp Leu Gly Thr Thr Asn Ser
    50                  55                  60

```
Cys Val Ala Val Met Glu Gly Lys Gln Ala Lys Val Leu Glu Asn Ala
 65                  70                  75                  80

Glu Gly Ala Arg Thr Thr Pro Ser Val Val Ala Phe Thr Ala Asp Gly
                 85                  90                  95

Glu Arg Leu Val Met Pro Ala Lys Arg Gln Ala Val Thr Asn Pro Asn
            100                 105                 110

Asn Thr Phe Tyr Ala Thr Lys Arg Leu Ile Gly Arg Arg Tyr Asp Asp
        115                 120                 125

Pro Glu Val Gln Lys Asp Thr Lys Asn Val Pro Phe Lys Ile Val Arg
    130                 135                 140

Ala Ser Asn Gly Asp Ala Trp Val Glu Ala His Gly Lys Tyr Ser Pro
145                 150                 155                 160

Ser Gln Ile Gly Ala Phe Val Leu Met Lys Met Lys Glu Thr Ala Glu
                165                 170                 175

Asn Tyr Leu Gly His Thr Ala Lys Asn Ala Val Ile Thr Val Pro Ala
            180                 185                 190

Tyr Phe Asn Asp Ser Gln Arg Gln Ala Thr Lys Asp Ala Gly Gln Ile
        195                 200                 205

Ser Gly Leu Asn Val Leu Val Ile Asn Glu Pro Thr Ala Ala Ala Leu
    210                 215                 220

Ala Tyr Gly Leu Asp Lys Ser Glu Asp Lys Val Ile Ala Val Tyr Asp
225                 230                 235                 240

Leu Gly Gly Gly Thr Phe Asp Ile Ser Ile Leu Glu Ile Gln Lys Gly
                245                 250                 255

Val Phe Glu Val Lys Ser Thr Asn Gly Asp Thr Phe Leu Gly Gly Asp
            260                 265                 270

Phe Asp Gln Ala Leu Leu Arg His Ile Val Lys Glu Phe Lys Arg Glu
        275                 280                 285

Thr Gly Val Asp Leu Thr Lys Asp Asn Met Ala Leu Gln Arg Val Arg
    290                 295                 300

Glu Ala Ala Glu Lys Ala Lys Cys Glu Leu Ser Ser Ser Val Gln Thr
305                 310                 315                 320

Asp Ile Asn Leu Pro Tyr Leu Thr Asp Ala Ser Gly Pro Lys His Leu
                325                 330                 335

Asn Met Lys Leu Thr Arg Ala Gln Phe Glu Gly Ile Val Thr Asp Leu
            340                 345                 350

Ile Lys Arg Thr Ile Ala Pro Cys Gln Lys Ala Met Gln Asp Ala Glu
        355                 360                 365

Val Ser Lys Ser Asp Ile Gly Glu Val Ile Leu Val Gly Gly Met Thr
    370                 375                 380

Arg Pro Lys Val Gln Gln Thr Val Gln Asp Leu Phe Gly Arg Ala Pro
385                 390                 395                 400

Ser Lys Ala Val Asn Pro Asp Glu Ala Val Ala Ile Gly Ala Ala Ile
                405                 410                 415

Gln Gly Gly Val Leu Ala Gly Asp Val Thr Asp Val Leu Leu Leu Asp
            420                 425                 430

Val Thr Pro Leu Ser Leu Gly Ile Glu Thr Gly Gly Val Phe Thr Lys
        435                 440                 445

Leu Ile Asn Arg Asn Thr Thr Ile Pro Thr Lys Lys Ser Gln Val Phe
    450                 455                 460

Ser Thr Ala Ala Asp Gly Gln Thr Gln Val Glu Ile Lys Val Cys Gln
465                 470                 475                 480
```

```
Gly Glu Arg Glu Met Ala Gly Asp Asn Lys Leu Leu Gly Gln Phe Thr
                485                 490                 495

Leu Ile Gly Pro Pro Ala Pro Arg Gly Val Pro Gln Ile Glu Val Thr
            500                 505                 510

Phe Asp Ile Asp Ala Asn Gly Ile Val His Val Ser Ala Lys Asp Lys
        515                 520                 525

Gly Thr Gly Arg Glu Gln Gln Ile Val Ile Gln Ser Ser Gly Gly Leu
    530                 535                 540

Ser Lys Asp Asp Ile Glu Asn Met Val Lys Asn Ala Lys Tyr Ala Glu
545                 550                 555                 560

Glu Asp Arg Arg Lys Glu Arg Val Glu Ala Val Asn Met Ala Glu
                565                 570                 575

Gly Ile Ile His Asp Thr Glu Thr Lys Met Glu Glu Phe Lys Asp Gln
                580                 585                 590

Leu Pro Ala Asp Glu Cys Asn Lys Leu Lys Glu Glu Ile Ser Lys Val
            595                 600                 605

Arg Ala Leu Leu Ala Lys Asp Ser Glu Thr Gly Glu Asn Ile Arg Gln
        610                 615                 620

Ala Ala Ser Ser Leu Gln Gln Ala Ser Leu Lys Leu Phe Glu Met Ala
625                 630                 635                 640

Tyr Lys Lys Met Ala Ser Glu Arg Glu Gly Ser Gly Ser Ser Gly Thr
                645                 650                 655

Gly Glu Gln Lys Glu Asp Gln Lys Glu Lys Gln
                660                 665

<210> SEQ ID NO 2
<211> LENGTH: 668
<212> TYPE: PRT
<213> ORGANISM: Homo sapiens

<400> SEQUENCE: 2

Met Ile Ser Ala Ser Arg Ala Ala Ala Arg Leu Val Gly Ala Ala
1               5                   10                  15

Ala Ser Arg Gly Pro Thr Ala Ala Arg His Gln Asp Ser Trp Asn Gly
                20                  25                  30

Leu Ser His Glu Ala Phe Arg Leu Val Ser Arg Asp Tyr Ala Ser Glu
            35                  40                  45

Ala Ile Lys Gly Ala Val Val Gly Ile Asp Leu Gly Thr Thr Asn Ser
        50                  55                  60

Cys Val Ala Val Met Glu Gly Lys Gln Ala Lys Val Leu Glu Asn Ala
65                  70                  75                  80

Glu Gly Ala Arg Thr Thr Pro Ser Val Val Ala Phe Thr Ala Asp Gly
                85                  90                  95

Glu Arg Leu Val Met Pro Ala Lys Arg Gln Ala Val Thr Asn Pro Asn
                100                 105                 110

Asn Thr Phe Tyr Ala Thr Lys Arg Leu Ile Gly Arg Arg Tyr Asp Asp
            115                 120                 125

Pro Glu Val Gln Lys Asp Ile Lys Asn Val Pro Phe Lys Ile Val Arg
        130                 135                 140

Ala Ser Asn Gly Asp Ala Trp Val Glu Ala His Gly Lys Tyr Ser Pro
145                 150                 155                 160

Ser Gln Ile Gly Ala Phe Val Leu Met Lys Met Lys Glu Thr Ala Glu
                165                 170                 175

Asn Tyr Leu Gly His Thr Ala Lys Asn Ala Val Ile Thr Val Pro Ala
            180                 185                 190
```

```
Tyr Phe Asn Asp Ser Gln Arg Gln Ala Thr Lys Asp Ala Gly Gln Ile
            195                 200                 205

Ser Gly Leu Asn Val Leu Val Ile Asn Glu Pro Thr Ala Ala Ala Leu
        210                 215                 220

Ala Tyr Gly Leu Asp Lys Ser Glu Asp Lys Val Ile Ala Val Tyr Asp
225                 230                 235                 240

Leu Gly Gly Gly Thr Phe Asp Ile Ser Ile Leu Glu Ile Gln Lys Gly
                245                 250                 255

Val Phe Glu Val Lys Ser Thr Asn Gly Asp Thr Phe Leu Gly Gly Asp
            260                 265                 270

Phe Asp Gln Ala Leu Leu Arg His Ile Val Lys Glu Phe Lys Arg Glu
        275                 280                 285

Thr Gly Val Asp Leu Thr Lys Asp Asn Met Ala Leu Gln Arg Val Arg
290                 295                 300

Glu Ala Ala Glu Lys Ala Lys Cys Glu Leu Ser Ser Val Gln Thr
305                 310                 315                 320

Asp Ile Asn Leu Pro Tyr Leu Thr Asp Ser Ser Gly Pro Lys His Leu
                325                 330                 335

Asn Met Lys Leu Thr Arg Ala Gln Phe Glu Gly Ile Val Thr Asp Leu
            340                 345                 350

Ile Arg Arg Thr Ile Ala Pro Cys Gln Lys Ala Met Gln Asp Ala Glu
        355                 360                 365

Val Ser Lys Ser Asp Ile Gly Glu Val Ile Leu Val Gly Gly Met Thr
370                 375                 380

Arg Pro Lys Val Gln Gln Thr Val Gln Asp Leu Phe Gly Arg Ala Pro
385                 390                 395                 400

Ser Lys Ala Val Asn Pro Asp Glu Ala Val Ala Ile Gly Ala Ala Ile
                405                 410                 415

Gln Gly Gly Val Leu Ala Gly Asp Val Thr Asp Val Leu Leu Leu Asp
            420                 425                 430

Val Thr Pro Leu Ser Leu Gly Ile Glu Thr Gly Gly Val Phe Thr Lys
        435                 440                 445

Leu Ile Asn Arg Asn Thr Thr Ile Pro Thr Lys Lys Ser Gln Val Phe
450                 455                 460

Ser Thr Ala Ala Asp Gly Gln Thr Gln Val Glu Ile Lys Val Cys Gln
465                 470                 475                 480

Gly Glu Arg Glu Met Ala Gly Asp Asn Lys Leu Leu Gly Gln Phe Thr
                485                 490                 495

Leu Ile Gly Pro Pro Ala Pro Arg Gly Val Pro Gln Ile Glu Val Thr
            500                 505                 510

Phe Asp Ile Asp Ala Asn Gly Ile Val His Val Ser Ala Lys Asp Lys
        515                 520                 525

Gly Thr Arg Arg Glu Gln Gln Ile Val Ile Gln Ser Ser Gly Gly Leu
530                 535                 540

Ser Lys Asp Asp Ile Glu Asn Met Val Lys Asn Ala Lys Tyr Ala Glu
545                 550                 555                 560

Glu Asp Arg Arg Lys Lys Glu Arg Val Glu Ala Val Asn Met Ala Glu
                565                 570                 575

Gly Ile Ile His Asp Thr Glu Thr Lys Met Glu Glu Phe Lys Asp Gln
            580                 585                 590

Leu Pro Ala Asp Glu Cys Asn Lys Leu Lys Glu Glu Ile Ser Lys Met
        595                 600                 605
```

```
Arg Glu Leu Leu Ala Lys Asp Ser Glu Thr Gly Glu Asn Ile Arg Gln
    610                 615                 620

Ala Ala Ser Ser Leu Gln Gln Ala Ser Leu Lys Leu Phe Glu Met Ala
625                 630                 635                 640

Tyr Lys Lys Met Ala Ser Glu Arg Glu Gly Ser Gly Ser Ser Gly Thr
                645                 650                 655

Gly Glu Gln Lys Glu Asp Gln Lys Glu Glu Lys Gln
            660                 665
```

<210> SEQ ID NO 3
<211> LENGTH: 258
<212> TYPE: PRT
<213> ORGANISM: Rattus sp.

<400> SEQUENCE: 3

```
Met Ala Asp Gly Phe Ser Leu Asn Asp Ala Leu Ala Gly Ser Gly Asn
1               5                   10                  15

Pro Asn Pro Arg Gly Trp Pro Gly Ala Trp Gly Asn Gln Pro Gly Ala
            20                  25                  30

Gly Gly Tyr Pro Gly Ala Ser Tyr Pro Gly Ala Pro Gly Gln Ala Pro
        35                  40                  45

Pro Gly Gly Tyr Pro Gly Gln Ala Pro Pro Ser Ala Tyr Pro Gly Pro
    50                  55                  60

Thr Gly Pro Ser Ala Tyr Pro Gly Pro Thr Ala Pro Gly Ala Tyr Pro
65                  70                  75                  80

Gly Pro Thr Ala Pro Gly Ala Phe Pro Gly Gln Pro Gly Pro Gly
            85                  90                  95

Ala Tyr Pro Ser Pro Gly Ala Tyr Pro Ser Ala Pro Gly Ala Tyr Pro
            100                 105                 110

Ala Thr Gly Pro Phe Gly Ala Pro Thr Gly Pro Leu Thr Val Pro Tyr
        115                 120                 125

Asp Met Pro Leu Pro Gly Gly Val Met Pro Arg Met Leu Ile Thr Ile
    130                 135                 140

Ile Gly Thr Val Lys Pro Asn Ala Asn Ser Ile Thr Leu Phe Lys Lys
145                 150                 155                 160

Gly Asn Asp Ile Ala Phe His Phe Asn Pro Arg Phe Asn Glu Asn Asn
                165                 170                 175

Arg Arg Val Ile Val Cys Asn Thr Lys Gln Asp Asn Asn Trp Gly Arg
            180                 185                 190

Glu Glu Arg Gln Ser Ala Phe Pro Phe Glu Ser Gly Lys Pro Phe Lys
        195                 200                 205

Ile Gln Val Leu Val Glu Asp His Phe Lys Val Ala Val Asn Asp Val
    210                 215                 220

His Leu Leu Gln Tyr Asn His Arg Met Lys Asn Leu Arg Glu Ile Ser
225                 230                 235                 240

Gln Leu Gly Ile Ile Gly Asp Ile Thr Leu Thr Ser Ala Ser His Ala
                245                 250                 255

Met Ile
```

<210> SEQ ID NO 4
<211> LENGTH: 246
<212> TYPE: PRT
<213> ORGANISM: Homo sapiens

<400> SEQUENCE: 4

Met Ala Asp Asn Phe Ser Leu His Asp Ala Leu Ser Gly Ser Gly Asn

-continued

```
                1               5                  10                  15

Pro Asn Pro Gln Gly Trp Pro Gly Ala Trp Gly Asn Gln Pro Ala Gly
                20                  25                  30

Ala Gly Gly Tyr Pro Gly Ala Ser Tyr Pro Tyr Pro Gly Gln Ala
            35                  40                  45

Pro Pro Gly Ala Tyr Pro Gly Gln Ala Pro Gly Ala Tyr His Gly
        50                  55                  60

Ala Pro Gly Ala Tyr Pro Gly Ala Pro Ala Pro Gly Val Tyr Pro Gly
65                  70                  75                  80

Pro Pro Ser Gly Pro Gly Ala Tyr Pro Ser Ser Gly Gln Pro Ser Ala
                85                  90                  95

Pro Gly Ala Tyr Ala Thr Gly Pro Tyr Gly Ala Pro Ala Gly Pro Leu
                100                 105                 110

Ile Val Pro Tyr Asn Leu Pro Leu Pro Gly Gly Val Val Pro Arg Met
            115                 120                 125

Leu Ile Thr Ile Leu Gly Thr Val Lys Pro Asn Ala Asn Arg Ile Ala
        130                 135                 140

Leu Asp Phe Gln Arg Gly Asn Asp Val Ala Phe His Phe Pro Arg Phe
145                 150                 155                 160

Asn Glu Asn Asn Arg Arg Val Ile Val Cys Asn Thr Lys Leu Asp Asn
                165                 170                 175

Asn Trp Gly Arg Glu Glu Arg Gln Ser Val Phe Pro Phe Glu Ser Gly
                180                 185                 190

Lys Pro Phe Lys Ile Gln Val Leu Val Glu Pro Asp His Phe Lys Val
            195                 200                 205

Ala Val Asn Asp Ala His Leu Gln Tyr Asn His Arg Val Lys Lys Leu
        210                 215                 220

Asn Glu Ile Ser Lys Leu Gly Ile Ser Gly Asp Ile Asp Leu Thr Ser
225                 230                 235                 240

Ala Ser Tyr Thr Met Ile
                245

<210> SEQ ID NO 5
<211> LENGTH: 12
<212> TYPE: PRT
<213> ORGANISM: Rattus sp.

<400> SEQUENCE: 5

Ala Gln Tyr Glu Glu Leu Ile Ala Asn Gly Asp Met
1               5                   10

<210> SEQ ID NO 6
<211> LENGTH: 10
<212> TYPE: PRT
<213> ORGANISM: Rattus sp.

<400> SEQUENCE: 6

Lys Lys Pro Leu Val Tyr Asp Glu Gly Lys
1               5                   10

<210> SEQ ID NO 7
<211> LENGTH: 9
<212> TYPE: PRT
<213> ORGANISM: Rattus sp.
<220> FEATURE:
<221> NAME/KEY: misc_feature
<222> LOCATION: (4)..(4)
<223> OTHER INFORMATION: X may be any amino acid
<220> FEATURE:
```

```
-continued

<221> NAME/KEY: misc_feature
<222> LOCATION: (6)..(7)
<223> OTHER INFORMATION: X may be any amino acid
<220> FEATURE:
<221> NAME/KEY: misc_feature
<222> LOCATION: (9)..(9)
<223> OTHER INFORMATION: X may be any amino acid

<400> SEQUENCE: 7

Leu Leu Glu Xaa Thr Xaa Xaa Leu Xaa
1               5

<210> SEQ ID NO 8
<211> LENGTH: 8
<212> TYPE: PRT
<213> ORGANISM: Rattus sp.
<220> FEATURE:
<221> NAME/KEY: misc_feature
<222> LOCATION: (6)..(6)
<223> OTHER INFORMATION: X may be any amino acid
<220> FEATURE:
<221> NAME/KEY: misc_feature
<222> LOCATION: (8)..(8)
<223> OTHER INFORMATION: X may be any amino acid

<400> SEQUENCE: 8

Pro Ser Leu Asn Ser Xaa Glu Xaa
1               5

<210> SEQ ID NO 9
<211> LENGTH: 7
<212> TYPE: PRT
<213> ORGANISM: Rattus sp.
<220> FEATURE:
<221> NAME/KEY: misc_feature
<222> LOCATION: (4)..(4)
<223> OTHER INFORMATION: X may be any amino acid
<220> FEATURE:
<221> NAME/KEY: misc_feature
<222> LOCATION: (7)..(7)
<223> OTHER INFORMATION: X may be any amino acid

<400> SEQUENCE: 9

Ile Glu Leu Xaa Glu Ile Xaa
1               5

<210> SEQ ID NO 10
<211> LENGTH: 14
<212> TYPE: PRT
<213> ORGANISM: Rattus sp.

<400> SEQUENCE: 10

Pro Glu Ala Ile Lys Gly Ala Val Val Gly Ile Asp Leu Gly
1               5                   10
```